US009403763B2

(12) United States Patent
Sodroski et al.

(10) Patent No.: US 9,403,763 B2
(45) Date of Patent: Aug. 2, 2016

(54) CD4-MIMETIC INHIBITORS OF HIV-1 ENTRY AND METHODS OF USE THEREOF

(71) Applicants: Dana-Farber Cancer Institute, Inc., Boston, MA (US); The Trustees of the University of Pennsylvania, Philadelphia, PA (US); The United States of America As Represented By The Secretary, Department of Health and Human Services, Washington, DC (US); Bryn Mawr College, Bryn Mawr, PA (US); The Johns Hopkins University, Baltimore, MD (US); The Trustees of Columbia University in the City of New York, New York, NY (US)

(72) Inventors: Joseph Sodroski, Medford, MA (US); Judith M. LaLonde, Havertown, PA (US); Amos B. Smith, III, Merion, PA (US); Peter D. Kwong, Washington, DC (US); Young Do Kwon, Kensington, MD (US); David M. Jones, Philadelphia, PA (US); Alexander W. Sun, Eugene, OR (US); Joel R. Courter, Philadelphia, PA (US); Takahiro Soeta, Kanazawa (JP); Toyoharu Kobayashi, Tokyo (JP); Amy M. Princiotto, Attleboro, MA (US); Xueling Wu, Potomac, MD (US); John R. Mascola, Rockville, MD (US); Arne Schon, Baltimore, MD (US); Ernesto Freire, Baltimore, MD (US); Navid Madani, Westboro, MA (US); Matthew Le-Khac, Brooklyn, NY (US); Wayne A. Hendrickson, New York, NY (US); Jongwoo Park, Daejeon (KR)

( * ) Notice: Subject to any disclaimer, the term of this patent is extended or adjusted under 35 U.S.C. 154(b) by 0 days.

(21) Appl. No.: 14/365,389

(22) PCT Filed: Dec. 14, 2012

(86) PCT No.: PCT/US2012/069708
§ 371 (c)(1),
(2) Date: Jun. 13, 2014

(87) PCT Pub. No.: WO2013/090696
PCT Pub. Date: Jun. 20, 2013

(65) Prior Publication Data
US 2014/0350113 A1 Nov. 27, 2014

Related U.S. Application Data

(60) Provisional application No. 61/570,536, filed on Dec. 14, 2011.

(51) Int. Cl.
*C07C 237/06* (2006.01)
*A61K 31/167* (2006.01)
*A61K 31/185* (2006.01)
*C07C 279/16* (2006.01)
*C07D 233/88* (2006.01)
*C07D 235/02* (2006.01)
(Continued)

(52) U.S. Cl.
CPC ............ *C07C 279/16* (2013.01); *C07C 233/56* (2013.01); *C07C 237/06* (2013.01); *C07C 237/22* (2013.01); *C07C 279/12* (2013.01); *C07D 207/335* (2013.01); *C07D 207/34* (2013.01); *C07D 209/88* (2013.01); *C07D 209/94* (2013.01); *C07D 233/88* (2013.01); *C07D 235/02* (2013.01); *C07D 235/06* (2013.01); *C07D 271/07* (2013.01); *C07D 307/52* (2013.01); *A61K 31/167* (2013.01); *A61K 31/185* (2013.01); *C07C 2101/14* (2013.01); *C07C 2102/08* (2013.01)

(58) Field of Classification Search
CPC ... A61K 31/185; A61K 31/19; A61K 31/195; A61K 31/167; A01N 37/02; A01N 41/08; C07C 279/16; C07C 237/06
USPC .................... 514/578; 562/607; 564/153, 157
See application file for complete search history.

(56) References Cited

U.S. PATENT DOCUMENTS

| | | |
|---|---|---|
| 2007/0021450 A1 | 1/2007 | Sklarz et al. |
| 2012/0122834 A1 | 5/2012 | Sodroski et al. |
| 2014/0377219 A1 | 12/2014 | Debnath et al. |

FOREIGN PATENT DOCUMENTS

| | | |
|---|---|---|
| WO | WO-94/22826 A1 | 10/1994 |
| WO | WO-97/02027 A1 | 1/1997 |

(Continued)

OTHER PUBLICATIONS

LaLonde et al., "Design, synthesis and biological evaluation of small molecule inhibitors of CD4-gp120 binding based on virtual screening," Bioorganic & Medicinal Chemistry, 19:91-101 (2011).
(Continued)

*Primary Examiner* — Alicia L Otton
*Assistant Examiner* — Sagar Patel
(74) *Attorney, Agent, or Firm* — Baker & Hostetler, LLP

(57) ABSTRACT

Described herein are small-molecule mimics of CD4, which both enter the Phe43 cavity and target Asp368 of gp120, the HIV-1 envelope protein. Also described herein are methods of using these compounds to inhibit the transmission or progression of HIV infection. These compounds exhibit antiviral potency greater than that of a known antiviral, NBD-556, with 100% breadth against clade B and C viruses. Importantly, the compounds do not activate HIV infection of CD4-negative, CCR5-positive cells, in contrast to NBD-556.

21 Claims, 26 Drawing Sheets

(51) Int. Cl.

| | |
|---|---|
| C07D 235/06 | (2006.01) |
| C07D 271/07 | (2006.01) |
| C07D 207/335 | (2006.01) |
| C07D 207/34 | (2006.01) |
| C07D 209/88 | (2006.01) |
| C07D 209/94 | (2006.01) |
| C07D 307/52 | (2006.01) |
| C07C 279/12 | (2006.01) |
| C07C 233/56 | (2006.01) |
| C07C 237/22 | (2006.01) |

(56) References Cited

FOREIGN PATENT DOCUMENTS

| WO | WO-98/28268 A2 | 7/1998 | |
|---|---|---|---|
| WO | WO-98/55447 A1 | 12/1998 | |
| WO | WO 9924065 A1 | 5/1999 | |
| WO | WO-2004/082687 A1 | 9/2004 | |
| WO | WO-2005/032490 A2 | 4/2005 | |
| WO | WO-2006/020070 A2 | 2/2006 | |
| WO | WO-2010/053583 | 5/2010 | |
| WO | WO 2010053583 A2 * | 5/2010 | ........... C07D 205/04 |
| WO | WO-2011/109237 A2 | 9/2011 | |

OTHER PUBLICATIONS

LaLonde et al., "Structure-Based Design, Synthesis, and Characterization of Dual Hotspot Small-Molecule HIV-1 Entry Inhibitors," Journal of Medicinal Chemistry, 55:4382-4396 (2012).

International Search Report dated Mar. 11, 2013, from PCT/US12/60708.

Courter, et al., "Structure-Based Design, Synthesis and Validations of CD4-Mimetic Small Molecule Inhibitors of HIV-1 Entry: Conversion of a Viral Entry Agonist to an Antagonist", Accounts of Chemical Research, Feb. 6, 2014, 47: 1228-1237.

Halford, "Aiming for HIV's Weak Spot", Chemical & Engineering News, At War with HIV, Attacking the Virus Where it's Vulnerable, Chemical & Engineering News, Sep. 1, 2014, 14-21.

Madani, et al., "CD4-Minetic Small Molecules Sensitize Human Immunodeficiency Virus to Vaccine-Elicited Antibodies", Journal of Virology, Jun. 2014, 88(12):6542-55.

Richard, et al., "CD4 Mimetics Sensitize HIV-1-Infected Cells to ADCC", PNAS, May 4, 2015, 112(20): E2687-E2694.

Kassa, et al., "Transitions to and from the CD4-Bound Conformation are Modulated by a Single-Residue Change in the Human Immunodeficiency Virus Type 1 gp120 Inner Domain", J. Virol., Sep. 2009, vol. 83(17), 8364-8378.

Kwon, et al., "Crystal Structures of HIV-1 gp120 Envelope Glycoprotein in Complex with NBD Analogues that Target the CD4-Binding Site", PLOS One, Jan. 28, 2014, vol. 9(1), 12 pgs.

Lalonde, et al., "Structure-Based Design and Synthesis of an HIV-1 Entry Inhibitor Exploiting X-Ray and Thermodynamic Characterization", ACS Med. Chem. Letter, Mar. 14, 2013, vol. 4(3), 338-343.

Madani, et al., "Small-Molecule CD4 Mimics Interact with a Highly Conserved Pocket on HIV-1 gp120", Structure, Nov. 12, 2008, vol. 16(11), 1689-1701.

Munro, et al., "Conformational Dynamics of Single HIV-1 Envelope Trimers on the Surface of Native Virions", Science, Nov. 7, 2014, vol. 46(6210), 759-763.

Xie, et al., "Structure-Activity Relationships in the Binding of Chemically Derivatized CD4 to gp120 from Human Immunodeficiency Virus", J. Med. Chem., Oct. 4, 2007, vol. 50(20), 4898-4908.

* cited by examiner

| | TS-II-224 | AWS-1-50 | DMJ-I-228 | AWS-1-169 |
|---|---|---|---|---|
| Data collection | | | | |
| Space group | $P2_1$ | $P2_1$ | $P2_12_12_1$ | $P2_1$ |
| Cell dimensions | | | | |
| $a, b, c$ (Å) | 64.72, 68.90, 94.51 | 64.66, 68.48, 94.74 | 63.74, 67.52, 89.25 | 65.44, 68.60, 94.54 |
| $a, b, g$ (°) | 90, 91.23, 90 | 90.0, 91.60, 90 | 90, 90, 90 | 90, 91.38, 90 |
| Resolution (Å) | 50-2.0(2.03-2.00)* | 50-1.80(1.83-1.80) | 46.3-1.88(1.9-1.88) | 50-1.80(1.83-1.80) |
| $R_{sym}$ | 0.09 (0.49) | 0.06 (0.59) | 0.09 (0.37) | 0.08 (0.57) |
| $I/sI$ | 11.5 (1.5) | 19.4 (1.1) | 34.7 (2.5) | 17.5 (1.8) |
| Completeness (%) | 94.1 (74.0) | 97.0 (72.9) | 97.4 (72.1) | 93.3 (55.0) |
| Redundancy | 3.1 (1.9) | 3.3 (1.9) | 5.2 (2.0) | 6.5 (3.2) |
| Refinement | | | | |
| Resolution (Å) | 41-1.98 | 33.7-1.79 | 46.3-1.88 | 33.7-1.80 |
| No. reflections | 53,979 | 74,205 | 29,830 | 72,604 |
| $R_{work}/R_{free}$ | 20.3/23.7 | 19.2/22.1 | 19.3/23.3 | 18.1/20.2 |
| No. atoms | | | | |
| Protein | 5,308 | 5,308 | 2,654 | 5,308 |
| Ligand/ion | 374 | 316 | 196 | 350 |
| Water | 330 | 437 | 199 | 416 |
| B-factors | | | | |
| Protein | 41.1 | 40.1 | 33.7 | 45.1 |
| Ligand/ion | 59.5 | 53.5 | 51.2 | 55.7 |
| Water | 40.7 | 41.6 | 39.5 | 45.1 |
| R.m.s. deviations | | | | |
| Bond lengths (Å) | 0.004 | 0.005 | 0.007 | 0.004 |
| Bond angles (°) | 0.796 | 0.938 | 0.869 | 0.887 |

Fig. 4

| R5T4 IC$_{50}$ (μM) | [structure] | YA-II-37 racemic | [structure] | DMJ-II-121 racemic | [structure] | DMJ-I-228 | [structure] | TS-II-224 |
|---|---|---|---|---|---|---|---|---|
| YU2 | | 21.8 +/- 1.2 | | 8.9 +/- 1.9 | | 13.3 +/- 3.7 | | 88.2 +/- 4.0 |
| AMLV | | >100 | | >100 | | >100 | | >100 |
| n | | 1 | | 3 | | 3 | | 3 |

| R5 Enhancement | YA-II-37 racemic | DMJ-II-121 racemic | DMJ-I-228 | TS-II-224 |
|---|---|---|---|---|
| YU2 | 0.00 | 0.00 | 0.03 | 1.00 |
| AMLV | 0.00 | 0.00 | 0.00 | 0.00 |
| n | 1 | 3 | 3 | 3 |

| Cmpd[a] | YU2 IC$_{50}$ μM[b] | YU2 S375W IC$_{50}$ μM[b] | 89.6 IC$_{50}$ μM[b] | KB9 IC$_{50}$ μM[b] | HXBc2 IC$_{50}$ μM[b] | AMLV IC$_{50}$ μM[c] |
|---|---|---|---|---|---|---|
| TS-II-224 (2) | 56.0 +/- 7.0 (8) | >100 (3) | N.D. | 13.5 +/- 3.6 (4) | 9.7 +/- 4.0 (4) | 95.2 +/- 3.2 (8) |
| AWS-I-169 (9) | 25.1 +/- 7.5 (4) | >100 (3) | 6.6 +/- 0.2 (1) | N.D. | 8.1 +/- 2.2 (3) | >100 (9) |
| DMJ-I-228 (10) | 27.7 +/- 5.4 (9) | >100 (3) | 1.7 +/- 0.1 (1) | 11.6 +/- 2.6 (5) | 6.4 +/- 1.2 (5) | >100 (40) |

Figure 10

|  |  | IC50 (µM) | | | | IC80 (µM) | | | |
|---|---|---|---|---|---|---|---|---|---|
|  |  | CD4-Ig | DMJ-I-228 | AWS-I-169 | NBD-556 | CD4-Ig | DMJ-I-228 | AWS-I-169 | NBD-556 |
| Tier 1 | HXB2 | 0.00004 | 0.709 | 0.919 | 5.7 | 0.0001 | 2.4 | 2.5 | 22.0 |
| clade B | MN.3 | 0.00004 | 9.0 | 13.6 | 56.0 | 0.0001 | 66.7 | 100.0 | >100 |
| (n=7) | BaL.01 | 0.0002 | 4.8 | 13.7 | 53.5 | 0.0007 | 15.4 | 30.6 | >100 |
|  | BaL.26 | 0.0002 | 7.1 | 8.7 | 55.2 | 0.0007 | 17.8 | 22.6 | >100 |
|  | ADA | 0.0004 | 1.4 | 1.8 | 13.6 | 0.0013 | 6.0 | 6.5 | 79.7 |
|  | SF162 | 0.0005 | 3.6 | 2.8 | 21.0 | 0.0025 | 10.7 | 6.9 | 52.6 |
|  | SS1196.1 | 0.0054 | 0.851 | 2.1 | 8.8 | 0.0335 | 2.8 | 5.3 | 33.1 |
| Tier 2 | YU2 | 0.0007 | 18.6 | 22.4 | 58.5 | 0.0022 | 37.1 | 45.0 | >100 |
| clade B | 89.6 | 0.0012 | 2.9 | 3.5 | 12.2 | 0.006 | 6.9 | 6.7 | 32.9 |
| (n=18) | THRO.18 | 0.003 | 8.2 | 10.2 | 52.7 | 0.018 | 26.5 | 30.8 | >100 |
|  | REJO.67 | 0.009 | 3.8 | 3.0 | 16.0 | 0.124 | 24.0 | 20.5 | 68.6 |
|  | JR-FL | 0.002 | 51.6 | 54.9 | >100 | 0.009 | >100 | >100 | >100 |
|  | QH0692.42 | 0.004 | 2.9 | 1.7 | 27.4 | 0.020 | 8.7 | 4.9 | 100.0 |
|  | 6535.3 | 0.007 | 1.9 | 0.843 | 13.4 | 0.045 | 6.0 | 2.4 | 32.5 |
|  | RHPA.7 | 0.015 | 18.1 | 19.3 | >100 | 0.208 | 67.0 | 54.8 | >100 |
|  | 7165.18 | 0.052 | 0.446 | 0.481 | 6.1 | 0.516 | 1.4 | 1.2 | 29.0 |
|  | 6101.10 | 0.025 | 1.3 | 0.856 | 6.1 | 0.058 | 2.3 | 1.4 | 14.0 |
|  | PVO.4 | 0.143 | 8.3 | 6.3 | 68.6 | 0.503 | 25.1 | 16.8 | >100 |
|  | WITO.33 | 0.015 | 3.1 | 1.2 | 27 | 0.203 | 12.3 | 5.0 | >100 |
|  | SC422.8 | 0.161 | 4.0 | 3.6 | 81.6 | >1 | 22.1 | 13.3 | >100 |
|  | TRJO.58 | 0.470 | 38.5 | 31.1 | 72.9 | 0.941 | 63.7 | 47.1 | >100 |
|  | CAAN.A2 | 0.648 | 1.1 | 0.516 | 7.3 | >1 | 2.6 | 0.944 | 21.0 |
|  | BG1168.1 | 0.247 | 2.1 | 1.7 | 14.7 | >1 | 4.4 | 3.4 | 39.4 |
|  | AC10.29 | 0.082 | 3.6 | 5.9 | 62.9 | 1.0 | 15.9 | 13.8 | >100 |
|  | TRO.11 | >1 | 21.4 | 42.7 | >100 | >1 | 70.3 | >100 | >100 |
|  | breadth n=25 | 96% | 100% | 100% | 88% | 84% | 96% | 92% | 48% |
|  | geometric mean | 0.006 | 4.2 | 4.2 | 23.5 | 0.017 | 12.0 | 9.3 | 37.4 |
| Tier 1 clade C | MW965.26 | 0.00006 | 2.1 | 5.8 | 24.5 | 0.0005 | 30.9 | >100 | >100 |
| Tier 2 | ZM109.4 | 0.00048 | 19.6 | 23.3 | >100 | 0.004 | 57.4 | 72.1 | >100 |
| clade C | Du123.6 | 0.009 | 14.0 | 31.8 | >100 | 0.005 | 68.6 | >100 | >100 |
| (n=16) | Du172.17 | 0.011 | 42.8 | 50.9 | 68.4 | 0.066 | 78.5 | >100 | >100 |
|  | Du151.2 | 0.011 | 69.2 | 74.8 | >100 | 0.075 | >100 | >100 | >100 |
|  | CAP210.E8 | 0.017 | 35.6 | 40.8 | >100 | 0.217 | >100 | >100 | >100 |
|  | ZM233.6 | 0.029 | 9.6 | 10.0 | 42.2 | 0.207 | 25.6 | 25.2 | >100 |
|  | CAP244.D3 | 0.032 | 49.8 | 50.5 | >100 | 0.174 | >100 | >100 | >100 |
|  | ZM197.7 | 0.178 | 9.5 | 9.8 | 54.6 | >1 | 36.2 | 23.2 | >100 |
|  | ZM53.12 | 0.048 | 41.9 | 69.3 | 99.2 | 0.215 | >100 | >100 | >100 |
|  | ZM214.15 | 0.080 | 4.8 | 5.2 | >100 | >1 | 37.8 | 33.6 | >100 |
|  | ZM135.10a | 0.059 | 14.7 | 9.3 | 79.2 | 0.977 | 48.6 | 20.0 | >100 |
|  | ZM249.1 | 0.068 | 21.0 | 32.7 | 76.8 | 0.483 | 87.8 | >100 | >100 |
|  | Du422.1 | 0.259 | 40.2 | 57.2 | >100 | >1 | >100 | >100 | >100 |
|  | Du156.12 | >1 | 21.4 | 44.7 | >100 | >1 | >100 | >100 | >100 |
|  | ZM106.9 | 0.581 | 38.3 | 50.0 | >100 | >1 | >100 | >100 | >100 |
|  | CAP45.G3 | 0.145 | 23.1 | 33.3 | >100 | >1 | >100 | >100 | >100 |
|  | Breadth n=17 | 94% | 100% | 100% | 41% | 65% | 53% | 29% | 0% |
|  | Geometric mean | 0.025 | 20.0 | 26.5 | 58.4 | 0.060 | 48.3 | 30.9 | >100 |
| SIV | SIVmac251 | 0.004 | 64.1 | 58.0 | 72.6 | 0.070 | 87.8 | 77.6 | >100 |
| control | MuLV | >1 | >100 | >100 | >100 | >1 | >100 | >100 | >100 |

| Compound | HIV-1 YU-2 IC$_{50}$ (µM)[a] | A-MLV IC$_{50}$ (µM)[b] | Activation of Viral Infectivity[c] | K$_D$ (µM)[d] | ΔG (kcal/mol) | ΔH (kcal/mol) | -TΔS (kcal/mol) |
|---|---|---|---|---|---|---|---|
| (+)-4 | 2.3 +/- 0.05 (11) | >100 | 0.0 ± 0.0 (4) | 0.11 | -9.5 | -17.9 | +8.4 |
| (-)-4 | 37.9 +/- 22.7 (4) | >100 | 0.11 ± 0.11 (2) | 6.2 | -7.1 | -19.7 | +12.6 |
| (+)-5 | 28.2 +/- 5.9 (3) | >100 | 0.17 ± 0.15 (2) | 0.34 | -8.8 | -11.4 | +2.6 |
| (-)-5 | 68.5 +/- 31.5 (3) | >100 | 0.0 ± 0.0 (2) | 2 | -7.8 | -14.7 | +6.9 |

CD4-MIMETIC INHIBITORS OF HIV-1 ENTRY AND METHODS OF USE THEREOF

RELATED APPLICATIONS

This application is the National Stage application of PCT/US12/069708, filed Dec. 14, 2012, which claims the benefit of U.S. Provisional Application No. 61/570,536, filed on Dec. 14, 2011; the entire content of each application is incorporated herein in its entirety by this reference.

GOVERNMENT SUPPORT

This invention was made with government support under Grant GM 56550 awarded by the National Institutes of Health. The U.S. government has certain rights in the invention. This statement is included solely to comply with 37 C.F.R. §401.14(a)(f)(4) and should not be taken as an assertion or admission that the application discloses and/or claims only one invention.

BACKGROUND OF THE INVENTION

Targeting the early phase of HIV-1 infection, including virus entry, as a prophylactic modality is a focus of intense research. HIV-1 entry involves a series of events that include attachment to the host cell and fusion of the viral and target cell membranes. HIV-1 entry is mediated by the viral spike, which is composed of three gp120 envelope glycoproteins and three gp41 transmembrane molecules. In humans, HIV-1 infection begins with two consecutive gp120 binding events, each associated with major conformational changes in the gp120 structure. The first involves gp120 binding to the host CD4 receptor. CD4 binding results in a major gp120 conformational change, thus exposing a site for binding to the chemokine receptor (either CCR5 or CXCR4). Chemokine receptor binding is accompanied by gp41 rearrangement and the insertion of the gp41 fusion peptide into the host cell membrane, permitting fusion and viral entry. The highly conserved gp120-CD4 interface has been revealed by a number of X-ray crystal structures of the gp120 core domain, complexed to the D1D2 fragment of CD4 and a Fab of a human neutralizing antibody 17b, the latter serving as a surrogate for the co-receptors. CD4 binding induces the formation of a large internal cavity at the interface of the three gp120 domains, the inner domain, the outer domain, and the bridging sheet domain. The $Phe43_{CD4}$ and $Arg59_{CD4}$ residues have been shown by both mutagenesis and structural studies to be critical for binding of gp120 to CD4. Residue $Phe43_{CD4}$ is located on the CD4 CDR2-like loop and binds at the vestibule of the large cavity formed upon the CD4-induced gp120 conformational change; $Arg59_{CD4}$ is located on a neighboring β-strand and forms an electrostatic interaction with $Asp368_{gp120}$ at the cavity vestibule. The structure of the unbound form of the simian immunodeficiency virus (SIV) gp120, which has a 35% sequence identity with HIV-1 gp120, indicates an invariant outer domain, with conformational changes occurring in both the bridging sheet and inner domain. Recent studies indicate that the HIV-1 gp120 core exhibits a propensity to assume the CD4-bound conformation, but is restrained from doing so by gp120 variable loops and interactions with gp41 in the context of the trimer spike. The thermodynamic signature of the CD4-induced gp120 conformational change exhibits a highly favorable binding enthalpy balanced with a highly unfavorable entropy associated with molecular ordering.

Two N-phenyl-N'-(2,2,6,6,-tetramethyl-piperidin-4-yl)-oxalamide compounds, NBD-556 and NBD-557 (FIG. 7), were identified via screening a drug-like small-molecule library for inhibition of gp120-CD4 binding. Zhao, Q. et al. *Virology* 339, 213-25 (2005). The NBD chemotype is defined by three pharmacophores: Region I, a para-halogen substituted phenyl ring; Region II, an oxalamide linker, and Region III, a substituted piperidine ring (FIG. 7). Mutagenesis, modeling and synthesis of NBD analogues with improved binding affinity revealed that these small molecules bind to the highly conserved gp120 cavity and compete with CD4 binding. Schön, A. et al. *Biochemistry* 45, 10973-80 (2006); Schön, A. et al. *Chem Biol Drug Des:* 77, 161-165 (2011); Madani, N. et al. *Structure* 16, 1689-701 (2008); LaLonde, J. M. et al. *Bioorganic & Medicinal Chemistry* 19, 91-101 (2011). Exploration of structure-activity relationships (SAR) in Region III demonstrated that compounds with comparable binding affinities act both as CD4 antagonists (i.e., to inhibit HIV-1-infection of CD4+ cells) and as CD4 agonists (i.e., promote CCR5 binding and enhance viral infection in the absence of CD4). Madani, N. et al. *Structure* 16, 1689-701 (2008); LaLonde, J. M. et al. *Bioorganic & Medicinal Chemistry* 19, 91-101 (2011). Mimicry of CD4 was further demonstrated by the similarity of the NBD and CD4 thermodynamic signatures, both exhibiting a large unfavorable entropy change, $-T\Delta S$, to Gibbs energy (17.1 kcal/mol and 24.1 kcal/mol for NBD-556 and CD4, respectively) compensated by a large favorable enthalpy change (−24.5 kcal/mol and −34.5 kcal/mol for NBD-556 and CD4, respectively). Taken together, these results provided a rationale for further optimization of NBD analogues as inhibitors of HIV-1 viral entry by focusing on both Phe43 cavity and $Asp368_{gp120}$ hotspots.

While structure-activity relationships have been explored extensively, the current lead compound, TS-II-224 (2) (FIG. 7) has a binding affinity of 0.33 µM with an $IC_{50}$=89.9 µM. Modeling and subsequent crystal structures of TS-II-224 (2) and NBD-556 in complex with Glade C1086 gp120 verified that the NBD compounds bind in the Phe43 cavity. Moreover, the crystal structures reveal that the Region III tetramethylpiperidine interactions are dominated by van der Waals contacts rather than specific polar protein-ligand interactions. Thus, an essential component of the gp120-CD4 hotspot, the $Asp368_{gp120}$-$Arg59_{CD4}$ electrostatic interaction has not been successfully integrated into NBD small-molecule design. Previously, these features were incorporated in a small-molecule scaffold and a cyclic peptide. However, the problem remains refractory, as the spatial arrangement between the NBD Region II stem and $Asp368_{gp120}$ is near 90 degrees, a trajectory difficult to capture in small-molecule scaffolds.

There exists a need for small molecule inhibitors that mimic the crucial $Asp368_{gp}$ 120-$Arg59_{CD4}$ interaction at the dual gp120-CD4 hotspots. In certain embodiments, these CD4-mimetic compounds exhibit improved thermodynamic and antiviral properties.

SUMMARY OF THE INVENTION
In certain embodiments, the invention relates to a compound of Formula VII
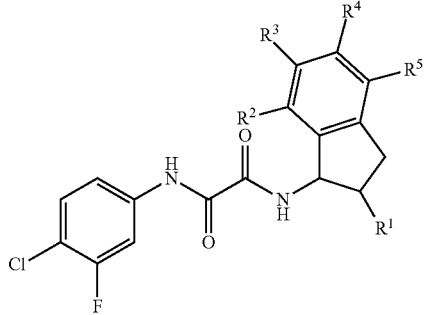
Formula VII
or a pharmaceutically acceptable salt or solvate thereof, wherein, independently for each occurrence,
$R^1$ is selected from the group consisting of optionally substituted amino,
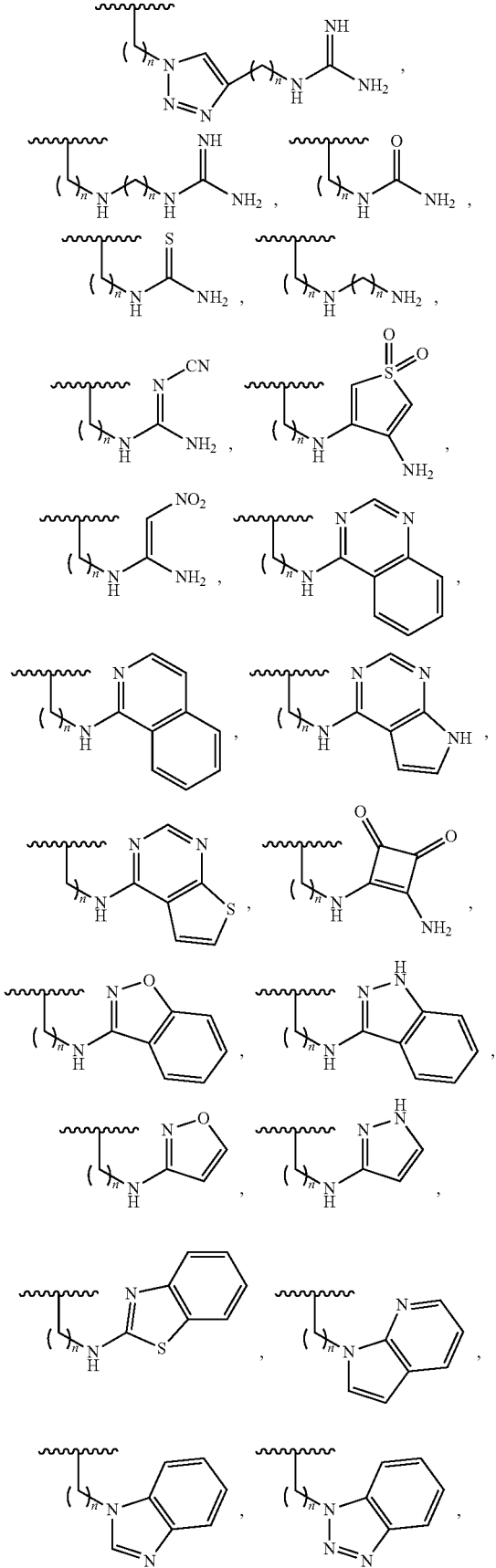

-continued

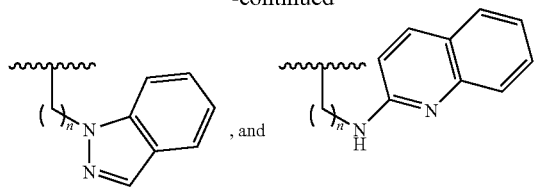
, and

R² is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R³ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁴ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁵ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo; and n is 0, 1, 2, 3, 4, or 5.

In certain embodiments, the invention relates to a compound of Formula I

Formula I

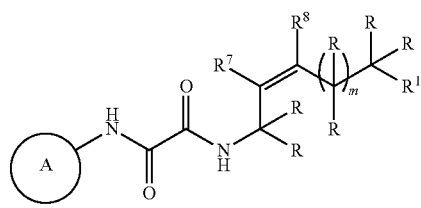

or a pharmaceutically acceptable salt or solvate thereof, wherein, independently for each occurrence,

is optionally substituted aryl or heteroaryl;

R¹ is selected from the group consisting of optionally substituted amino,

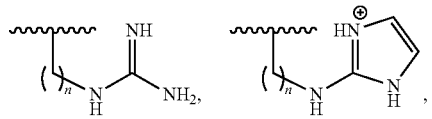

-continued

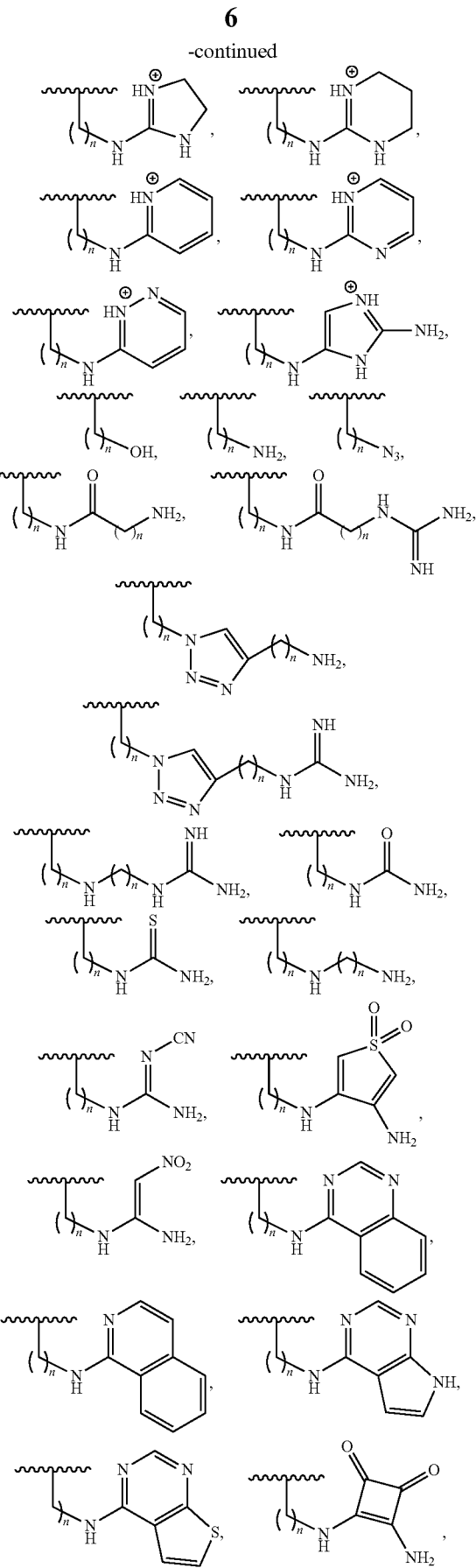

-continued

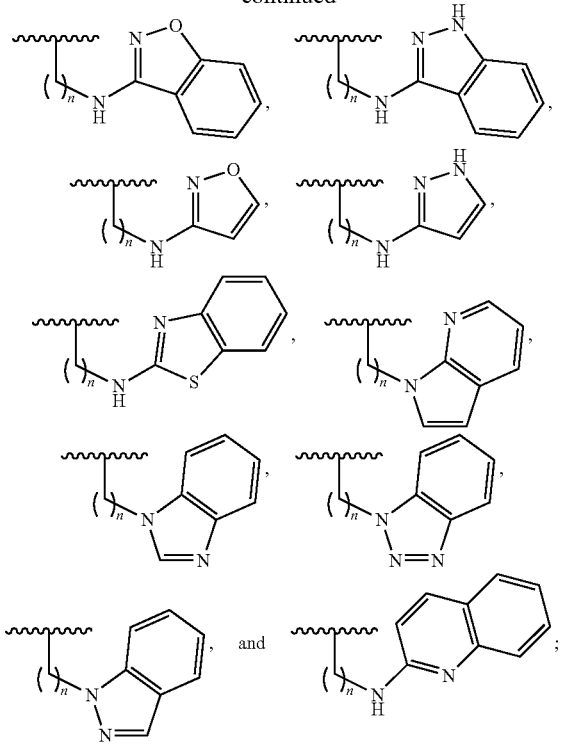

R⁷ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁸ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

or, R⁷ and R⁸, taken together, form an optionally substituted five-membered heteroaryl ring or an optionally substituted six-membered aryl or heteroaryl ring;

m is 1, 2, 3, or 4;

R is —H, optionally substituted alkyl, hydroxy, optionally substituted alkoxy, optionally substituted amino, or halo; and n is 0, 1, 2, 3, 4, or 5.

In certain embodiments, the invention relates to a compound of Formula II

Formula II

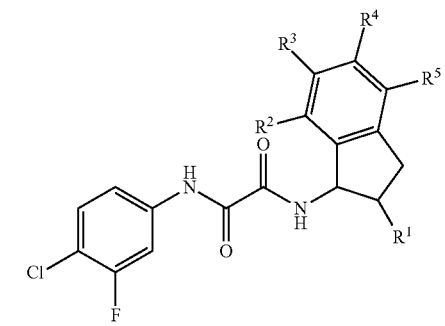

or a pharmaceutically acceptable salt or solvate thereof, wherein, independently for each occurrence,

Ⓐ is optionally substituted aryl or optionally substituted heteroaryl; and m is 1, 2, 3, or 4.

In certain embodiments, the invention relates to a compound of Formula III

Formula III or a pharmaceutically acceptable salt or solvate thereof, wherein, independently for each occurrence, $R^1$ is selected from the group consisting of optionally substituted amino,

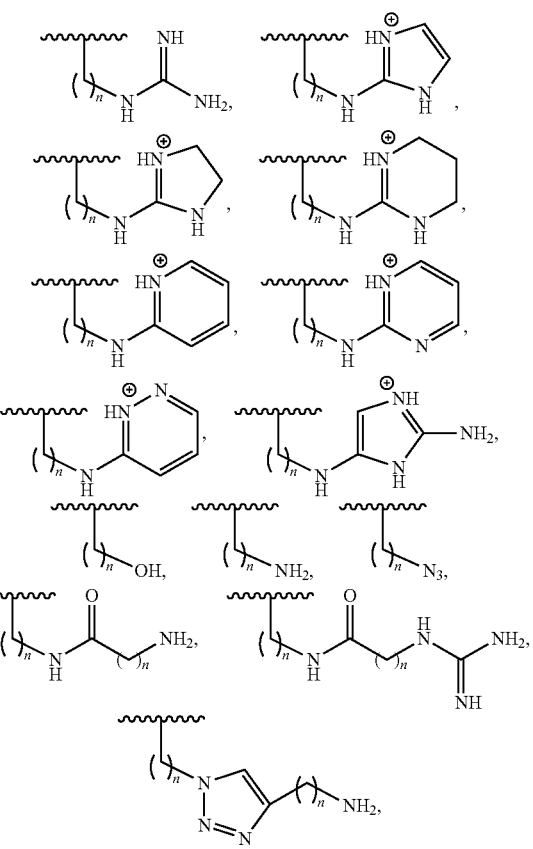

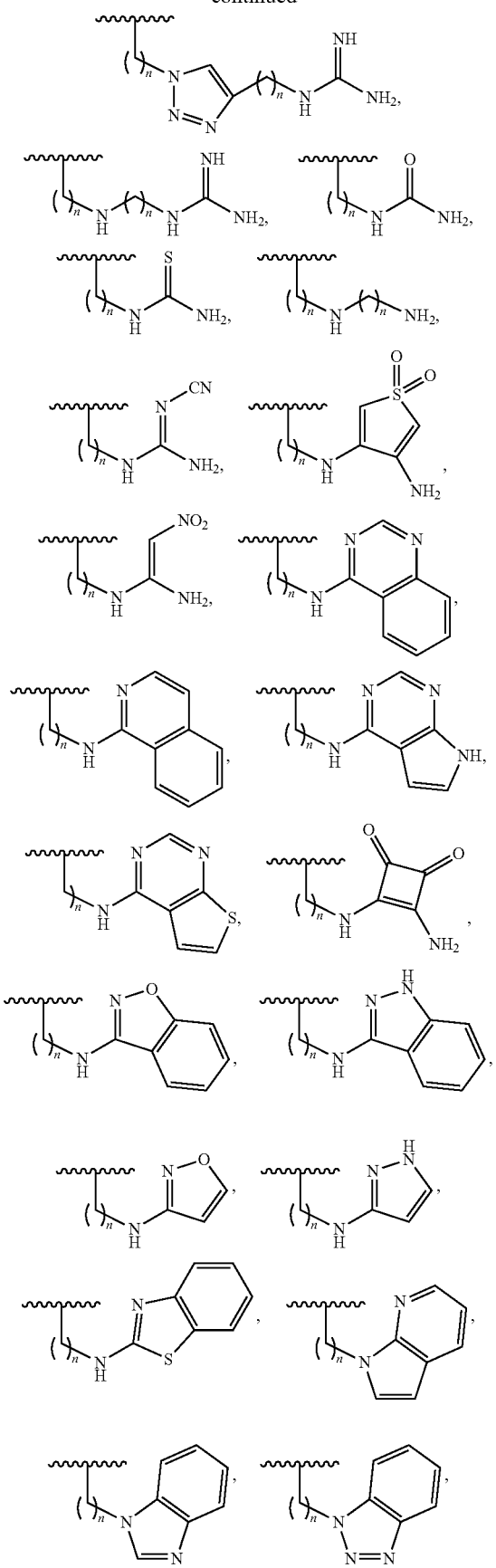

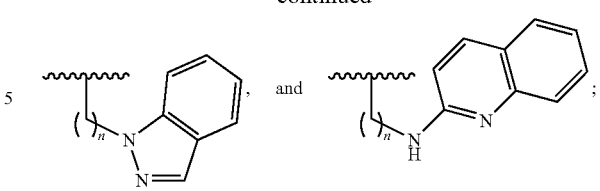

R² is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R³ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁴ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁵ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo; and n is 0, 1, 2, 3, 4, or 5.

In certain embodiments, the invention relates to a compound of Formula IV

Formula IV

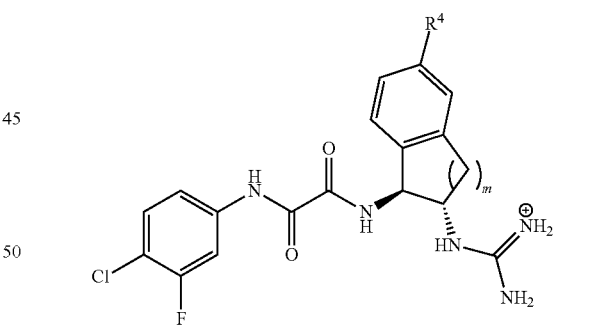

or a pharmaceutically acceptable salt or solvate thereof, wherein, independently for each occurrence, R⁴ is selected from the group consisting of halo, hydroxy, thio, optionally substituted alkylsulfonamido, optionally substituted cycloalkylsulfonamido, optionally substituted amino, optionally substituted amido, optionally substituted heterocyclyl, optionally substituted heteroaryl, and optionally substituted aryl; and m is 1, 2, 3, or 4.

In certain embodiments, the invention relates to a compound of Formula V

Formula V

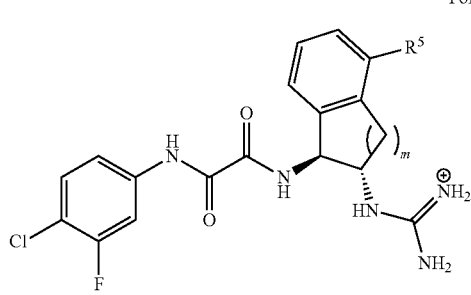

or a pharmaceutically acceptable salt or solvate thereof, wherein, independently for each occurrence, $R^5$ is selected from the group consisting of halo, hydroxy, thio, optionally substituted alkylsulfonamido, optionally substituted cycloalkylsulfonamido, optionally substituted amino, optionally substituted amido, optionally substituted heterocyclyl, optionally substituted heteroaryl, and optionally substituted aryl; and m is 1, 2, 3, or 4.

In certain embodiments, the invention relates to a compound of Formula VI

Formula VI

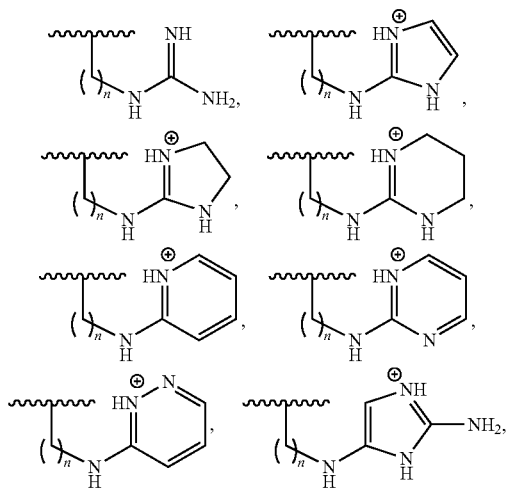

or a pharmaceutically acceptable salt or solvate thereof, wherein, independently for each occurrence, $R^1$ is selected from the group consisting of optionally substituted amino,

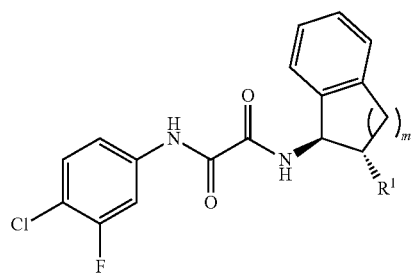

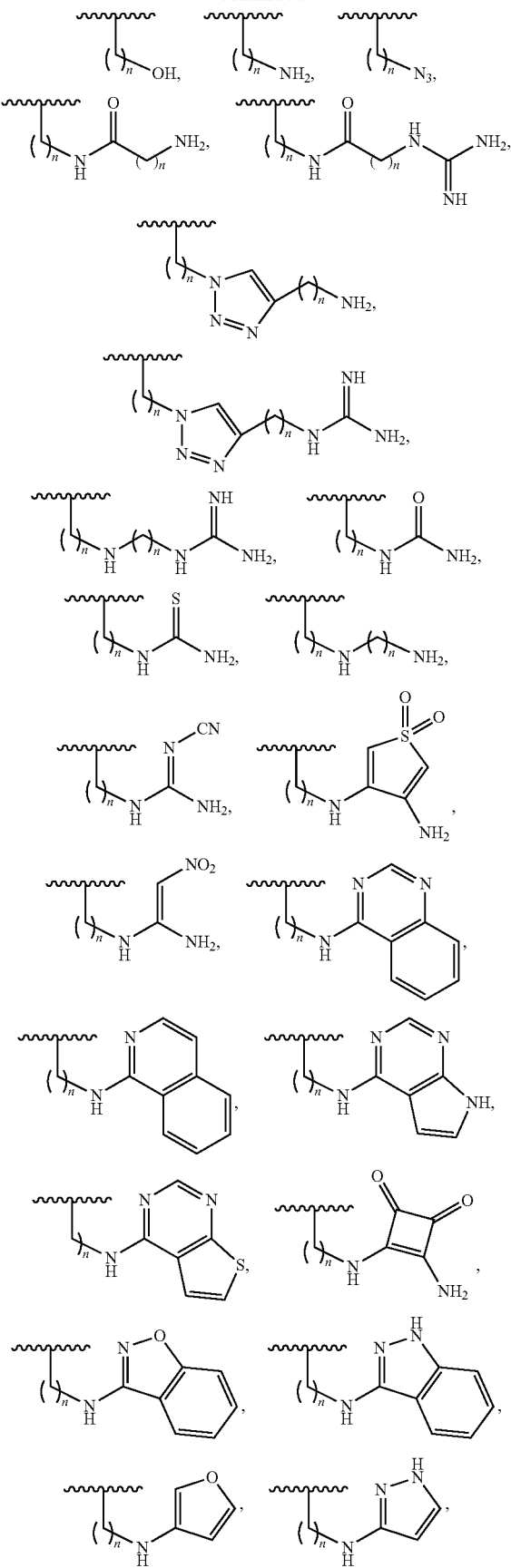

m is 1, 2, 3, or 4; and
n is 0, 1, 2, 3, 4, or 5.

In certain embodiments, the invention relates to a compound of Formula VIII

Formula VIII or a pharmaceutically acceptable salt or solvate thereof, wherein, independently for each occurrence, $R^{10}$ is optionally substituted aryl, optionally substituted heteroaryl, optionally substituted cycloalkyl, optionally substituted heterocycloalkyl, optionally substituted alkyl, or optionally substituted alkenyl;

$R^{11}$ is —H, optionally substituted alkyl, optionally substituted alkenyl, optionally substituted alkynyl, optionally substituted aryl, or optionally substituted heteroaryl; and $R^{12}$ is optionally substituted alkyl, optionally substituted alkenyl, optionally substituted alkynyl, optionally substituted aryl, or optionally substituted heteroaryl.

In certain embodiments, the invention relates to a compound, or a pharmaceutically acceptable salt thereof, selected from the group consisting of:

In certain embodiments, the invention relates to a method of activating HIV exterior envelope glycoprotein gp120 comprising the step of: contacting HIV with an effective amount of any one of the aforementioned compounds. In certain embodiments, the invention relates to a method of activating HIV exterior envelope glycoprotein gp120 comprising the step of: contacting HIV with an effective amount of a compound according to any one of Formulae I-VIII.

In certain embodiments, the invention relates to a method of inhibiting transmission of HIV to a cell comprising the step of: contacting HIV with an effective amount of any one of the aforementioned compounds, thereby inhibiting transmission of HIV to said cell. In certain embodiments, the invention relates to a method of inhibiting transmission of HIV to a cell comprising the step of: contacting HIV with an effective amount of a compound according to any one of one of Formulae I-VIII, thereby inhibiting transmission of HIV to said cell.

In certain embodiments, the invention relates to a method of inhibiting the progression of HIV infection in a cell comprising the step of: contacting HIV with an effective amount of any one of the aforementioned compounds, thereby inhibiting progression of HIV in the cell. In certain embodiments, the invention relates to a method of inhibiting the progression of HIV infection in a cell comprising the step of: contacting HIV with an effective amount of a compound according to any one of Formulae I-VIII, thereby inhibiting progression of HIV in the cell.

In certain embodiments, the invention relates to a method of inhibiting the transmission or progression of HIV to a cell comprising the steps of:
contacting HIV with an effective amount of any one of the aforementioned compounds; and
contacting HIV with an effective amount of an exogenous ligand mimicking the chemokine receptor expressed on said cell.

In certain embodiments, the invention relates to a method of inhibiting the transmission or progression of HIV to a cell comprising the steps of:
contacting HIV with an effective amount of a compound according to any one of Formulae I-VIII and
contacting HIV with an effective amount of an exogenous ligand mimicking the chemokine receptor expressed on said cell.

BRIEF DESCRIPTION OF THE FIGURES

FIG. 4 tabulates the data collection and refinement statistics (values in parentheses are for highest-resolution shell).

FIG. 8 tabulates the results from various assays for YA-II-37 (racemic) and DMJ-II-121 (racemic), as compared with DMJ-I-228 (10) and TS-II-224 (2). The top table tabulates $IC_{50}$ values for the compounds tested with HIV-1$_{YU2}$ and the negative control virus AMLV on cells co-expressing CCR5 and CD4. The bottom table tabulates the enhancement of viral entry for the compounds normalized to TS-II-224 (2).

FIG. 9 tabulates inhibition of viral entry among diverse HIV-1 strains. [a]Each compound was assayed in triplicate and is reported as a mean for one experiment. For multiple experiments the means and standard deviations are reported. The number of times independent experiments were performed is indicated in parenthesis. [b]The compound concentrations that inhibited 50% of virus infection ($IC_{50}$) was determined by infecting Cf2Th-CD4/CCR5 cells with 10,000 RT units of wild-type HIV-1$_{YU2}$ virus expressing luciferase with increasing concentrations of the compound. [c]The compound concentrations that inhibited 50% of virus infection ($IC_{50}$) when assayed against viruses with the ampotrophic murine leukemia virus (A-MLV) envelop glycoproteins.

FIG. 10 tabulates the neutralization profiles of CD4-Ig, DMJ-I-228 (10), AWS-I-169 (9), and NBD-556 (1) against Glade B and C reference viruses.

FIG. 13 tabulates inhibition of viral entry and CD4-gp120 binding and thermodynamic signatures for optimized antagonists. [a]$IC_{50}$ values were determined by infecting Cf2Th-CD4/CCR5 cells with wild-type HIV-1 YU2 virus expressing luciferase with increasing concentrations of the compounds. [b]The compound concentrations that inhibited 50% of virus infection ($IC_{50}$) of amphotropic murine leukemia virus (A-MLV). [c]The relative activation of viral infectivity was determined by infecting CD4 negative Cf2Th-CCR5 cells with HIV-1YU2 virus in the presence of the compounds normalized to that of $N^1$-(4-chlorophenyl)-$N^2$-(2,2,6,6-tetramethylpiperidin-4-yl)oxalamide. [d]The dissociation constant ($K_d$) and the thermodynamic parameters were determined by isothermal titration calorimetry at 25° C.

DETAILED DESCRIPTION OF THE INVENTION

Overview

Figures 1A, 1B, 1C:
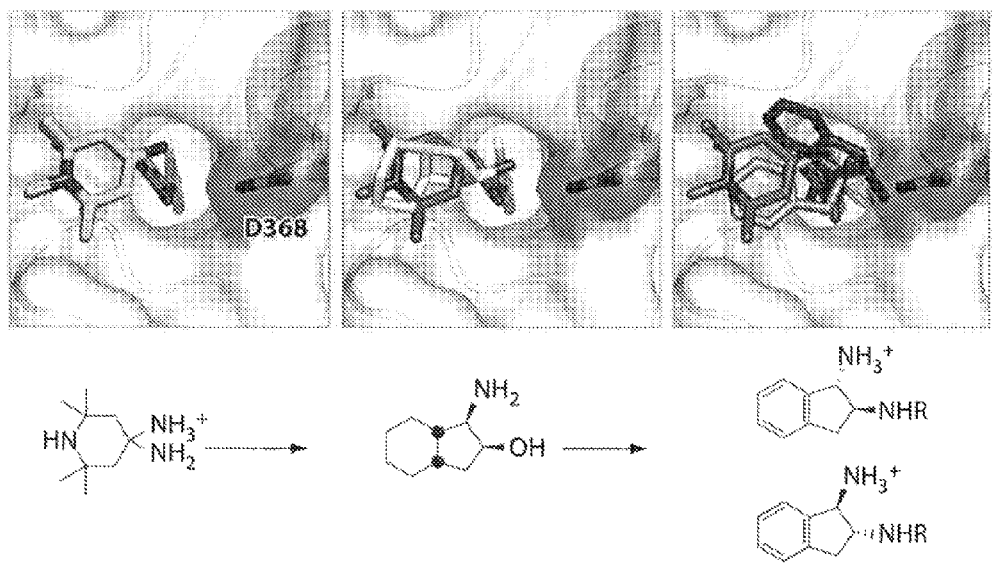
FIG. 1 depicts the structure-based design strategy. (a) Crystal structure of TS-II-224 (2) and docked model of prototype diamine tetramethylpiperidine used as a query in ROCS shape-based virtual screening. (b) 7-amino-8-bicyclo[4.3.0] nonanol hit molecule compared to TS-II-224 (2). (c) Docked conformations of the trans-1,2-diaminoindane isomers incorporated into the NBD region I and II scaffold, where R is indicated in FIG. 7.
Figure 2:
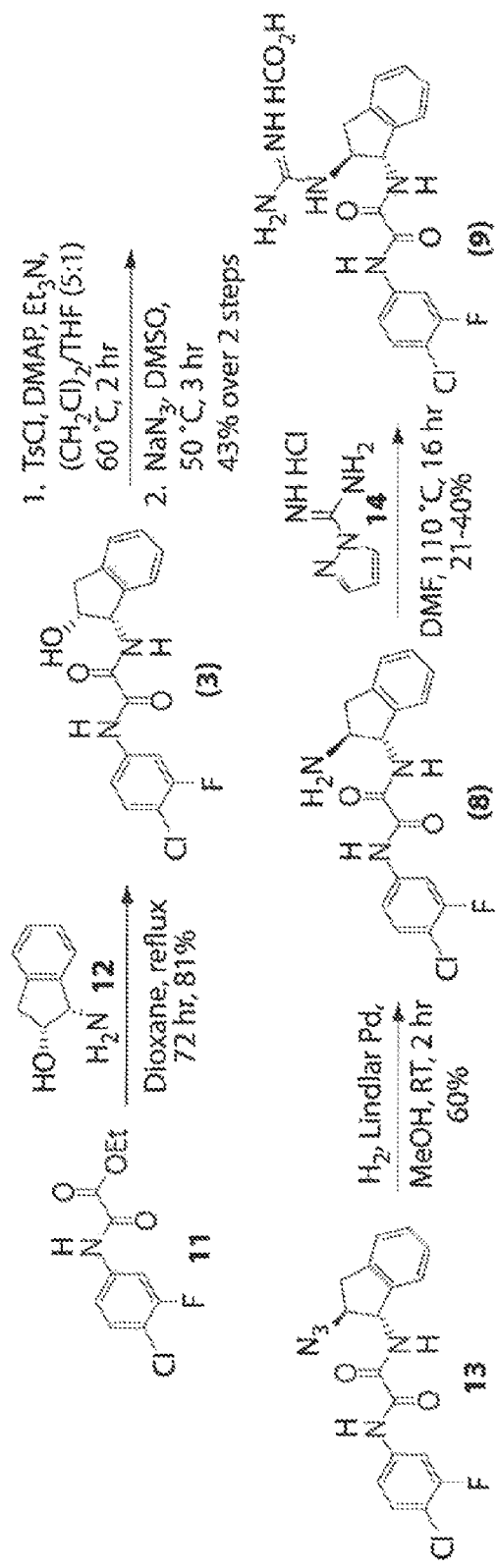
FIG. 2 depicts an exemplary synthesis of DMJ-I-228 (10). Note, the formate salt was obtained after purification by high-performance liquid chromatography. TsCl=tosyl chloride; DMAP=4-dimethylaminopyridine; DMSO=dimethyl sulfoxide; DMF=dimethylformamide.
Figure 3A:
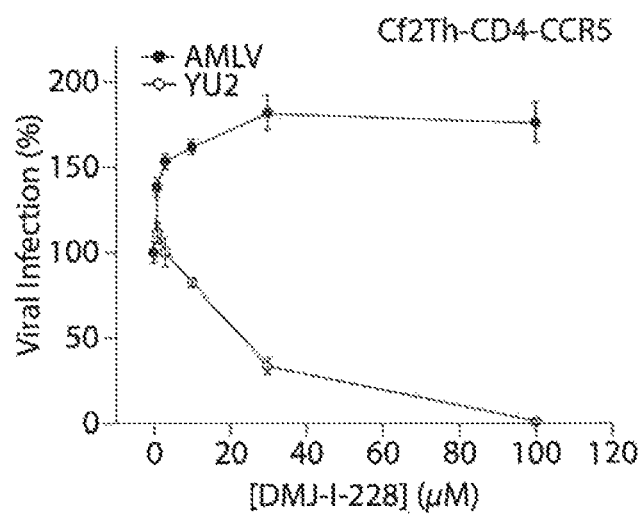
FIG. 3 depicts the viral and thermodynamic characterization of analogues AWS-I-169 (9) and DMJ-I-228 (10). (a) The effect of AWS-I-169 (9) and DMJ-I-228 (10) on the infection of Cf2Th-CD4-CXCR4 cells by recombinant luciferase-expressing HIV-1 envelope glycoproteins of the HXBc2, or KB9 strain of HIV-1 or the amphotropic murine leukemia virus (AMLV) is shown. (b) The effect of AWS-I-169 (9) and DMJ-I-228 (10) on the infection of Cf2Th-CD4-CCR5 cells by recombinant luciferase-expressing HIV-1 envelope glycoproteins of the YU2 or KB9 strain of HIV-1 or AMLV. Virus infection is expressed as the percentage of infection (measured by luciferase activity in the target cells) observed in the presence of DMJ-I-228 (10) relative to the level of infection observed in the absence of compound. The results are representative of 17 independent experiments. (c) Gibbs energy and its enthalpic ($\Delta H$) and entropic ($-T\Delta S$) contributions are compared for the binding of TS-II-224, AWS-I-45, AWS-I-169, AWS-I-50, and DMJ-I-228 and to gp120 at 25° C. d) The temperature dependence of the binding enthalpy for TS-II-224 (circles), AWS-I-169 (squares), and DMJ-I-228 (triangles). The changes in heat capacity, calculated from linear regression of the slopes, are $-738\pm36$ cal/(K×mol) for TS-II-224 (solid line), $-817\pm15$ cal/(K×mol) for AWS-I-169 (short dashed line), and $-398\pm5$ cal/(K×mol) for DMJ-I-228 (dashed line).
Figure 3B:
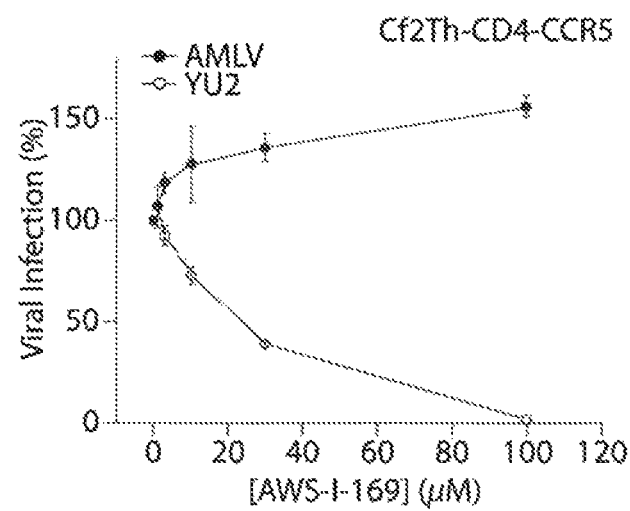
Figure 3C:
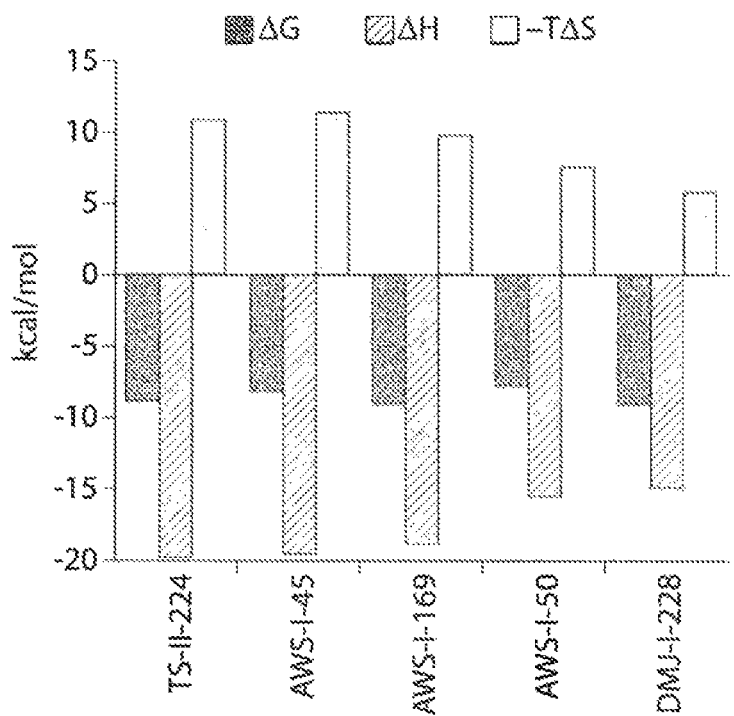
Figure 3D:
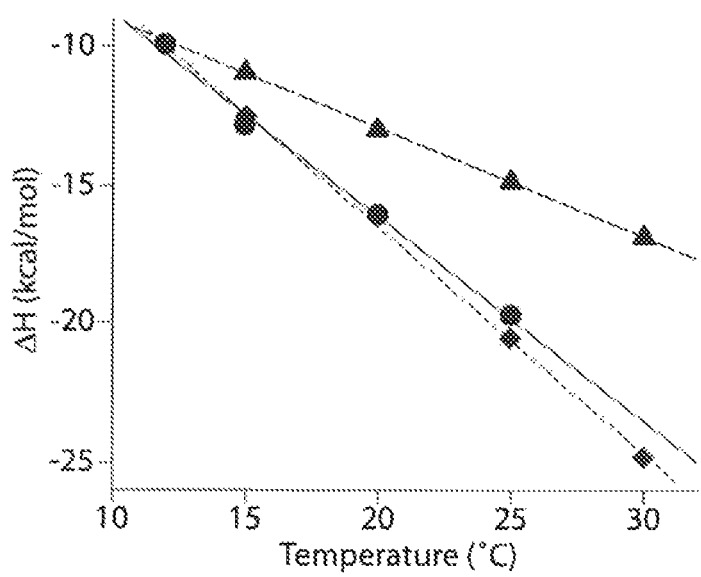

The 120-CD4 interface is characterized by two hotspots located on gp120, the large hydrophobic Phe43 cavity and $Asp368_{gp120}$ residing on adjacent α-helix 3. In certain embodiments, the invention relates to a modified ROCS "scaffold hopping" strategy, where instead of employing an existing lead compound, a prototype small molecule encompassing the desired features was used in virtual screening of chemical space for new moieties that meet chemotype and spatial requirements. In certain embodiments, the invention relates to the use of this ROCS screening strategy, followed by molecular design and synthesis, to identify two analogues of TS-II-224 (2) (which was previously described in WO2010/053583; this patent application is hereby incorporated by reference in its entirety), namely AWS-I-169 (9) and DMJ-I-228 (10), that employ a trans-1,2-disubstituted indane scaffold to direct a guanidinium group towards the $Asp368_{gp120}$ hotspot. The crystal structures described herein represent the highest resolution structure (1.8 Å) of small molecule-gp120 complexes to date. Not wishing to be bound by any particular theory, the guanidinium group of these indane analogs forms specific electrostatic interactions with $Asp368_{gp120}$. However, these interactions do not precisely mimic the $Asp368_{gp120}$-$Arg59_{CD4}$ salt-bridge observed in the gp120-CD4 complex. Instead, the crystal structures reveal two different water mediated hydrogen bonding networks between guanidinium group and $Asp368_{gp120}$. In the AWS-I-169 (9) complex, the network only exists between $Asp368_{120}$ and gp120 backbone atoms in the outer domain, while in the DMJ-I-228 (10) complex, the network spans both the bridging sheet domain and outer domain.

In certain embodiments, the invention relates to a method of inhibiting viral entry by AWS-I-169 (9) and DMJ-I-228 (10). In certain embodiments, the methods described herein are more efficient than any previously reported compound of the NBD class. In certain embodiments, AWS-I-169 (9) and DMJ-I-228 (10) have improved binding affinity and viral inhibition that neutralizes HIV-1 viruses from two major clades (clade B and C). Although both AWS-I-169 (9) and DMJ-I-228 (10) induce binding of both monomeric and full-length gp120 to the CCR5 surrogate 17b, in certain embodiments, neither compound enhances viral infectivity of CCR5-expressing cells that lack the CD4 receptor. Previous NBD analogues that trended towards smaller unfavorable entropy also exhibited reduced capacity to enhance viral infectivity of CCR5-expressing cells that lack the CD4 receptor. Schön, A. et al. *Chem Biol Drug Des:* 77, 161-165 (2011). In certain embodiments, the thermodynamic signature of AWS-I-169 (9) resembles that of TS-II-224 (2), whereas the binding of DMJ-I-228 (10) is characterized by smaller unfavorable entropy and negative heat capacity changes. Not wishing to be bound by any particular theory, given that optimization of protein-ligand interactions to improve binding affinity is more efficient when increasing enthalpic interactions without incurring an associated unfavorable entropic penalty, the smaller—TΔS term for DMJ-I-228 (10) may, in some embodiments, make this congener a more suitable candidate for continued development. Importantly, the four high-resolution structures of inhibitors of the gp120-CD4 interface, which include the $Asp368_{gp120}$ hotspot, hold the promise of a novel structural paradigm for continued cycles of design, synthesis and biological evaluation to develop further this class of small molecule gp120-CD4, HIV-1 entry inhibitors.

Definitions

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e. six carbons or less). For example "lower alkyl" refers to an alkyl group containing 1-6 carbons, and "lower alkenyl" refers to an alkenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "substituted alkyl" means an aliphatic or cyclic hydrocarbon radical containing from 1 to 12 carbon atoms, substituted with 1, 2, 3, 4, or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl and silyloxy.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, monocyclic, bicyclic (e.g. fused and spirocyclic) and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, haloalkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "N-heterocyclyl" as used herein is a subset of heterocyclyl, as defined herein, which have at least one nitrogen atom through which the N-heterocyclyl moiety is bound to the parent moiety. Representative examples include pyrrolidin-1-yl, piperidin-1-yl, piperazin-1-yl, hexahydropyrimidin-1-yl, morpholin-1-yl, 1,3-oxazinan-3-yl and 6-azaspiro[2.5]oct-6-yl. As with the heterocyclyl groups, the N-heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the N-heterocyclyl group through an alkylene moiety (e.g. methylene).

The term "aryl," as used herein means a phenyl group, naphthyl or anthracenyl group. The aryl groups of the present invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfinyl, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-yl-ethyl.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b) thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, haloalkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g. methylene).

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy. The terms "alkenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethyl-phenylethoxy, and 2,3-dimethylpyridinylmethoxy.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "oxy" refers to a —O— group.

The term "carbonyl" as used herein means a —C(=O)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "amino" as used herein refers to $-NH_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarnbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino The term "amido" as used herein means an amino group, as defined herein, appended to the parent molecular moiety through a carbonyl.

The term "cyano" as used herein means a $-C\equiv N$ group.

The term "nitro" as used herein means a $-NO_2$ group.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

As used herein, the term "administering" means providing a pharmaceutical agent or composition to a subject, and includes, but is not limited to, administering by a medical professional and self-administering.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the phrase "pharmaceutically-acceptable salts" refers to the relatively non-toxic, inorganic and organic salts of compounds.

As used herein, the term "subject" means a human or non-human animal selected for treatment or therapy.

As used herein, the phrase "subject suspected of having" means a subject exhibiting one or more clinical indicators of a disease or condition.

As used herein, the phrase "therapeutic effect" refers to a local or systemic effect in animals, particularly mammals, and more particularly humans, caused by an agent. The phrases "therapeutically-effective amount" and "effective amount" mean the amount of an agent that produces some desired effect in at least a sub-population of cells. A therapeutically effective amount includes an amount of an agent that produces some desired local or systemic effect at a reasonable benefit/risk ratio applicable to any treatment. For example, certain agents used in the methods of the present invention may be administered in a sufficient amount to produce a reasonable benefit/risk ratio applicable to such treatment.

As used herein, the term "treating" a disease in a subject or "treating" a subject having or suspected of having a disease refers to subjecting the subject to a pharmaceutical treatment, e.g., the administration of an agent, such that at least one symptom of the disease is decreased or prevented from worsening.

As used herein, "HIV" refers to any virus that can infect a host cell of a subject through activation of the gp120 envelope glycoproteins (Env gps). "HIV" encompasses all strains of HIV-1 and HIV-2. Compounds of the present invention, however, are also useful to treat other immunodeficiency viruses expressing gp120 such as some strains of simian immunodeficiency virus SIV.

As used herein "gp120" refers to the gp120 envelope glycoprotein, and "Env gps" refers to the complete envelope glycoprotein complex which is a trimer of three gp120s and three gp41s.

As used herein, the term "activating" when referring to gp120 envelope glycoprotein means the association of a natural or non-natural ligand with the conserved domain of gp 120 that induces a conformational change that activates binding to the chemokine receptors CCR5 or CXCR4. Examples of natural ligands include CD4 and sCD4. Examples of non-natural ligands include compounds of the present invention as well as NBD-556 and NBD-557.

As used herein "activated intermediate" refers to the gp120 envelope glycoprotein in bound form with CD4, sCD4, or compounds of the present invention.

As used herein, the term "contacting" when used in the context of compounds of the present invention and gp120, refers to the process of supplying compounds of the present invention to the HIV envelope glycoprotein either in vitro or in vivo in order effect the selective binding of the compounds of the present invention to the conserved Phe43 binding pocket of gp120. For the in vitro process, this can entail simply adding an amount of a stock solution of one or more compounds of the present invention to a solution preparation of gp120. For an in vivo process, "selective binding" involves making compounds of the present invention available to interact with gp120 in a host organism, wherein the compounds of the invention exhibit a selectivity for the conserved domain of gp120 that define the Phe43 cavity. Making the compounds available to interact with gp120 in the host organism can be achieved by oral administration, intravenously, peritoneally, mucosally, intramuscularly, and other methods familiar to one of ordinary skill in the art.

As used herein, the term "inhibiting" when referring to transmission means reducing the rate of or blocking the process that allows fusion of the viral glycoprotein gp120 to a host cell and introduction of the viral core into the host cell. In this regard, inhibiting transmission includes prophylactic measures to prevent viral spread from one host organism to another. When referring to progression, "inhibiting" refers to the treatment of an already infected organism and preventing further viral invasion within the same organism by blocking the process that allows fusion of the viral glycoprotein gp120 and introduction of viral core into additional host cells of the organism.

Exemplary Compounds

In certain embodiments, the invention relates to a compound of Formula VII

Formula VII or a pharmaceutically acceptable salt or solvate thereof, wherein, independently for each occurrence, $R^1$ is selected from the group consisting of optionally substituted amino,

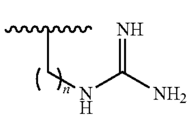

, 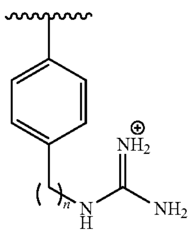  ,

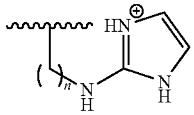

, 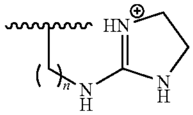  ,

-continued

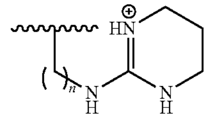

, 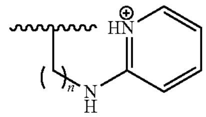  ,

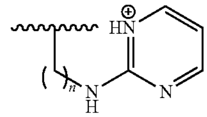

, 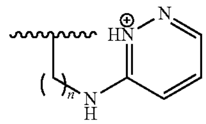  ,

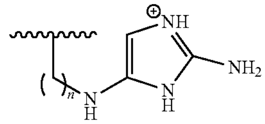

, 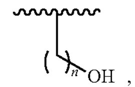  ,

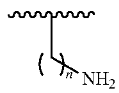

,  , 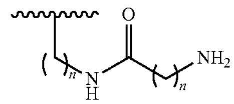  ,

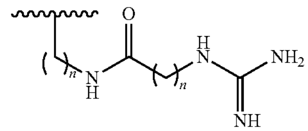

,

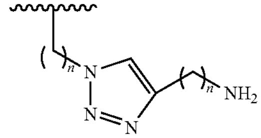

,

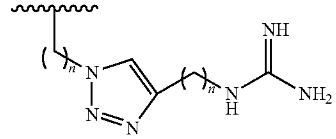

,

, 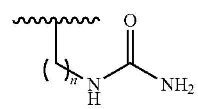  ,

, 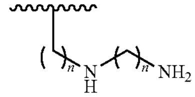  ,

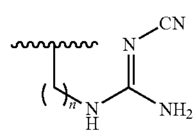

, 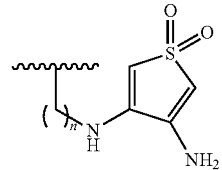  ,

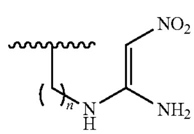

, 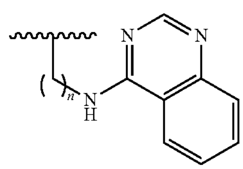  ,

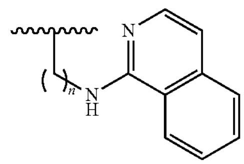

,  ,

,  ,

-continued

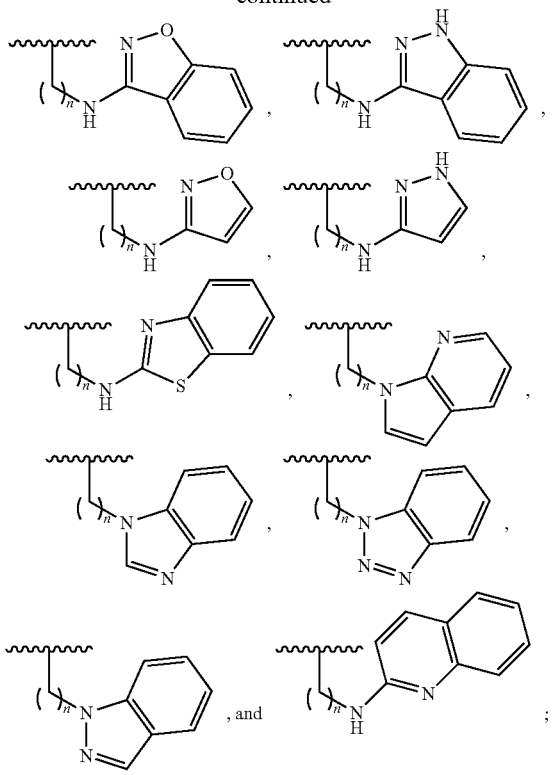

R² is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R³ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁴ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁵ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo; and n is 0, 1, 2, 3, 4, or 5.

In certain embodiments, the invention relates to a compound of Formula I

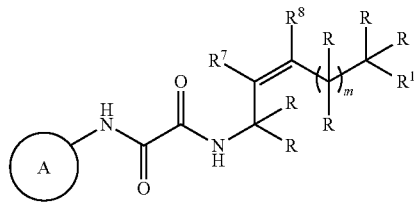

Formula I or a pharmaceutically acceptable salt or solvate thereof, wherein, independently for each occurrence,

is optionally substituted aryl or heteroaryl;

$R^1$ is selected from the group consisting of optionally substituted amino,

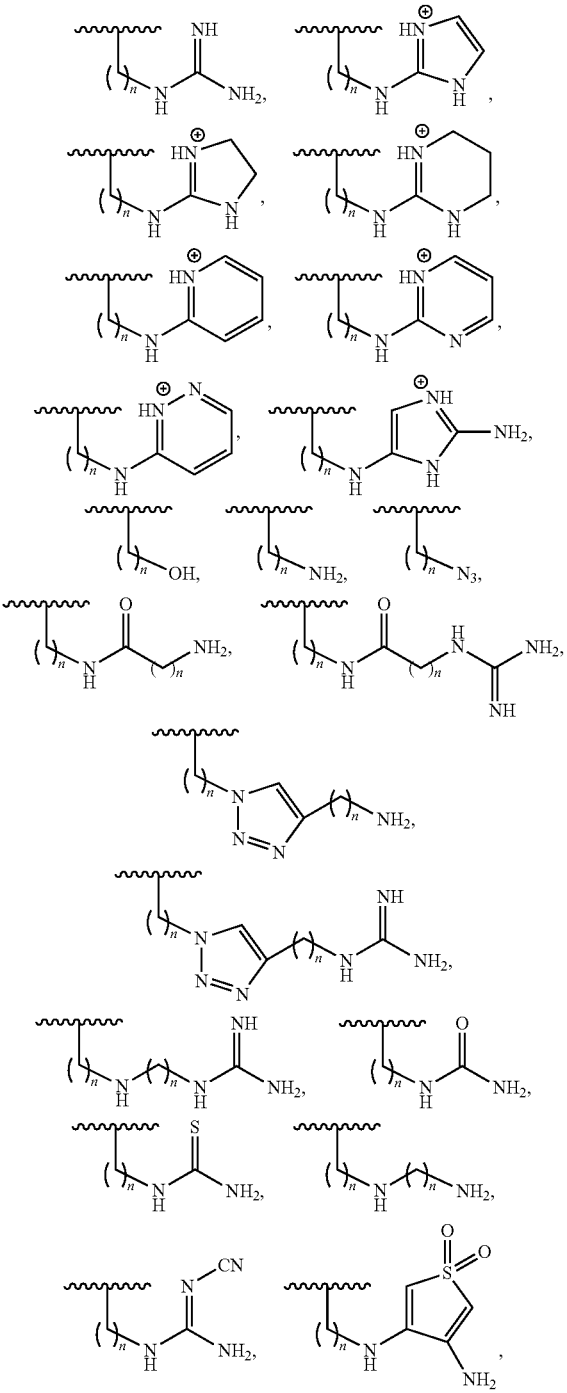

-continued

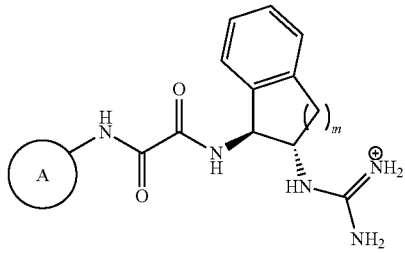

R[7] is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R[8] is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

or, R[7] and R[8], taken together, form an optionally substituted five-membered heteroaryl ring or an optionally substituted six-membered aryl or heteroaryl ring;

m is 1, 2, 3, or 4;

R is —H, optionally substituted alkyl, hydroxy, optionally substituted alkoxy, optionally substituted amino, or halo; and n is 0, 1, 2, 3, 4, or 5.

In certain embodiments, the invention relates to a compound of Formula II

Formula II or a pharmaceutically acceptable salt or solvate thereof, wherein, independently for each occurrence, is optionally substituted aryl or optionally substituted heteroaryl; and m is 1, 2, 3, or 4.

In certain embodiments, the invention relates to a compound selected from the group consisting of -continued

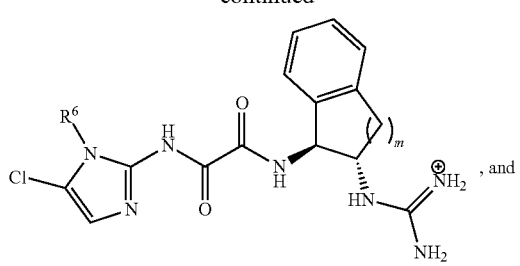

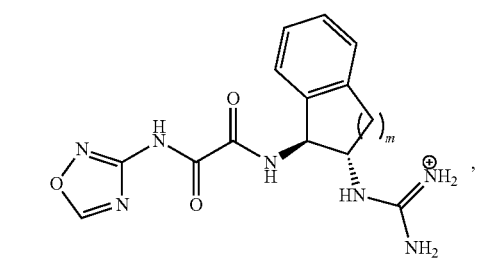

wherein,

R⁶ is selected from the group consisting of —H, optionally substituted alkyl, optionally substituted aralkyl, optionally substituted heteroaralkyl, optionally substituted alkylcarbonyl, optionally substituted cycloalkylsulfonyl, and optionally substituted alkylsulfonyl; and m is 1, 2, 3, or 4.

In certain embodiments, the invention relates to any one of the aforementioned compounds, wherein R⁶ is selected from the group consisting of

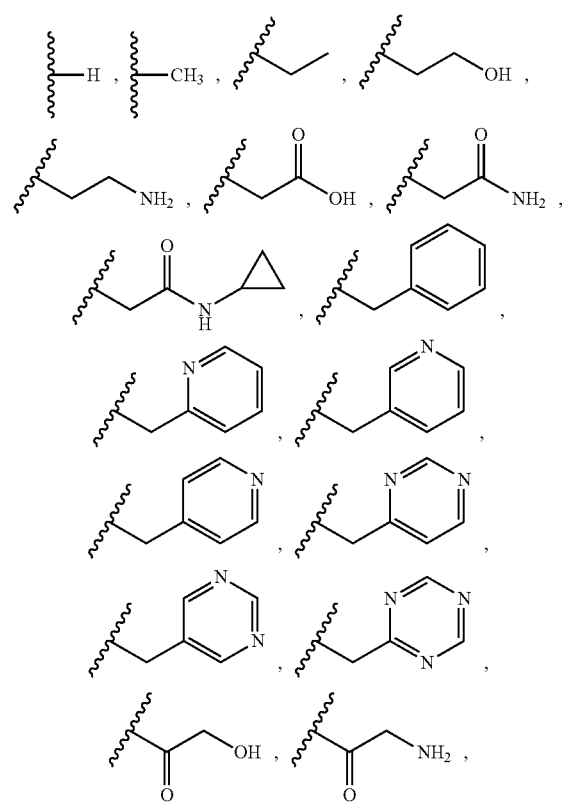

-continued

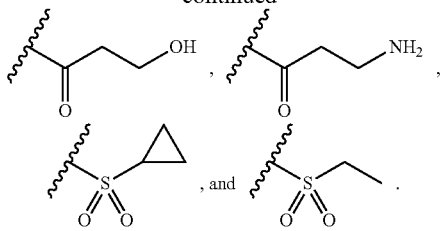

In certain embodiments, the invention relates to any one of the aforementioned compounds, wherein m is 1 or 2.

In certain embodiments, the invention relates to any one of the aforementioned compounds, wherein m is 1.

In certain embodiments, the invention relates to a compound of Formula III

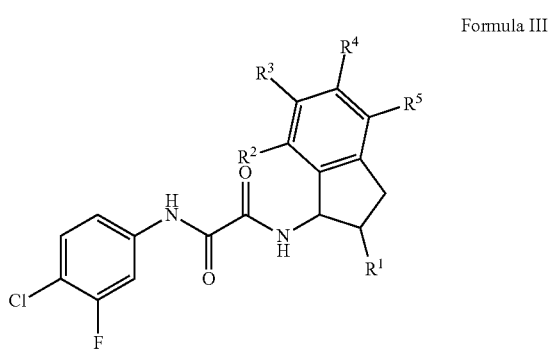

Formula III or a pharmaceutically acceptable salt or solvate thereof, wherein, independently for each occurrence, R¹ is selected from the group consisting of optionally substituted amino,

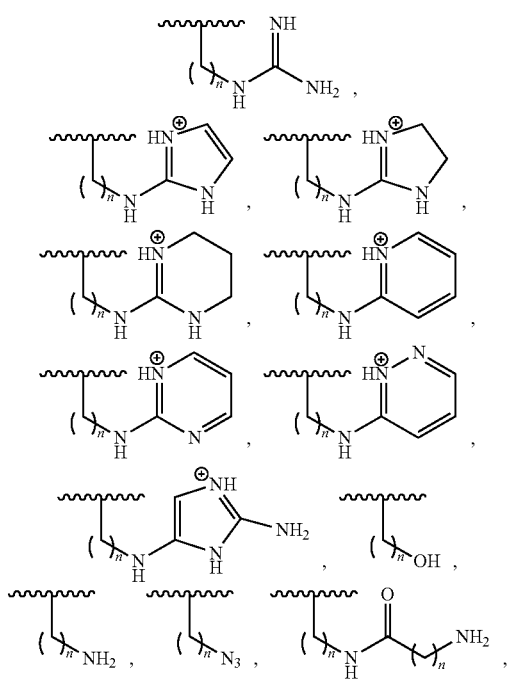

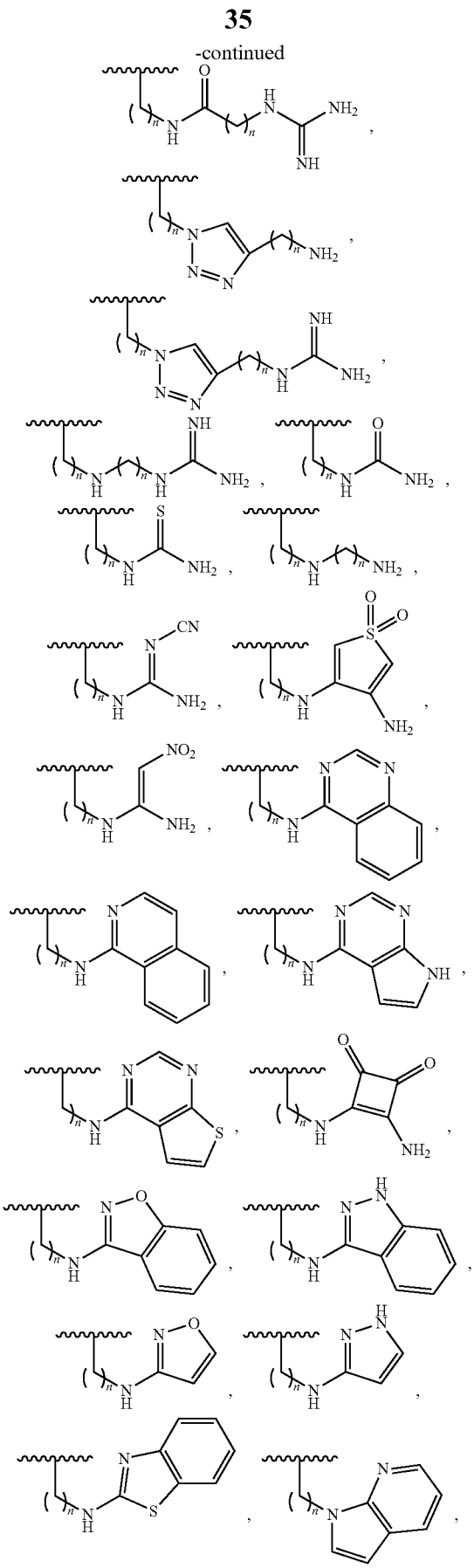

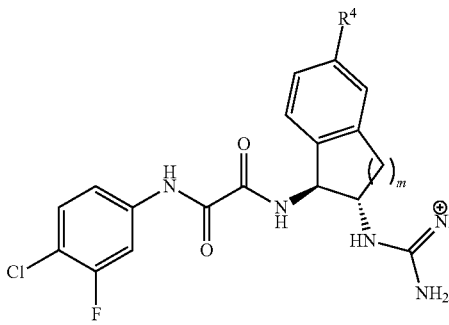

$R^2$ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

$R^3$ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

$R^4$ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

$R^5$ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo; and n is 0, 1, 2, 3, 4, or 5.

In certain embodiments, the invention relates to a compound of Formula IV

Formula IV or a pharmaceutically acceptable salt or solvate thereof, wherein, independently for each occurrence, $R^4$ is selected from the group consisting of halo, hydroxy, thio, optionally substituted alkylsulfonamido, optionally substituted cycloalkylsulfonamido, optionally substituted amino, optionally substituted amido, optionally substituted heterocyclyl, optionally substituted heteroaryl, and optionally substituted aryl; and m is 1, 2, 3, or 4.

In certain embodiments, the invention relates to any one of the aforementioned compounds, wherein $R^4$ is selected from the group consisting of

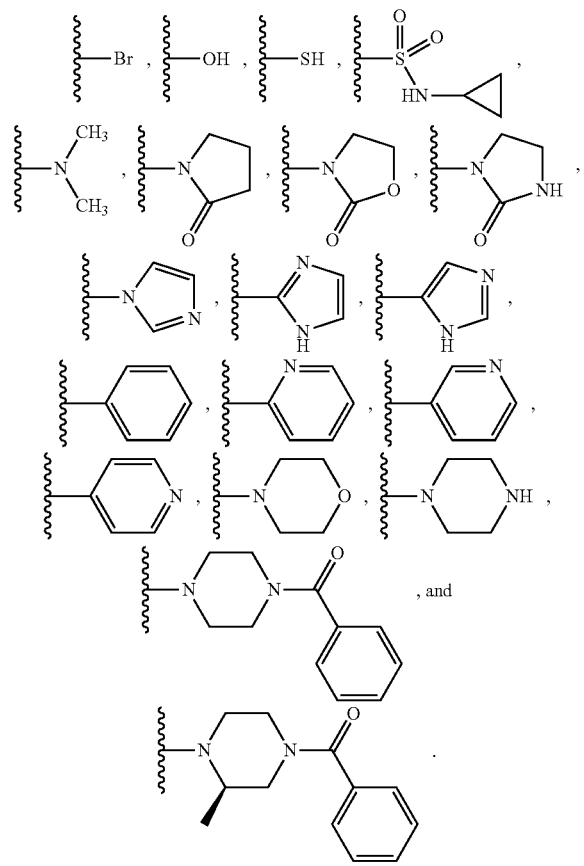

In certain embodiments, the invention relates to any one of the aforementioned compounds, wherein m is 1 or 2.

In certain embodiments, the invention relates to any one of the aforementioned compounds, wherein m is 1.

In certain embodiments, the invention relates to a compound of Formula V

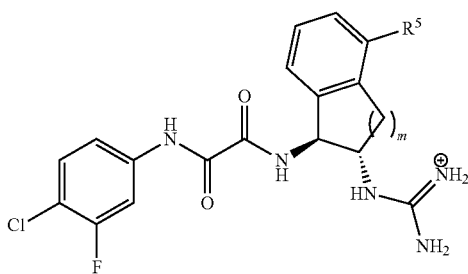

Formula V or a pharmaceutically acceptable salt or solvate thereof, wherein, independently for each occurrence, $R^5$ is selected from the group consisting of halo, hydroxy, thio, optionally substituted alkylsulfonamido, optionally substituted cycloalkylsulfonamido, optionally substituted amino, optionally substituted amido, optionally substituted heterocyclyl, optionally substituted heteroaryl, and optionally substituted aryl; and m is 1, 2, 3, or 4.

In certain embodiments, the invention relates to any one of the aforementioned compounds, wherein $R^5$ is selected from the group consisting of

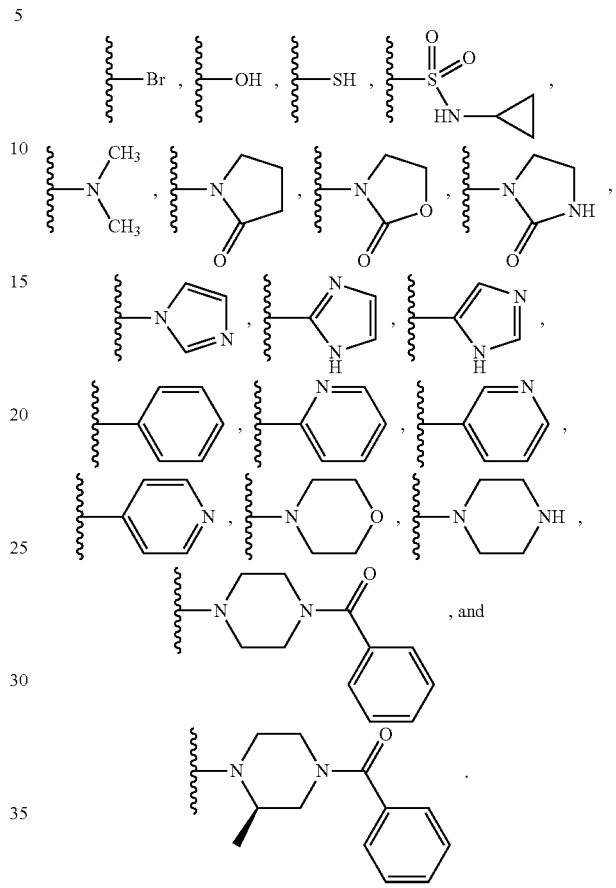

In certain embodiments, the invention relates to any one of the aforementioned compounds, wherein m is 1 or 2.

In certain embodiments, the invention relates to any one of the aforementioned compounds, wherein m is 1.

In certain embodiments, the invention relates to a compound selected from the group consisting of

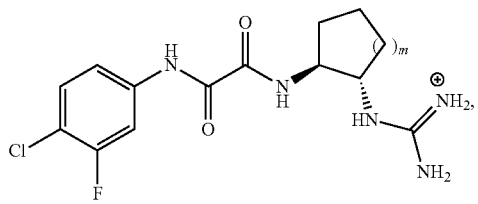

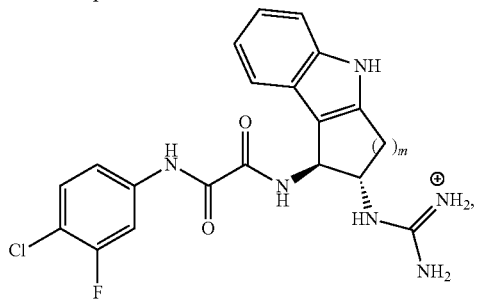

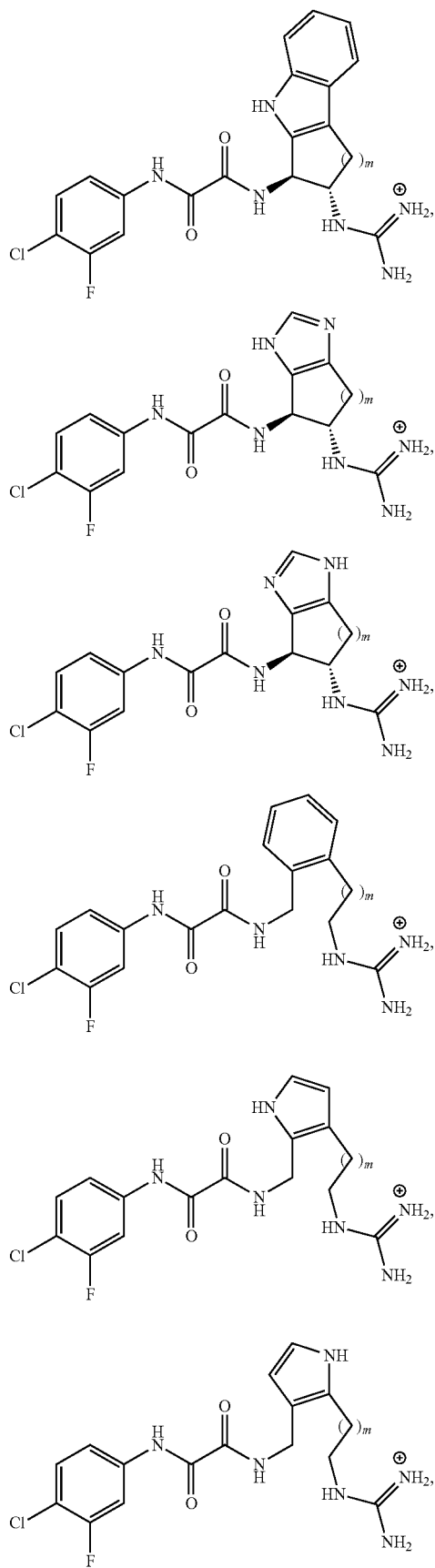

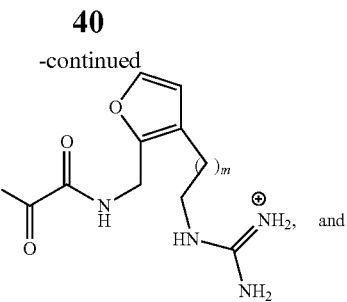

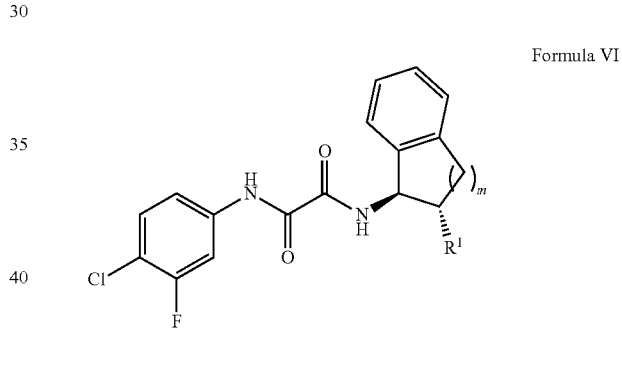

wherein m is 1, 2, 3, or 4.

In certain embodiments, the invention relates to any one of the aforementioned compounds, wherein m is 1 or 2.

In certain embodiments, the invention relates to any one of the aforementioned compounds, wherein m is 1.

In certain embodiments, the invention relates to a compound of Formula VI

Formula VI

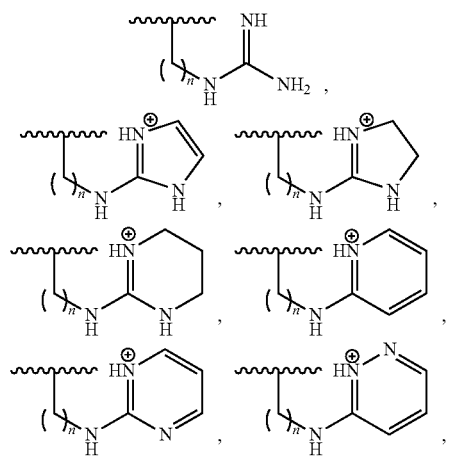

or a pharmaceutically acceptable salt or solvate thereof, wherein, independently for each occurrence, $R^1$ is selected from the group consisting of optionally substituted amino, -continued

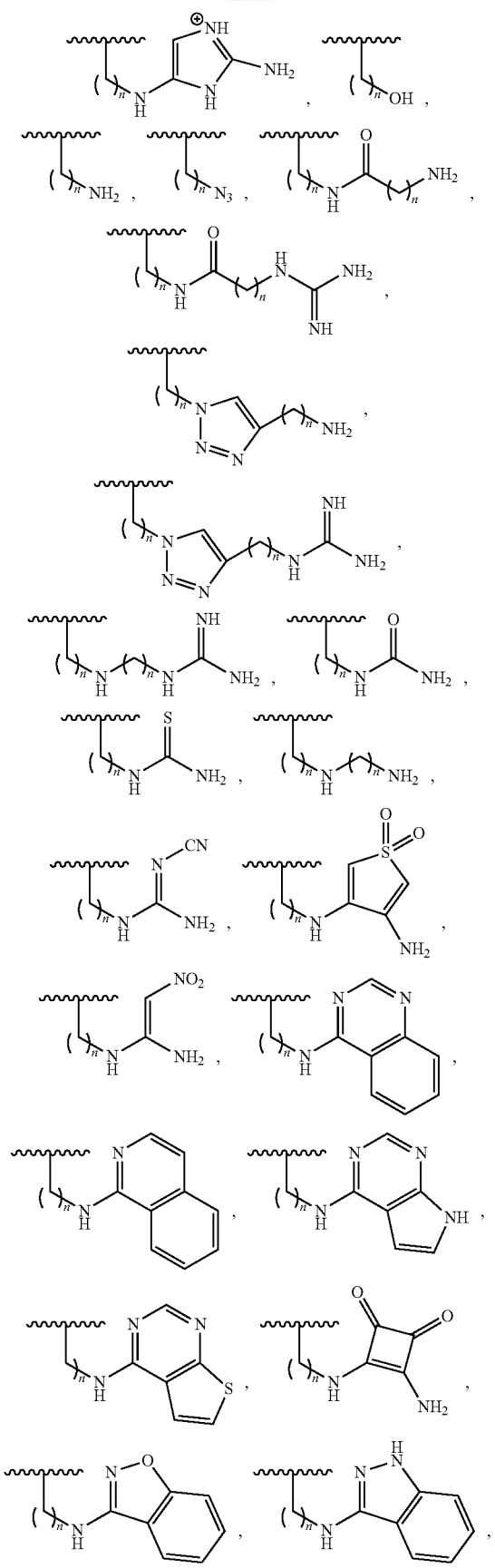
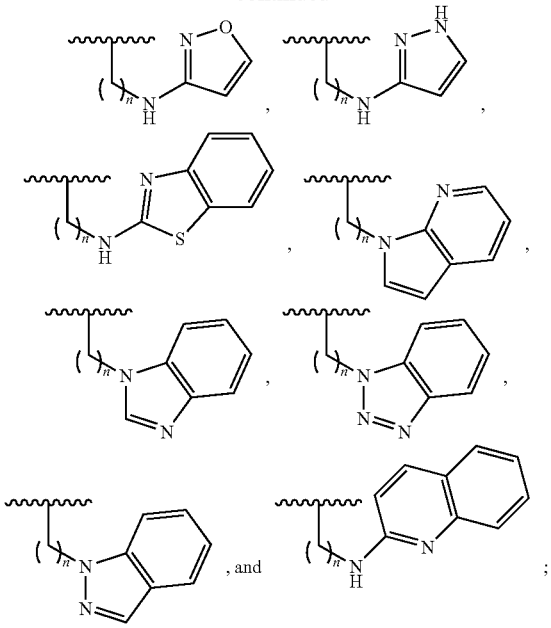

m is 1, 2, 3, or 4; and
n is 0, 1, 2, 3, 4, or 5.

In certain embodiments, the invention relates to any one of the aforementioned compounds, wherein m is 1 or 2.

In certain embodiments, the invention relates to any one of the aforementioned compounds, wherein m is 1.

In certain embodiments, the invention relates to any one of the aforementioned compounds, wherein n is 0, 1, or 2.

In certain embodiments, the invention relates to any one of the aforementioned compounds, wherein n is 1.

In certain embodiments, the invention relates to a compound of Formula VIII

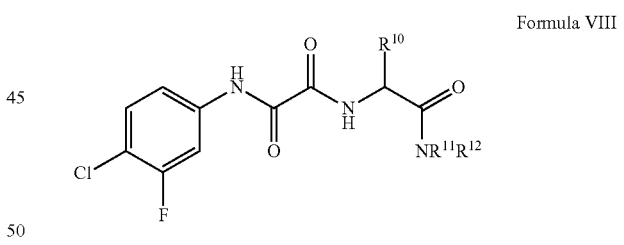

Formula VIII or a pharmaceutically acceptable salt or solvate thereof, wherein, independently for each occurrence, $R^{10}$ is optionally substituted aryl, optionally substituted heteroaryl, optionally substituted cycloalkyl, optionally substituted heterocycloalkyl, optionally substituted alkyl, or optionally substituted alkenyl;

$R^{11}$ is —H, optionally substituted alkyl, optionally substituted alkenyl, optionally substituted alkynyl, optionally substituted aryl, or optionally substituted heteroaryl; and $R^{12}$ is optionally substituted alkyl, optionally substituted alkenyl, optionally substituted alkynyl, optionally substituted aryl, or optionally substituted heteroaryl.

In certain embodiments, the invention relates to any one of the aforementioned compounds, wherein $R^{10}$ is selected from the group consisting of:

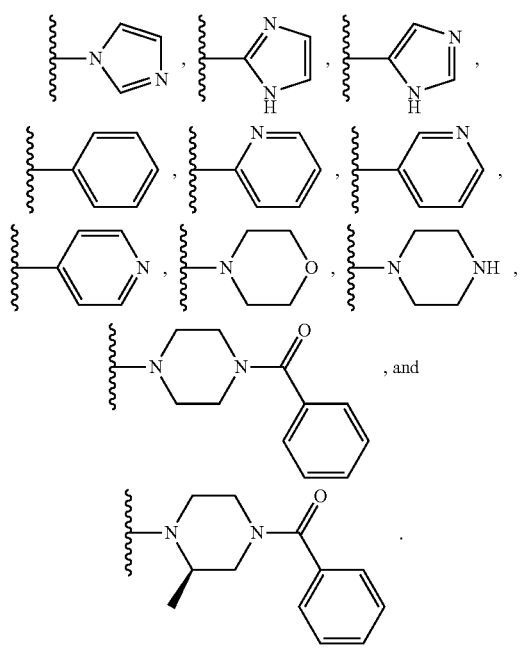

In certain embodiments, the invention relates to any one of the aforementioned compounds, wherein $R^{11}$ is —H or optionally substituted alkyl.

In certain embodiments, the invention relates to any one of the aforementioned compounds, wherein $R^{12}$ is optionally substituted alkyl.

In certain embodiments, the invention relates to any one of the aforementioned compounds, wherein the compound has the following structure:

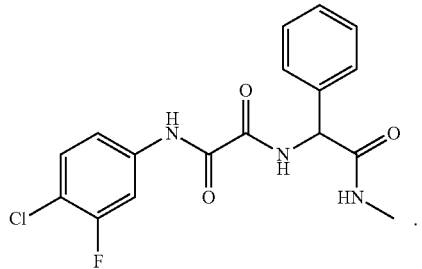 [SMILES: CNC(=O)C(NC(=O)C(=O)Nc1ccc(Cl)c(F)c1)c1ccccc1]

In certain embodiments, the invention relates to a compound selected from the group consisting of

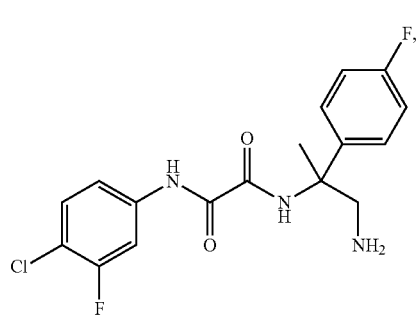

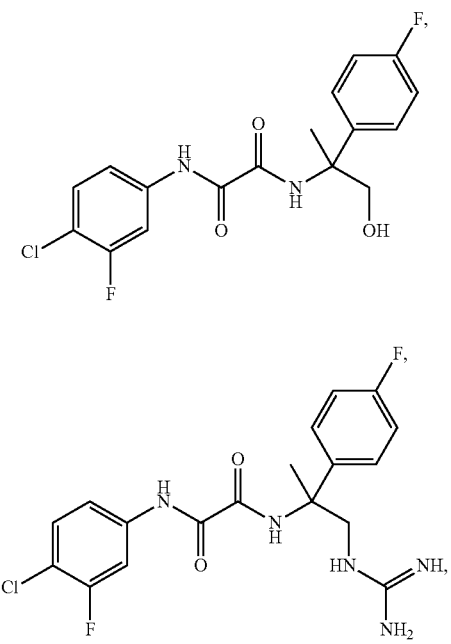

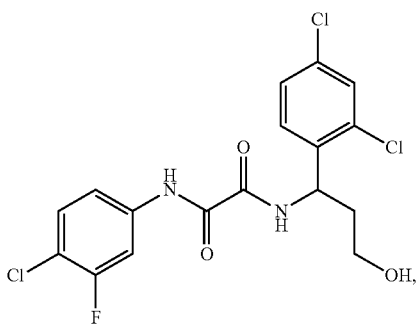

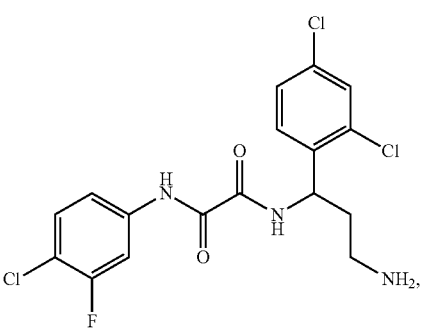

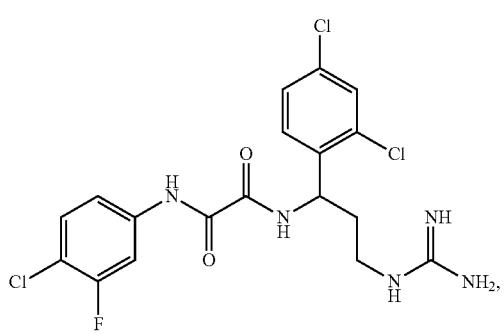

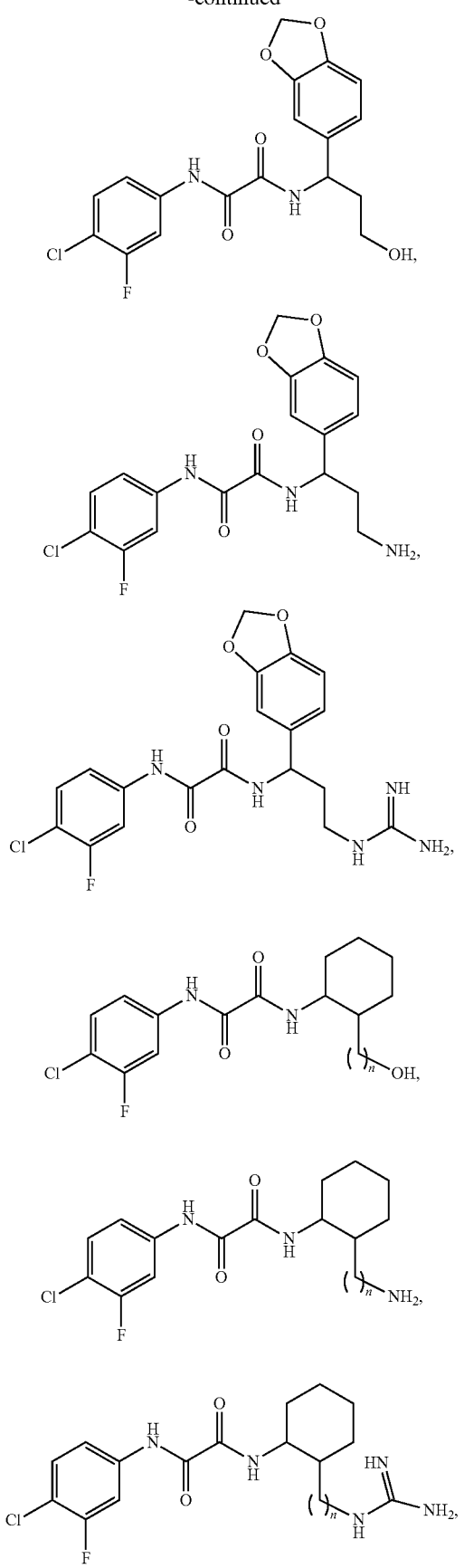
wherein n is 0, 1, 2, 3, 4, or 5.
In certain embodiments, the invention relates to any one of the aforementioned compounds, wherein n is 0, 1, or 2.

In certain embodiments, the invention relates to any one of the aforementioned compounds, wherein n is 1.

In certain embodiments, the invention relates to any one of the aforementioned compounds, wherein the compound is a single enantiomer.

Exemplary Methods

In certain embodiments, the invention relates to a method of activating HIV exterior envelope glycoprotein gp120 comprising the step of: contacting HIV with an effective amount of any one of the aforementioned compounds. In certain embodiments, the invention relates to a method of activating HIV exterior envelope glycoprotein gp120 comprising the step of: contacting HIV with an effective amount of a compound according to any one of Formulae I-VIII.

In certain embodiments, the invention relates to a method of inhibiting transmission of HIV to a cell comprising the step of: contacting HIV with an effective amount of any one of the aforementioned compounds, thereby inhibiting transmission of HIV to said cell. In certain embodiments, the invention relates to a method of inhibiting transmission of HIV to a cell comprising the step of: contacting HIV with an effective amount of a compound according to any one of one of Formulae I-VIII, thereby inhibiting transmission of HIV to said cell.

In certain embodiments, the invention relates to a method of inhibiting the progression of HIV infection in a cell comprising the step of: contacting HIV with an effective amount of any one of the aforementioned compounds, thereby inhibiting progression of HIV in the cell. In certain embodiments, the invention relates to a method of inhibiting the progression of HIV infection in a cell comprising the step of: contacting HIV with an effective amount of a compound according to any one of Formulae I-VIII, thereby inhibiting progression of HIV in the cell.

In certain embodiments, the invention relates to a method of inhibiting the transmission or progression of HIV to a cell comprising the steps of:

contacting HIV with an effective amount of any one of the aforementioned compounds; and contacting HIV with an effective amount of an exogenous ligand mimicking the chemokine receptor expressed on said cell.

In certain embodiments, the invention relates to a method of inhibiting the transmission or progression of HIV to a cell comprising the steps of:

contacting HIV with an effective amount of a compound according to any one of Formulae I-VIII and contacting HIV with an effective amount of an exogenous ligand mimicking the chemokine receptor expressed on said cell.

In certain embodiments, the invention relates to any one of the aforementioned methods, wherein the compound binds to the HIV exterior envelope glycoprotein gp120.

In certain embodiments, the invention relates to any one of the aforementioned methods, wherein said chemokine receptor is selected from CCR5 and CXCR4.

In certain embodiments, the invention relates to any one of the aforementioned methods, wherein the HIV is HIV-1 or HIV-2.

In certain embodiments, the invention relates to any one of the aforementioned methods, wherein the compound interacts with gp120 Phe43. In certain embodiments, the invention relates to any one of the aforementioned methods, wherein the compound interacts with gp120 Asp368. In certain embodiments, the invention relates to any one of the aforementioned methods, wherein the compound interacts with gp120 Phe43 and gp120 Asp368.

In certain embodiments, the invention relates to any one of the aforementioned methods, wherein the cell is CD4-negative and CCR5-positive; and the compound does not efficiently activate HIV infection of the cell.

Exemplary Pharmaceutical Compositions

While it is possible for compounds of the present invention to be administered as the raw chemical, it is also possible to present them as a pharmaceutical formulation. Accordingly, the present invention provides a pharmaceutical formulation comprising a compound or a pharmaceutically acceptable salt, prodrug or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients can be used as suitable and as understood in the art; e.g., in Remington's Pharmaceutical Sciences. The pharmaceutical compositions of the present invention can be manufactured in a manner that is itself known, e.g., by means of conventional mixing, dissolving, granulating, dragee-making, levigating, emulsifying, encapsulating, entrapping or compression processes, for example.

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route depends upon for example the condition and disorder of the recipient. The formulations can conveniently be presented in unit dosage form and can be prepared by any of the methods well known in the art. All methods include the step of bringing into association a compound of the present invention or a pharmaceutically acceptable salt, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders, inert diluents, or lubricating, surfaceactive or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, bacteriostats and solutes which render the formulation isotonic with the blood of the intended recipient; and aqueous and non-aqueous sterile suspensions which can include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions.

In addition to the formulations described previously, the compounds of the present invention can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compounds can also be formulated in rectal compositions such as suppositories or retention enemas, e.g., containing conventional suppository bases such as cocoa butter, polyethylene glycol, or other glycerides. The compounds can also be formulated in vaginal compositions as gels, suppositories, or as dendrimers conjugates. Compounds of the present invention can be administered topically, that is by non-systemic administration. Formulations suitable for topical administration include liquid or semi-liquid preparations suitable for penetration through the skin such as gels, liniments, lotions, creams, ointments or pastes.

Gels for topical or transdermal administration of compounds of the present invention can include a mixture of volatile solvents, nonvolatile solvents, and water. The volatile solvent component of the buffered solvent system can include lower (C1-C6) alkyl alcohols, lower alkyl glycols and lower glycol polymers. In certain embodiments, the volatile solvent is ethanol. The volatile solvent component is thought to act as a penetration enhancer, while also producing a cooling effect on the skin as it evaporates. The nonvolatile solvent portion of the buffered solvent system is selected from lower alkylene glycols and lower glycol polymers. In certain embodiments, propylene glycol is used. The nonvolatile solvent slows the evaporation of the volatile solvent and reduces the vapor pressure of the buffered solvent system. The amount of this nonvolatile solvent component, as with the volatile solvent, is determined by the pharmaceutical compound or drug being used. When too little of the nonvolatile solvent is in the system, the pharmaceutical compound can crystallize due to evaporation of volatile solvent, while an excess will result in a lack of bioavailability due to poor release of drug from solvent mixture. The buffer component of the buffered solvent system can be selected from any buffer commonly used in the art; in certain embodiments, water is used. There are several optional ingredients which can be added to the topical composition. These include, but are not limited to, chelators and gelling agents. Appropriate gelling agents can include, but are not limited to, semisynthetic cellulose derivatives (such as hydroxypropylmethylcellulose) and synthetic polymers, and cosmetic agents.

Lotions or liniments for application to the skin can also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They can be made by mixing the active ingredient in finely-divided or powdered form, alone or in solution or suspension in an aqueous or non-aqueous fluid, with the aid of suitable machinery, with a greasy or non-greasy base. The base can comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation can incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, can also be included.

EXEMPLIFICATION

This invention is further illustrated by the following examples, which should not be construed as limiting.

Example 1

Molecular Design and Synthesis

Analysis of the crystal structure of TS-II-224 (2) (FIG. 1) and NBD-556 bound to gp120 provided the opportunity to design small-molecule interactions with the Asp368$_{120}$ hotspot in the vestibule of the Phe43 cavity. Kwon, Y. D., et al.

Figure 5A:
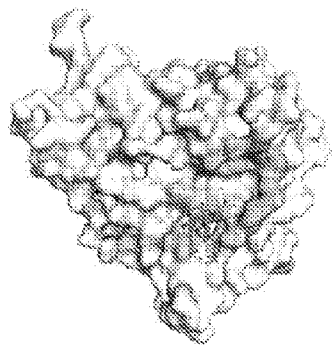
FIG. 5 depicts the structures of TS-II-224 (2), AWS-I-50 (8), AWS-I-169 (9), or DMJ-I-228 (10) bound gp120 core$_{e\ (H375S)}$ and comparisons with the CD4-bound structure. (a) Superposition of all four compounds bound at the Phe43 cavity on gp120. (b) DMJ-I-228 (10) and (c) AWS-I-169 (9) with four ordered water molecules in 2Fo-Fc electron density maps contoured at 1.2 σ. (d) TS-II-224 (2). (e) AWS-I-50 (8). (f) Hydrogen bonding network between the guanidinium group of DMJ-I-228 (10) and D368$_{gp120}$ mediated by water molecules, (g) Hydrogen bonding network between the guanidinium group of AWS-I-169 (9) and D368$_{gp120}$ mediated by water molecules, (h) CD4 and gp120 binding interface. (i) Superposition of CD4 β-turn with indene ring of DMJ-I-228 (10) and water molecules (dots).
Figure 5B:
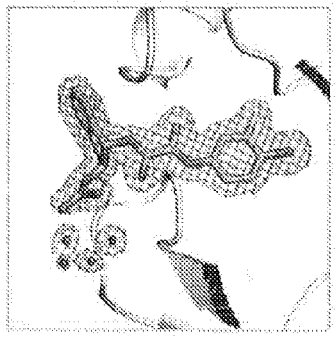
Figure 5C:
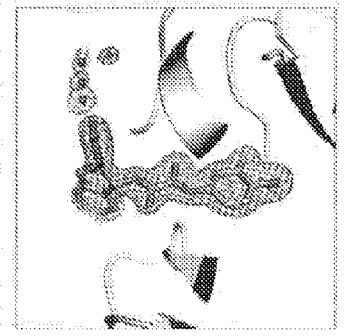
Figure 5D:
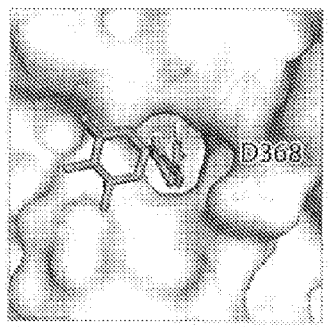
Figure 5E:
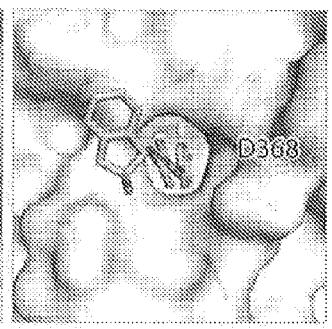
Figure 5F:
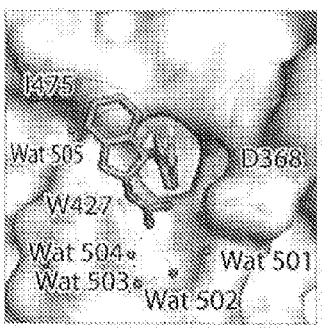
Figure 5G:
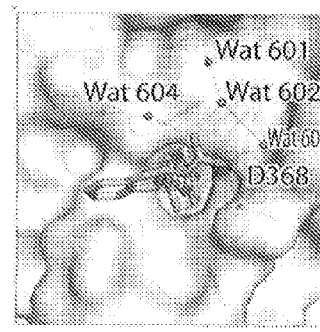
Figure 5H:
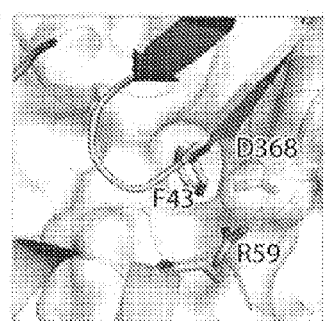
Figure 5I:
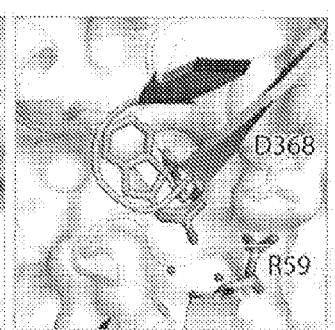
Figure 6A:
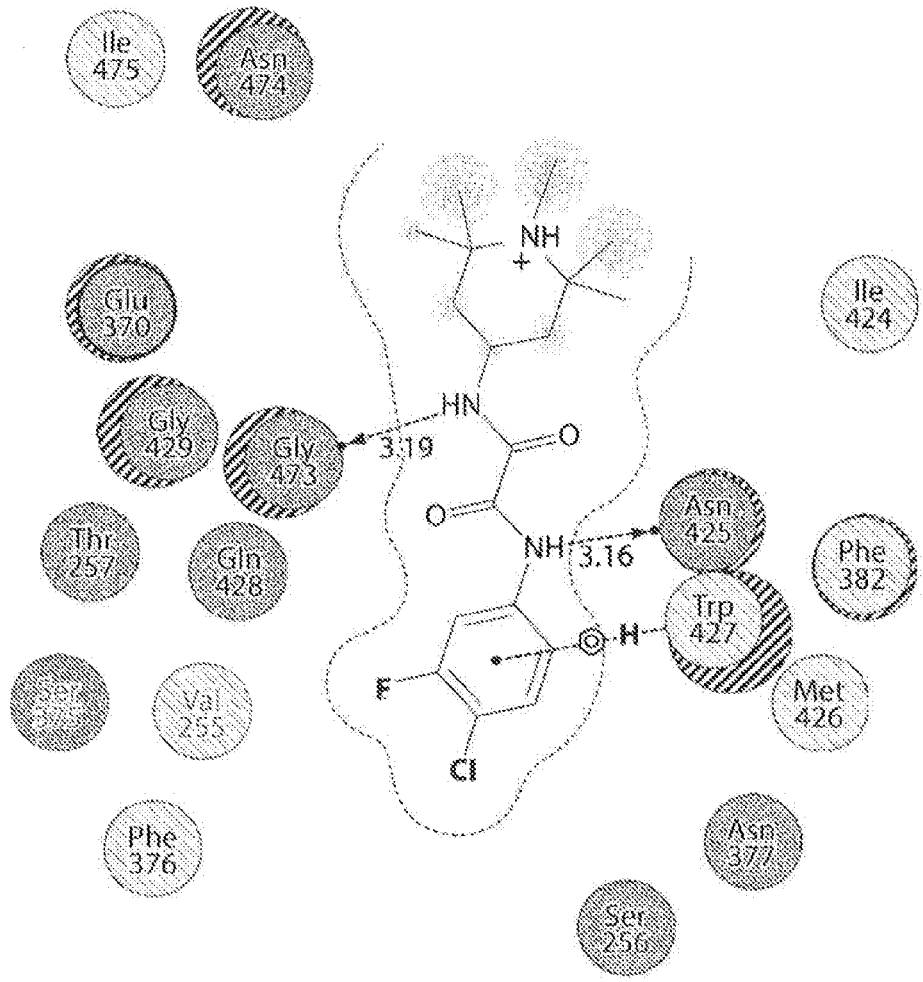
FIG. 6 depicts ligand-gp120 interaction maps: (a) TS-II-224 (2), (b) AWS-I-50 (8), (c) AWS-I-169 (9), and (d) DMJ-I-228 (10). (e) Atom numbering for DMJ-I-228. (f) Legend for protein-ligand interactions calculated and rendered with MOE ligand interaction utility.
Figure 6B:
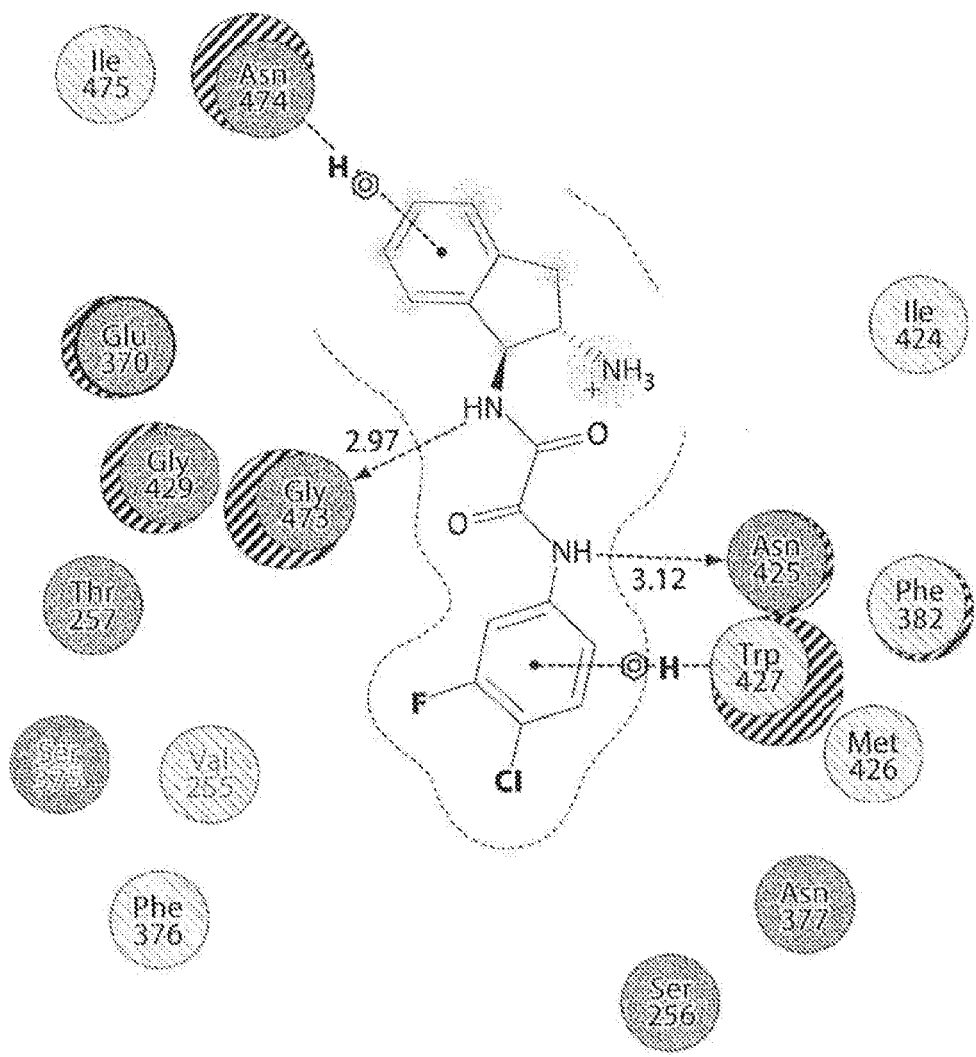
Figure 6C:
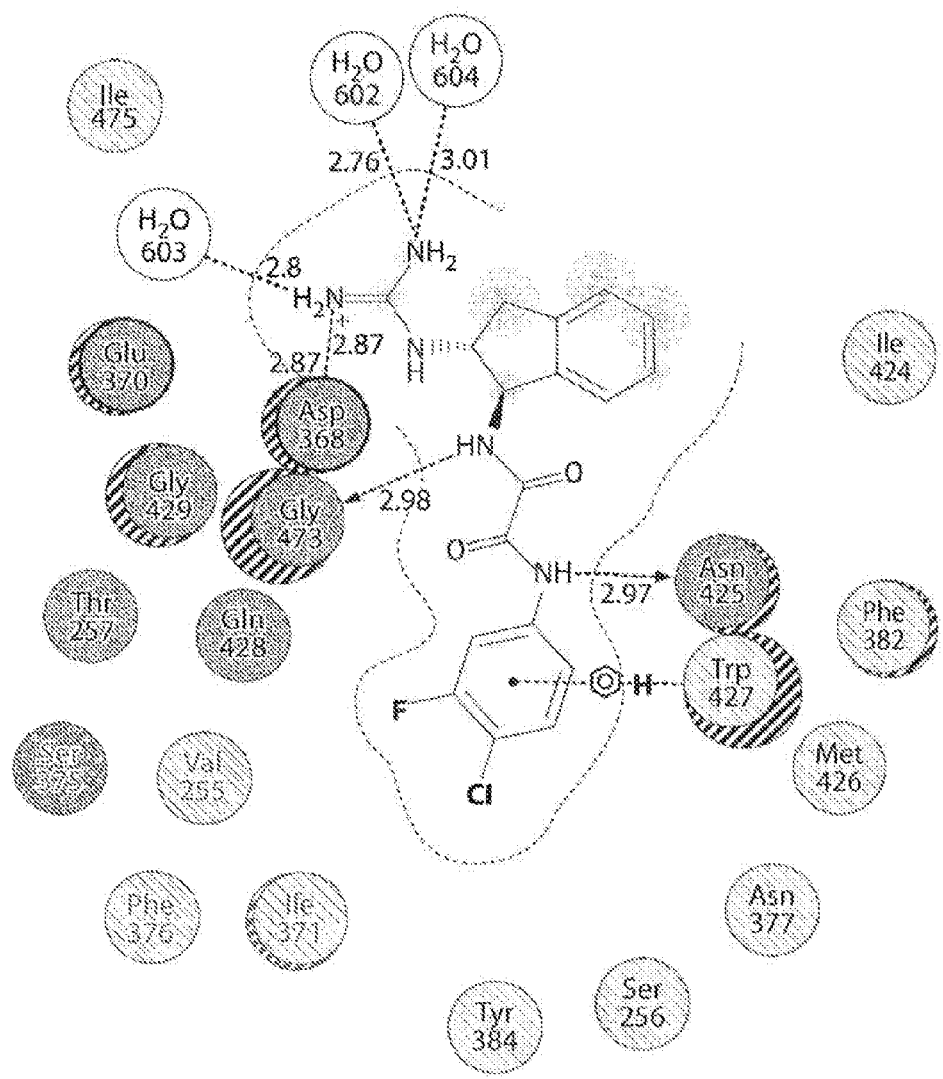
Figure 6D:
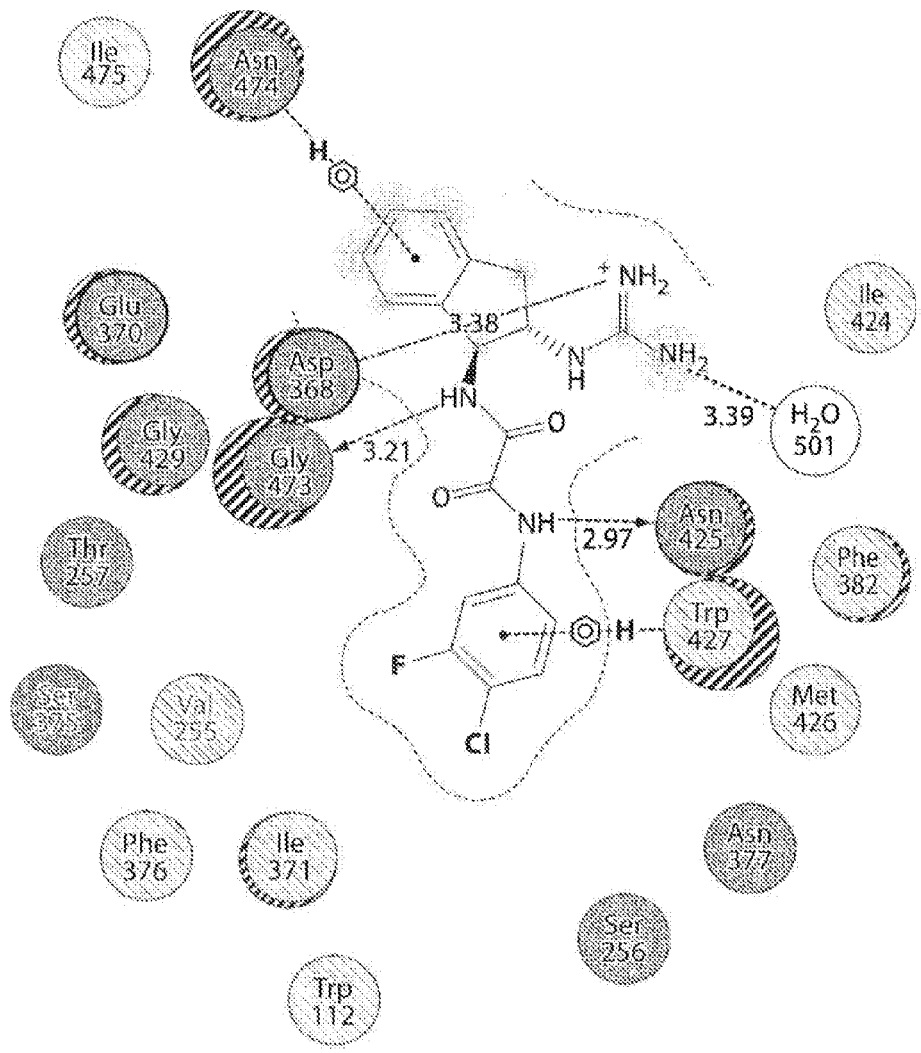
Figure 6E:
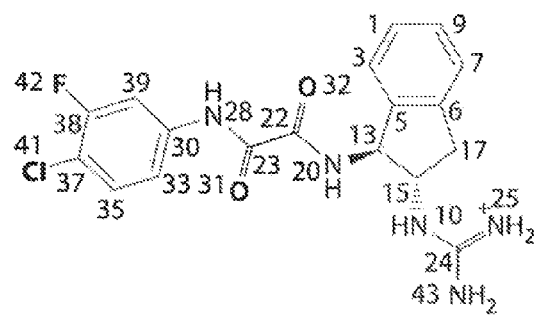
Figure 6F:
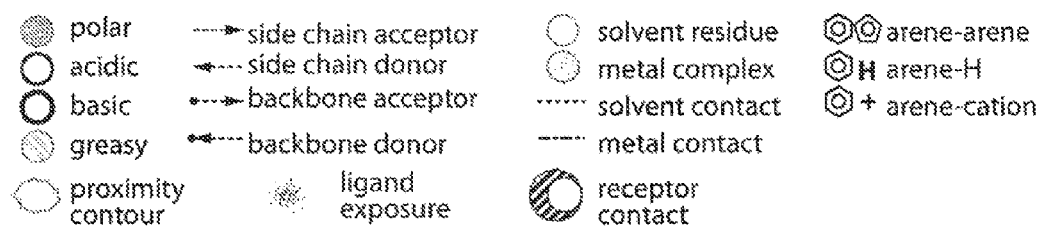

Submitted to PNAS (2011). The TS-II-224 crystal structure (FIG. 1 and FIG. 5d) indicated the close proximity of the C4 linker on the Region III tetramethylpiperidine with the carboxylate side-chain of $Asp368_{gp120}$. Rather than performing systematic synthetic modifications of the tetramethylpiperidine moiety, a virtual screening strategy was chosen to identify a replacement moiety for Region III that would contain a basic amine oriented towards $Asp368_{gp120}$. Hence, an analogue possessing a primary amine attached to C4 of the tetramethylpiperidine was constructed in silico. While the diamine (FIG. **1*a*) is not a chemically stable entity, it was used as an archetype to replicate desired interactions. The prototype was assessed with the docking program, GOLD to provide a three-dimensional model that incorporates the desired trajectory and amino group features (FIG. 1*a*). Following previously reported paradigm of virtual screening, and exploiting the ROCS shape-based similarity algorithm, the amine prototype was employed to search the Zinc Database of commercially available compounds. A scaffold with good shape and chemotype similarity to the query prototype proved to be 7-amino-8-bicyclo[4.3.0]nonanol (FIG. 1*b*). The related 1-amino-2-indanols were also identified as attractive starting points for SAR studies, as modular synthetic methods are available to access all possible stereoisomers. Hence, GOLD docking was employed to assess the suitability of the four stereoisomers of 1,2-diaminoindane as Region III replacements. As illustrated in FIG. 1*c***, the trans-1,2-diaminoindane isomers were predicted to form weak polar interactions with $Asp368_{gp120}$ and were thus selected for synthesis.

To assess the suitability of the 1-amino-2-indanols as Region III platforms, synthetic conjugation of the four commercially available (cf. 12) stereoisomers to ethyl oxalamide (11) was performed by stirring in dioxane at reflux (FIG. 2). Biological evaluation of the resultant alcohols was determined by their capacity to inhibit viral infectivity of CD4-expressing Cf2Th-CCR5 cells. The detection of weak viral inhibition for the 1-amino-2-indanols analogues (Entries 3-4, FIG. 7) provided the impetus for further development of these compounds. The cis-1-amino-2-indanols analogues (3) and (4) were converted to the corresponding trans-amines given that the trans-1,2-diaminoindanes exhibited the requisite spatial arrangement in the docking studies. Conversion of the cis-alcohol to the trans-azide (i.e. 3→13, FIG. 2) was accomplished via tosylation of the alcohol, followed by $S_N2$ displacement of the tosylate with sodium azide. Hydrogenation of the azide employing Lindlar's catalyst provided the desired amines: AWS-I-45 (7) and AWS-I-50 (8). Although these analogues demonstrated a degree of non-specificity, not uncommon for many amines of the NBD chemotype, the transition from the alcohol to amine demonstrated an increase, albeit modest, in activity (Entries (7) and (8), FIG. 7). Encouraged by this result, the basicity of the amine was increased via synthesis of the corresponding guanidine analogues. Congeners AWS-I-45 (7) and AWS-I-50 (8) were successfully converted to AWS-I-169 (9) and DMJ-I-228 (10), respectively, using 1H-pyrazol-1-carboxamidine monohydrochloride (14). The synthesis of DMJ-I-228 (10) is illustrated in FIG. 2. AWS-I-169 (9) and DMJ-I-228 (10) were found to display significant improvements in anti-viral activity over AWS-I-45 (7) and AWS-I-50 (8), but importantly did not enhance viral infectivity in CD4 deficient cells.

Example 2

AWS-I-169 (9) and DMJ-I-228 (10) Inhibit Viral Infection and Compete with CD4

To evaluate anti-viral activity of the novel compounds, indanes analogues (3-10) and TS-II-224 (2) were first tested in mono-tropic (isolates that infect cells expressing CD4/CCR5 or CD4/CXCR4) and dual-tropic (isolates that infect cells expressing CD4/CCR5 and CD4/CXCR4) HIV-1 strains in single-round infection of recombinant HIV-1 encoding firefly luciferase. The recombinant viruses employed were pseudotyped with HIV-1 envelope glycoproteins derived from either an X4, laboratory-adapted HXBc2 isolate, or the R5, primary YU2 isolate. As a control for specificity, the viruses were pseudotyped with the envelope glycoproteins of the amphotropic murine leukemia virus (A-MLV), an unrelated retrovirus. Notably, in the case of both mono-tropic (HXBc2) and dual tropic (89.6 and KB9) viruses, AWS-I-169 (9) and DMJ-I-228 (10) inhibited entry on cells co-expressing CD4 and CXCR4 (FIG. 9 and FIG. 10) with the $IC_{50}$ ranging from 6 to 30 μM. AWS-I-169 (9) and DMJ-I-228 (10) also inhibited the entry of the YU2 and ADA viruses into DC4- and CCR5-expressing cells (FIG. 3, FIG. 9, and FIG. 10). Importantly, unlike the precursors AWS-I-45 (7) and AWS-I-50 (8) results for AWS-I-169 (9) and DMJ-I-228 (10) indicated that inhibition was completely specific to HIV-1 as the enantiomers (9 and 10) did not inhibit A-MLV entry on either cell type (FIG. 3 and FIG. 7). The non-specificity reported for congeners TK-II-52 (3), TK-II-103 (4), AWS-I-45 (7) and AWS-I-50 (8) has previously been observed for compounds belonging to the NBD chemotype, which exhibit weak antiviral activity. Furthermore, the ability of AWS-I-169 (9) and DMJ-I-228 (10) to neutralize a panel of diverse strains of HIV-1 demonstrated 100% breadth in Glade B and C compared to the weaker neutralization of NBD-556 (FIG. 9 and FIG. 10).

To examine whether the indane analogues functionally replace CD4 in cellular infection, the effects on the CD4-independent entry of HIV-1 viruses were explored. Unlike TS-II-224 (2), AWS-I-169 (9) and DMJ-I-228 (10) did not enhance entry of YU2 viruses into CD4-negative, CCR5-expressing cells (FIG. 7). The addition of a guanidinium moiety to both (7) and (8) to yield AWS-I-169 (9) and DMJ-I-228 (10) appears to modulate favorably the undesired property of enhancement of viral infectivity in CD4 deficient cells. Also evaluated—whether the lack of viral enhancement might be related to the unproductive binding of AWS-I-169 (9) and DMJ-I-228 (10)-gp120 complexes to the CCR5 receptor. SPR assessment of CCR5 antibody surrogate, 17b, binding to the gp120-ligand complexes indicated that both TS-II-224 (2) and the indane analogues (7-10) induce binding of 17b to both the monomeric core and full-length gp120. Then, the capacity of DMJ-I-228 (10) to bind within the Phe43 cavity was assessed by measuring viral inhibition in the context of the cavity filling YU2 mutant S375W. Unlike the wild-type virus, the YU2 S375W virus was completely resistant to AWS-I-169 (9) and DMJ-I-228 (10) (FIG. 9 and FIG. 10). These results indicate that AWS-I-169 (9) and DMJ-II-228 (10) inhibit HIV-1 viral entry specifically at low μM affinity against diverse strains of Glade B and C by binding within the gp120 Phe43 cavity and to a gp120 conformation recognized by the 17b antibody.

Example 3

DMJ-I-228 (10) Displays a Thermodynamic Signature Resembling Small Molecule Binding Analogue binding to full-length gp120 from the YU2 strain was next characterized by isothermal titration calorimetry to assess the enthalpic and entropic contributions to binding affinity (FIG. 7 and FIG. **3*c*). Analogue TS-II-224 (2) binds to gp120 with a $K_d$ of 0.33 μM at 25° C., FIG. 7**. Although the 1,2-diaminoindane analogues [AWS-I-45 (7) and AWS-I-50 (8)] exhibit a three-fold loss in affinity, both AWS-I-169 (9) and DMJ-I-228 (10) bind with comparable affinity to TS-II-224 (2). As previously reported, the binding of CD4 to gp120 at 25° C. is associated with an enthalpy change of −34.5 kcal/mol that is partially compensated by a large unfavorable entropy change of −79 cal/(K×mol) and a change in heat capacity ($\Delta C_p$) of −1,800 cal/(K×mol). Schön, A. et al. *Biochemistry* 45, 10973-80 (2006). Such a binding event has the thermodynamic signature that resembles protein folding, rather than binding, and is associated with the large molecular ordering of gp120 upon CD4 binding. Similar to CD4 binding, NBD-556 (1) binds to gp120 with a favorable enthalpy (−24.5 kcal/mol) balanced by a large unfavorable to entropy contribution (17.1 kcal/mol) to Gibbs energy (FIG. 7) a property previously reported to be related to the enhancement of infection of CD4 negative cells (an unwanted effect). Schön, A. et al. *Chem Biol Drug Des:* 77, 161-165 (2011). The parental compound TS-II-224 (2), with a ten-fold enhancement in binding affinity also binds with a favorable enthalpy change (−19.7 kcal/mol) that is opposed by an unfavorable entropy change (ΔS) of −37 cal/(K×mol). The indane analogue, AWS-I-169 (9) has a thermodynamic signature (ΔH=−19.4 kcal/mol and −TΔS=−10.4 kcal/mol) resembling that of TS-II-224 (2) (FIG. 3*c* and FIG. 7). The amine precursor [AWS-I-45 (7)] to AWS-I-169 (9) also has similar thermodynamic signature to TS-II-224 (2). This is in contrast to the opposing trans-isomers, AWS-I-50 (8) and DMJ-I-228 (10), both of which exhibit less unfavorable entropy contributions (−TΔS=−7.6 and −5.9 kcal/mol, respectively) compared to TS-II-224 (2), AWS-I-45 (7), and AWS-I-169 (9) (FIG. 3*c* and FIG. 7). However, as shown in FIG. 3*c* and FIG. 7, DMJ-I-228 (10) binds with an enthalpy change that is less favorable (ΔH=−14.9 kcal/mol) then TS-II-224 (2), but because the entropy change is less unfavorable [ΔS=−20 cal/(K×mol)], DMJ-I-228 (10) binds with a slightly better affinity than TS-II-224 (2). Thus as shown in FIG. 3*c* the 1R, 2R enantiomers [AWS-I-45 (7)] to AWS-I-169 (9)] have a distinct thermodynamic signature form the 1S, 2S enantiomers [AWS-I-50 (8) and DMJ-I-228 (10)]. The changes in heat capacity for the binding of TS-II-224 (2), AWS-I-169 (9) and DMJ-I-228 (10), calculated from the temperature dependence of the binding enthalpies, are −738±36, −817±15 and −398±5 cal/(K×mol), respectively (FIG. 3*d*). Thus, the thermodynamic profile of DMJ-I-228 (10), suggests it is more suitable for further optimization than AWS-I-169 (9) as DMJ-1-228 (10) exhibits a lower entropic penalty upon binding to gp120. In fact, the change in heat capacity for DMJ-I-228 (10) [ca. −400 cal/(K×mol)] approaches the expected value for the burial of a small hydrophobic molecule.

Example 4

Crystal Structures of TS-II-224 and Indane Analogues Bound to Gp120

Given the combined virological and thermodynamic properties of DMJ-I-228 (10) elucidation of gp120-indane analogues complexes by x-ray crystallography was of high interest. A 1.9 Å-resolution structure of unliganded gp120 core from the Glade A/$E_{93TH057}$ strain has been shown previously. Kwon, Y. D. et al. Submitted to PNAS (2011). The protein also produced well diffracting crystals in complex with VRC01-like antibodies. Wu, et al. *Science* 333, 1593-1602 (2011); Zhou, et al. *Science* 329, 811-817 (2010). These findings led to the use of a H375 variant of the Glade A/E protein as a template molecule for co-crystallization in complex with the small molecules that target the CD4-binding site. Crystal structures were determined in the Glade A/E $gp120_{(H375S)}$ in complex with four analogues, TS-II-224 (2), AWS-I-50 (8) AWS-I-169 (9) and DMJ-I-228 (10) at 2.0 Å, 1.8 Å, 1.8 Å, and 1.9 Å resolution, respectively, by molecular replacement (FIG. 5 and FIG. 4). To facilitate analysis of protein-ligand interactions in the context of the crystal structures, hydrogen atoms were added to all atoms within a 4.5 Å radius of the small molecule ligand and were minimized in the Merck Molecular Force Field. Two-dimensional depictions of protein-ligand interactions for the complexes are shown in FIG. 6.

TS-II-224 (2) binds in a manner similar to that observed in the 3.0 Å structure of NBD-556 complexed to Glade C gp120. Kwon, Y. D. et al. Submitted to PNAS (2011). The Region I, m-F, p-Cl phenyl group, is bound deep within the Phe43 cavity forming aromatic stacking interactions with $Phe382_{gp120}$ and $Trp427_{gp120}$ and hydrophobic contacts with $Val255_{gp120}$ and $Ile424_{gp120}$. In Region II both amide nitrogens form hydrogen bonds with main-chain carbonyls on opposite sides of the Phe43 cavity ($Gly473_{gp120}$ from the outer domain and $Asn425_{gp120}$ from the bridging sheet domain). In the cavity vestibule, one gem-dimethyl moiety of the Region III tetramethylpiperidine forms van der Waals contacts with bridging sheet domain residues $427\text{-}429_{gp120}$, while the second gem-dimethyl group contacts the outer domain residues $473\text{-}474_{gp120}$. Comparison of TS-II-224 (2) Region I and II with AWS-I-150 (8), AWS-I-169 (9) and DMJ-I-228 (10) reveals that similar interactions are observed in this portion of the gp120 cavity (FIG. 5*d*-5*g*). The RMSD for Phe43 cavity residues among the complexes is 0.39 $Å^2$ and 0.68 $Å^2$ for backbone and side-chain atoms, respectively, and as such does not imply differences in gp120 structure for the four ligand-gp120 structures. Surprisingly, in Region III, a comparable set of contacts is formed by the indane rings of AWS-I-50 (8) and DMJ-I-228 (10), as observed with the tetramethylpiperidine of TS-II-224 (2) (FIG. 5). For both AWS-I-50 (8) and DMJ-I-228 (10), the five-membered ring of the indane overlaps with the TS-II-224 (2) piperidine ring and the arene ring substitutes for one of the methyl groups, but forms more extensive contacts with outer domain residues $Gly473_{gp120}$ and $Asn474_{gp120}$ (FIG. 6*b* and FIG. 6*c*). The 2-amino group in AWS-I-50 (8) substitutes for one of the gem-dimethyl groups on the opposing face of the vestibule; thus, this 2-amino group contacts the bridging sheet but is 6.0 Å from $Asp368_{gp120}$. Superposition of the AWS-I-50 (8) and DMJ-I-228 (10) coordinates with those of the CD4-bound gp120 crystal structure (1G9M)[19] indicates that the indane rings effectively mimic the CD4 β-turn spanning the interface of the outer domain and bridging sheet (FIG. 5*i*). The indane arene ring overlaps with CD4 main-chain atoms of $Asn40_{CD4}$ and $Gly40_{CD4}$, while the five-membered ring overlaps with $Ser42_{CD4}$ and $Phe43_{CD4}$ CD4 main-chain atoms (FIG. 5*i*).

Example 5

AWS-I-169 (9) and DMJ-II-228 (10) Guanidinium Interactions with $Asp368_{gp120}$ Addition of the guanidinium group to AWS-I-50 (8) was designed to strengthen protein-ligand interactions with $Asp368_{gp120}$. Molecular dynamics studies of gp120 complexed to NBD-556 indicated enhanced dynamics along the α3-helix containing $Asp368_{gp120}$/suggesting the capacity of the $Asp368_{gp120}$ side-chain to adapt to bound ligands. Shrivastava, I. et al. *Biochemistry* 50, 4173-83 (2011). However, the four small molecule-gp120 complexes reveal that the Asp368$_{gp120}$ side-chain has the same orientation as that observed in both the CD4(PDB: 1G9M)[19] and the NBD-556-bound complexes. Interestingly, the guanidinium moiety of DMJ-I-228 (10) does not form a salt bridge with Asp368$_{gp120}$. Instead, the guanidinium group of DMJ-I-228 (10) forms an ionic interaction and hydrogen bonds with Asp368$_{gp120}$ in the gp120 complex (FIG. 6f and FIG. 6c). (The hydrogen bonding is essentially electrostatic in nature, especially at distances observed here, 3.2-4.0 Å; these are classified as weak hydrogen bonds). As the positive charge is delocalized over the guanidinium group, Nη1 (N25) and N11 (N43) atoms could contribute to hydrogen bonding, while the Nη1 (N25) interactions with Asp368$_{gp120}$ would be predominately electrostatic in nature (See FIG. 6e for atom numbering). The contribution of the guanidinium-Asp368$_{gp120}$ interaction, as judged by the measured binding affinity of $K_d$=0.25 μM compared to a $K_d$=0.30 μM for TS-II-224 (2), reflects the weak hydrogen bonding and electrostatic interactions noted above. As observed in the structure, the first hydrogen bond is an intra-molecular bond between Nη1 (N25) and oxalamide ketone (O32) of DMJ-I-228 (10); the second is between Nη1 (N25) and the Asp368 side-chain carboxylate oxygen (O∈1); a third exists between Nη (N43) and crystallographic water, Wat501. Only one Asp368$_{gp120}$ carboxylate oxygen participates in hydrogen bonding, to both the guanidinium Nη1 (N25) and Wat501. Interestingly, Wat501 is located above the Asp368$_{gp120}$ carboxylate in a position equivalent to that observed for Arg59$_{CD4}$-guanidinium in the gp120-CD4 complex (FIG. 5h). Moreover, Wat501 is at the center of a hydrogen bonding network that bridges DMJ-I-228 (10) with the outer domain and the bridging sheet. Posterior to the indane arene ring, Wat505 forms hydrogen bonds between the main-chain carbonyl of Trp427$_{gp120}$ in the bridging sheet and main-chain amine of Ile475$_{gp120}$ in the outer domain (FIG. 5f and FIG. 5g). Proximal to the guanidinium group, Wat501 hydrogen bonding extends from Wat503 to Wat504 and then to the main-chain carbonyl of Met426$_{gp120}$ residing on the bridging sheet. Only one of these water molecules, Wat504, is observed in the TS-II-224-gp120 complex.

Figure 7:
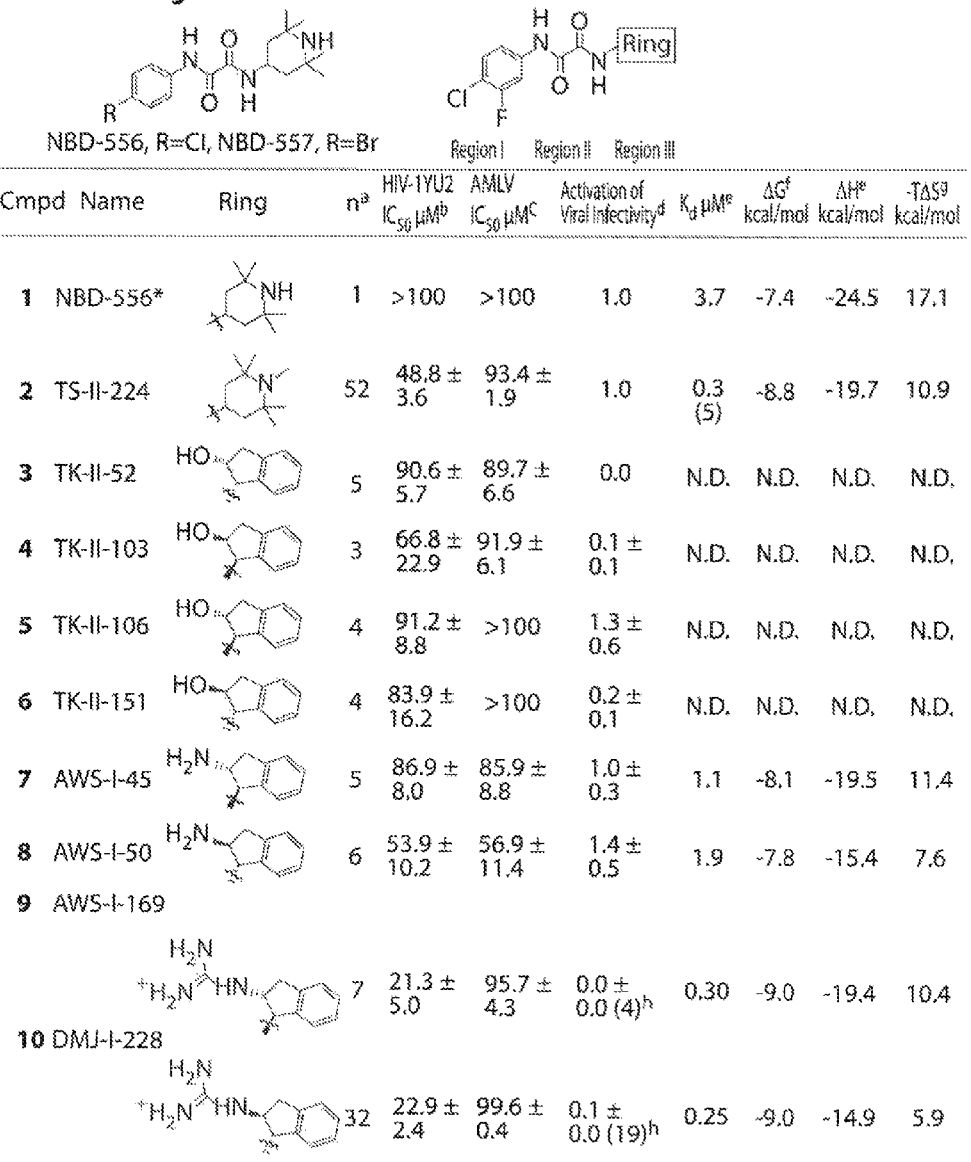
FIG. 7 tabulates various indane analogs of the invention. [a]Each compound was assayed in triplicate and is reported as a mean for one experiment. For multiple experiments the means and standard deviations are reported. The number of times independent experiments were performed is indicated by n. [b]The compound concentrations that inhibited 50% of virus infection ($IC_{50}$) was determined by infecting Cf2Th-CD4/CCR5 cells with 10,000 RT units of wild-type HIV-1$_{YU2}$ virus expressing luciferase with increasing concentrations of the compound. [c]The compound concentrations that inhibited 50% of virus infection ($IC_{50}$) when assayed against viruses with the ampotrophic murine leukemia virus (A-MLV) envelop glycoproteins. [d]Activation of viral infectivity was determined by infecting Cf2Th-CCR5 cells with recombinant HIV-1$_{YU2}$ in the presence of NBD analogues. The luciferase activity in the target cells incubated with each compound was divided by that in the cells incubated with TS-II-224 (2) to obtain the relative activation of infectivity. [e]The dissociation constant ($K_d$) and the change in enthalpy ($\Delta H$) were determined at 25° C. by isothermal titration calorimetry using a high-precision VP-ITC titration calorimetric system from MicroCal/GE Healthcare (Northampton, Mass., USA). The calorimetric cell (approximately 1.4 mL), containing gp120 from the YU2 strain dissolved in PBS (Roche Diagnostics GmbH, Mannheim, Germany), pH 7.4 with 2% DMSO, was titrated with the different inhibitors dissolved in the same buffer. The concentration of gp120 was approximately 2 μM, and inhibitor at a concentration of 80-130 μM was added in aliquots of 10 μL until saturation was reached (usually in 20-30 injections). [f]The change in Gibbs energy ($\Delta G$) was calculated from the affinity according to the relation $\Delta G=RT\ln K_a$, where $K_a$ is the association constant ($K_a=1/K_d$), R is the gas constant (1.987 cal/(K×mol)), and T is the absolute temperature in kelvin. [g]$T\Delta S$ was calculated from the relation $\Delta G=\Delta H-T\Delta S$. *Data for NBD556 as reported in Schön, A. et al. *Biochemistry* 45, 10973-80 (2006) and Madani, N. et al. *Structure* 16, 1689-701 (2008). [h]The number of experiments for activation of viral infectivity is indicated in parentheses.

To investigate further the dual hotspot interaction, crystals of the enantiomer of DMJ-I-228 (10), AWS-I-169 (9) (FIG. 7), was prepared. The 1.8 Å structure of AWS-I-169 (9)-gp120 complex shows that the indane ring is rotated 90 degrees in the cavity vestibule relative to Region II, and thus the plane of the ring is tilted away from the gp120 surface (FIG. 5g). Hence, the arene ring does not form contacts with the outer domain Gly473$_{120}$ and Asn474$_{gp120}$ residues, as observed with AWS-I-50 (8) and DMJ-I-228 (10) (FIG. 6). The altered orientation of the indane ring results from the opposite stereochemistry for the trans-1,2 disubstituted indane (FIG. 7). Thus, as a consequence of stereochemistry, the AWS-I-169 (9) guanidinium group approaches Asp368$_{gp120}$ from the opposite orientation. Nonetheless, the guanidinium group forms a strong hydrogen bonded/electrostatic interaction with the Asp368$_{gp120}$ carboxylate (FIG. 5g). A network of ordered water molecules also surrounds the guanidinium group, Wat601, Wat602, Wat603, and Wat604, forming a bridging hydrogen-bonding network between the Gly472$_{gp120}$ main-chain carbonyl and Asp368$_{gp120}$ amide nitrogen in the outer-domain. Only one of these waters, Wat601, is observed in any of the other complexes, DMJ-I-228 (10), suggesting that the pattern of ordered water molecules is dependent on the position of the guanidinium group. Hence, in the AWS-I-169 (9)-gp120 complex, ordered water forms a bridging hydrogen bonded network between the ligand and the outer domain, whereas in DMJ-I-228 (10) the guanidinium-water hydrogen bonding network spans both the bridging sheet domain and outer domain. Thus, the distinct thermodynamic signatures of the 1S, 2S versus the 1R, 2R indane enantiomers is consistent with the distinct binding modes revealed in the crystal structures of AWS-I-169 (9) and DMJ-I-228 (10).

Example 6

Small Molecule Modeling

Molecules were constructed in MOE (MOE Molecular Operating Environment Chemical Computing Group, version 2005.06 (Montreal, Canada) (http//www.chemcomp.com), ionized using MOE's WashMDB function, and hydrogens were added (Chemical Computing Group, 2010). The small molecule conformation was minimized to a gradient of 0.01 in the MMFF94× (Halgren, 1999a, b) force field using a distance-dependent dielectric constant of 1.

Example 7

Protein Modeling

Protein modeling. Using the X-ray crystal structure of the NBD-557 bound to HIV-1 gp120 core and antibody 48d, hydrogen atoms were added and tautomeric states and orientations of Asn, Gln and His residues were determined with Molprobity (Lovell et al., 2003; Word et al., 1999). Hydrogens were added to crystallographic waters using MOE (2010). The OPSLAA (Jorgensen et al., 1996) force field in MOE was used and all hydrogens were minimized to an rms gradient of 0.01, holding the remaining heavy atoms fixed. A stepwise minimization followed for all atoms, using a quadratic force constant (100) to tether the atoms to their starting geometries; for each subsequent minimization, the force constant was reduced by a half until 0.25. This was followed by a final cycle of unrestrained minimization.

GOLD (version 4.0.1) (Jones et al., 1997; Verdonk et al., 2003). The binding site was defined by using the crystallographic position of NBD-557. Docking calculations were performed with crystallographic water molecules, 41 and 142 in the cavity vestibule. One hundred genetic algorithm (GA) docking runs were performed with the following parameters: initialvirtual_ptmatch_max=3.5, diverse solutions=1, divsol_cluster_size=1, and divsol_rmsd=1.5. All other parameters were set as defaults.

Example 8

ROCS Virtual Screening

Flipper from Open Eye was used to expand compounds with unspecified chirality prior to generation of conformers. Using Omega (version 2.2.1) (Bostrom et al., 2003) from Open Eye with default parameters, a maximum of 50 low energy conformers for all compounds in the Zinc Database (version 7) (Irwin and Shoichet, 2005; Zinc, 2006) were generated and stored in sd files of approximately 10,000 molecules. ROCS (2008; Rush et al., 2005) searches were run using 3D coordinates from the docked binding mode of the amine containing teramethypiperidine prototype. The Implicit Mills Dean (Mills and Dean, 1996) force field was used to match chemotypes as well as shape. A maximum of 2000 hits were saved for each query and were ranked by a combination of Tanimoto and the scaled Color Score (ComboScore). Primary amines were selected from the set of hits, filtered for currently commercial availability, conjugated in silico and were docked with GOLD (Jones et al., 1997; Verdonk et al., 2003) and scored with a mass-corrected Goldscore.

Example 9

Synthetic Procedures

All reactions were conducted in oven-dried glassware under an inert atmosphere of nitrogen or argon, unless otherwise stated. All solvents were reagent or high performance liquid chromatography (HPLC) grade. Anhydrous $CH_2Cl_2$ and THF were obtained from the Pure Solve™ PS-400 system under an argon atmosphere. All reagents were purchased from commercially available sources and used as received. Microwave heating was conducted with a Biotage Initiator system equipped with an autosampling arm, in either 0.5-2.0 mL or 2.0-5.0 mL sealed reaction vials. Reactions were magnetically stirred under an argon atmosphere, unless otherwise noted and reactions were monitored by either thin layer chromatography (TLC) with 0.25 mm E Merck pre-coated silica gel plates or analytical high performance liquid chromatography (HPLC). Yields refer to chromatographically and spectroscopically pure compounds. Optical rotations were measured on a JASCO P-2000 polarimeter. Proton and carbon-13 NMR spectra were recorded on a Bruker AM-500 at 305 K, unless otherwise noted. Chemical shifts are reported relative to chloroform ($\delta$ 7.26), methanol ($\delta$ 3.31), or dimethyl sulfoxide ($\delta$ 2.50) for $^1$H NMR and either chloroform ($\delta$ 77.0), methanol ($\delta$ 49.2), or dimethyl sulfoxide ($\delta$ 39.4). High-resolution mass spectra (HRMS) were recorded at the University of Pennsylvania Mass Spectroscopy Service Center on either a VG Micromass 70/70H or VG ZAB-E spectrometer. Analytical HPLC was performed with a Waters HPLC-MS system, consisting of a 515 pump and Sunfire C18 reverse phase column (20 µL injection volume, 5 µm packing material, 4.5×50 mm column dimensions) with detection accomplished by a Micromass ZQ mass spectrometer and 2996 PDA detector. Preparative scale HPLC was preformed with a Gilson 333/334 preparative pump system equipped with a 5 mL injection loop, Sunfire C18 OBD column (5 µm packing material, 19×100 mm column dimensions) equipped with a UV-Vis dual wavelength (210 and 254 nm) detector and 215 liquid handling module. Solvent systems employed were based on the following buffers: Buffer A: $H_2O$ containing 0.05% formic acid; Buffer B: MeCN containing 0.05% formic acid. The purity of new compounds was judged by NMR and LCMS (>95%).

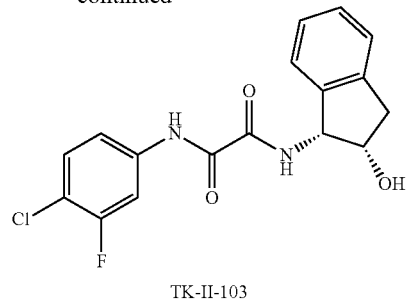

TK-II-103

$N^1$-(4-chloro-3-fluorophenyl)-$N^2$-((1R,2S)-2-hydroxy-2,3-dihydro-1H-inden-1-yl)oxalamide (TK-II-103)

To a solution containing ethyl 2-(4-chloro-3-fluorophenylamino)-2-oxoacetate (1) (1.73 g, 7.05 mmol) in 20 mL dioxane in a round-bottom flask was added (1R,2S)-1-amino-2,3-dihydro-1H-inden-2-ol (1.16 g, 7.76 mmol) and both a stir bar and a reflux condenser were equipped. The reaction was heated to reflux for 72 hours and then allowed to cool to room temperature. The crude reaction mixture was concentrated in vacuo. The solid was collected by filtration with a 1:1 mixture of hexanes and dichloromethane to give 2.04 g (83%) of TK-II-103 as an off-white flakey solid; $[\alpha]^{29}_D=-112.1°$ (c=0.48, DMSO): $^1$H NMR (500 MHz, DMSO-d$_6$) $\delta$ 11.19 (s, 1H), 8.36 (d, J=8.7 Hz, 1H), 7.97, (dd, J=2, 11.7 Hz, 1H), 7.77, (d, J=8.8 Hz, 1H), 7.59, (t, J=8.7 Hz, 1H), 7.28-7.18, (m, 4H), 5.46, (d, J=4.9 Hz, 1H), 5.25, (dd, J=5.2, 8.6 Hz, 1H), 4.52, (dd, J=4.6, 8.6 Hz, 1H), 3.14, (dd, J=4.9, 16.2 Hz, 1H), 2.88, (d, J=16.1 Hz, 1H); $^{13}$C NMR (125 MHz, DMSO-d$_6$) $\delta$ 159.3, 158.8, 156.8, (d, $J_{CF}$=242.5 Hz), 141.0, 140.8, 138.2, (d, $J_{CF}$=10 Hz), 131.6, 127.7, 126.5, 125.0, 124.1, 117.5 (d, $J_{CF}$=2.9 Hz), 114.5 (d, $J_{CF}$=17.5 Hz), 108.6, (d, $J_{CF}$=25 Hz), 71.6, 56.9. HRMS (ES+) m/z 371.0572 [(M+Na)$^+$; calcd for $C_{17}H_{14}ClFN_2O_3$: 371.0575].

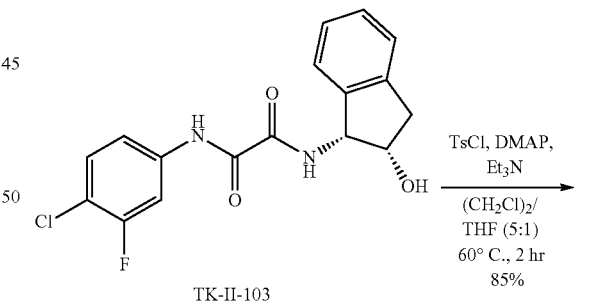

TK-II-103

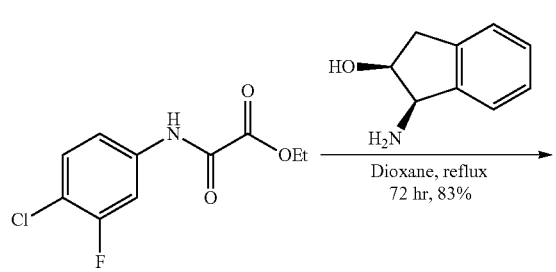

1

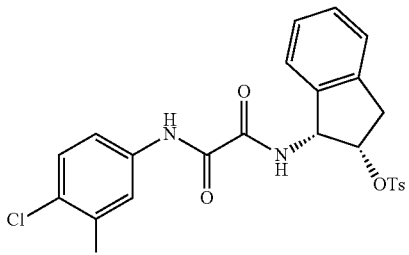

TK-II-105

1R,2S)-1-(2-((4-chloro-3-fluorophenyl)amino)-2-oxoacetamido)-2,3-dihydro-1H-inden-2-yl 4-methyl-benzenesulfonate (TK-II-105

To a solution containing TK-II-103 (0.98 g, 2.82 mmol) in a mixture of dichloroethane (25 mL) and THF (5 mL) was added p-toluene sulfonyl chloride (1.61 g, 8.46 mmol), followed by NEt$_3$ (1.18 mL, 8.46 mmol), DMAP (0.3446 g, 2.82 mmol), and a stir bar. A reflux condenser was attached and the solution was heated to 60° C. and stirred for 2 hours. After cooling, the reaction mixture was quenched with 50 mL of saturated NH$_4$Cl solution and then extracted with EtOAc (3×100 mL). The combined organic fractions were dried over MgSO$_4$, filtered, and then concentrated in vacuo. The crude product was purified by silica gel column chromatography (Hexanes/EtOAc/NEt$_3$ 10/1/0.01 to 1/1/0.01) to give 1.2 g (85%) of TK-II-105 as a white flakey solid; $[\alpha]_D^{25}=-8.9°$ (c=0.27, CH$_2$Cl$_2$); $^1$H NMR (500 MHz, DMSO-d$_6$) δ 10.97 (s), 8.84 (d, J=9.0 Hz, 1H), 8.00 (dd, J=2.5, 12.0 Hz, 1H), 7.79 (dd, J=2.0, 9.0 Hz, 1H), 7.75 (d, J=8 Hz, 2H), 7.62 (t, J=8.5 Hz, 1H), 7.33-7.22 (m, 6H), 5.49 (dd, J=5.0, 8.5 Hz, 1H), 5.24 (dt, J=1.5, 5.0 Hz, 1H), 3.34 (m, overlap with water, 1H), 3.13 (d, J=16.0 Hz, 1H), 2.33 (s, 3H); $^{13}$C NMR (125 MHz, DMSO-d$_6$) δ 159.4, 157.9, 156.8 (d, J$_{CF}$=243.8 Hz), 144.8, 138.7, 138.6, 138.2, (d, J$_{CF}$=10 Hz), 132.7, 130.6, 129.9, 128.3, 127.5, 127.0, 124.8, 123.9, 117.3, (d, J$_{CF}$=2.7 Hz), 114.4, (d, J$_{CF}$=17.5 Hz), 108.4, (d, J$_{CF}$=25.0 Hz), 82.7, 55.6, 37.6, 20.9. HRMS (ES+) m/z 503.0862 [(M+H); calcd for C$_{24}$H$_{20}$ClFN$_2$O$_5$S: 503.0844].

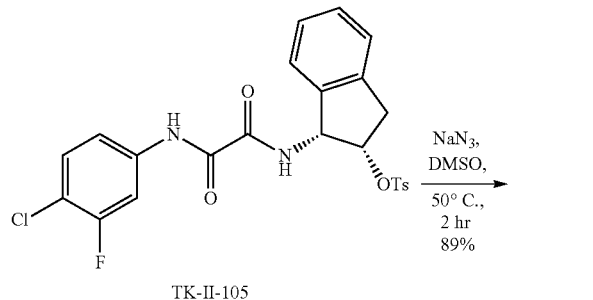

TK-II-105

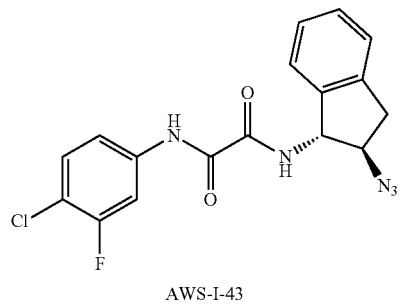

AWS-I-43

N$^1$-((1R,2R)-2-azido-2,3-dihydro-1H-inden-1-yl)-N$^2$-(4-chloro-3-fluorophenyl)oxalamide (AWS-I-43)

To a solution of TK-II-105 (208 mg, 0.42 mmol) in 4 mL DMSO was added NaN$_3$ (135 mg, 2.08 mmol) and a stir bar. The solution was heated to 50° C. and stirred for 2 hours. After cooling to room temperature, the solution was quenched with H$_2$O (20 mL) and then extracted with EtOAc (3×50 mL). The combined organic fractions were washed with brine (3×50 mL), dried over Na$_2$SO$_4$, and then filtered. The organic layer was concentrated in vacuo and the crude product was then purified by silica gel chromatography (Hexanes/EtOAc/NEt$_3$ 5/1/0.01 to 3/1/0.01). to give 138 mg (89%) of the azide AWS-I-43 as a white flakey solid; $[\alpha]_D^{25}=-34.9°$ (c=0.30, EtOAc): $^1$H NMR (500 MHz, DMSO-d$_6$) δ 11.14 (s, 1H), 9.66 (d, J=9.0 Hz, 1H), 7.98 (dd, J=2.0, 11.5 Hz, 1H), 7.77 (dd, J=1.5, 8.5 Hz, 1H), 7.60 (t, J=8.5 Hz, 1H), 7.28-7.22 (m, 3H), 7.15 (d, J=7.0 Hz, 1H), 5.34 (t, J=8.0 Hz, 1H), 4.54 (q, J=8.0 Hz, 1H), 3.34 (dd, J=7.5, 15.5 Hz, 1H), 2.88 (dd, J=8.5, 15.5 Hz, 1H); $^{13}$C NMR (125 MHz, DMSO-d$_6$) δ 160.1, 158.5, 156.8, (d, J$_{CF}$=242.5 Hz), 139.9, 138.8, 138.2 (d, J$_{CF}$=10 Hz), 130.5, 128.2, 127.1, 124.7, 123.4, 117.4, (d, J$_{CF}$=3.0 Hz), 114.4, (d, J$_{CF}$=17.8 Hz), 108.5, (d, J$_{CF}$=25.6 Hz), 65.7, 59.4, 35.3. HRMS (ES+) m/z 372.0652 [(M−H)$^-$; calcd for C$_{17}$H$_{12}$ClFN$_5$O$_2$: 372.0664].

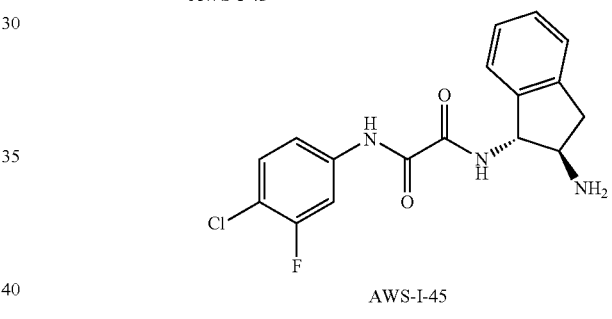

AWS-I-45

N$^1$-((1R,2R)-2-amino-2,3-dihydro-1H-inden-1-yl)-N$^2$-(4-chloro-3-fluorophenyl)oxalamide (AWS-I-45)

To a solution of AWS-I-43 (80 mg, 0.21 mmol) in 6 mL MeOH was added Lindlar's catalyst (5% Pd/CaCO$_3$, poisoned with lead, 40 mg, 0.02 mmol) and a stir bar. Hydrogen was bubbled through the solution, after which the reaction mixture was stirred for 2 hours under a hydrogen atmosphere at room temperature. The reaction mixture was then filtered through a plug of celite and the filtrate was concentrated in vacuo to obtain the crude product, which was then purified by silica gel chromatography (DCM/MeOH/NH$_4$OH 95/5/0.1) to give 46 mg (62%) of the amine AWS-I-45 as a white flakey solid; $[\alpha]_D^{25}=-83.2°$ (c 0.16. MeOH); $^1$H NMR (500 MHz, CDCl3): δ 11.07 (s, 1H), 9.22 (d, J=9.0 Hz, 1H), 7.98 (dd, J=2.4, 11.9 Hz, 1H), 7.77 (ddd, J=1.0, 2.5, 8.9 Hz, 1H), 7.60 (t, J=8.7 Hz, 1H), 7.20-7.14 (m, 3H), 7.06 (d, J=7.2 Hz, 1H), 5.00 (t, J=8.5 Hz, 1H), 3.69 (q, J=8.5 Hz, 1H), 3.08 (dd, J=7.5 Hz, 1H), 2.64 (dd, J=9.2 Hz, 1H); $^{13}$C NMR (125 MHz, DMSO-d$_6$) δ 160.3, 159.0, 156.8, (d, J$_{CF}$=242.5 Hz), 142.0, 140.6, 138.3 (d, J$_{CF}$=10 Hz), 130.6, 127.4, 126.4, 124.4, 123.3, 117.3, (d, J$_{CF}$=3.75 Hz), 114.2, (d, J$_{CF}$=17.5 Hz), 108.4 (d, J$_{CF}$=25 Hz), 62.6, 59.6, 48.6. HRMS (ES+) m/z 348.0911 [(M+H)$^+$; calcd for C$_{17}$H$_{15}$ClFN$_3$O$_2$: 348.0915].

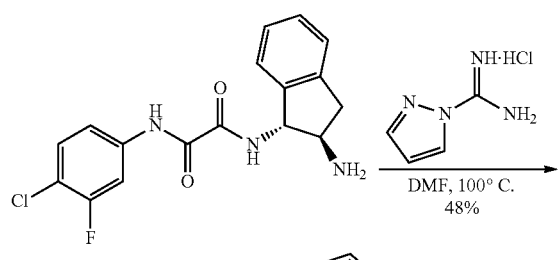

AWS-I-45

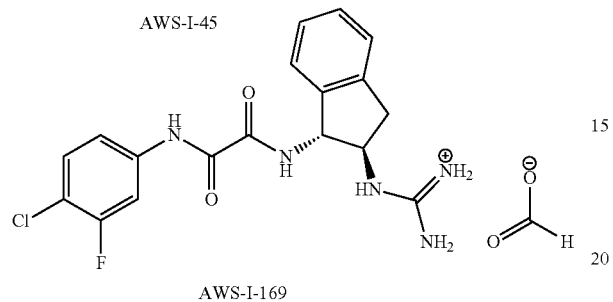

AWS-I-169

Amino(((1R,2R)-1-(2-((4-chloro-3-fluorophenyl)amino)-2-oxoacetamido)-2,3-dihydro-formate (AWS-I-169)

To a solution containing AWS-I-45 (16 mg, 0.047 mmol) in 1 mL DMF was added 1H-pyrazole-1-carboxamidine hydrochloride (13.9 mg, 0.095 mmol), N,N-diisopropylethylamine, (41 μL, 0.237 mmol) and a stir bar. The solution was heated to 100° C. for 16 hours and then allowed to cool. The light-red reaction mixture was diluted with 1.5 mL of MeCN/H$_2$O (1:1) and purified by HPLC to give 9 mg (48%) of AWS-I-169 as a clear amorphous solid; $[\alpha]_D{}^{25}=-3.2°$ (c=0.72, MeOH) $^1$H NMR (500 MHz, CD$_3$OD): δ 8.3 (br s, 1H$_{formate}$), 7.84 (dd J=2.5, 11.5 Hz, 1H), 7.50 (d, J=8.75 Hz, 1H), 7.43 (t, J=8.5 Hz, 1H)), 7.34-7.29 (m, 4H), 5.27 (d, J=4.5 Hz, 1H), 4.30 (m, 1H), 3.52 (dd, J=7.5 Hz, 1H), 2.93 (dd, J=5, 16.5 Hz, 1H); $^{13}$C NMR (125 MHz, CD$_3$OD) δ 162.8, 159.4, 159.3, (d, J$_{CF}$=244.4 Hz), 159.0, 141.9, 139.7, 139.1 (d, J$_{CF}$=9.8 Hz), 131.9, 130.6, 129.0, 126.4, 126.3, 118.3 (d, J$_{CF}$=3.3 Hz), 117.4 (d, J$_{CF}$=17.8 Hz), 110.0 (d, J$_{CF}$=26.3 Hz), 62.3, 59.7, 37.8. HRMS (ES+) m/z 390.1132 [(M+H)$^+$; calcd for C$_{18}$H$_{18}$ClFN$_5$O$_2$: 390.1133].

The enantiomers of TK-II-103, TK-II-105, AWS-I-43, AWS-I-45, and AWS-I-169 (TK-II-52, AWS-I-48, AWS-I-49, AWS-I-50, and DMJ-I-228, respectively) were generated in a similar fashion and have identical spectra as the referenced spectra vide supra. The observed optical rotations for these enantiomers are:

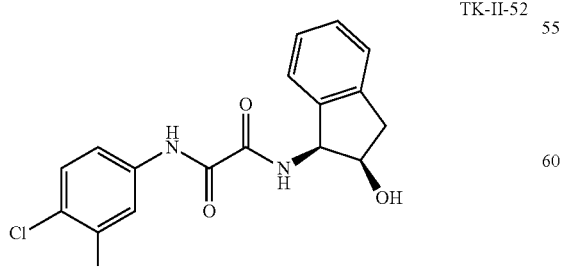

TK-II-52

$[\alpha]_D{}^{29} = +103.5°$ (c = 0.56, DMSO)

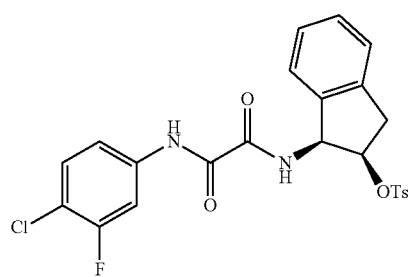

AWS-I-48

$[\alpha]_D{}^{25} = +10.4°$ (c = 0.29, CH$_2$Cl$_2$)

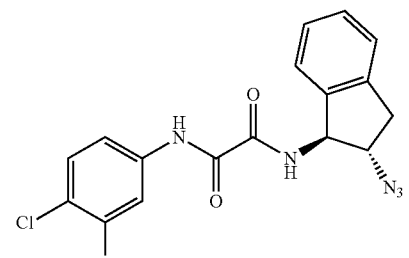

AWS-I-49

$[\alpha]_D{}^{25} = +40.7°$ (c = 0.51, EtOAc)

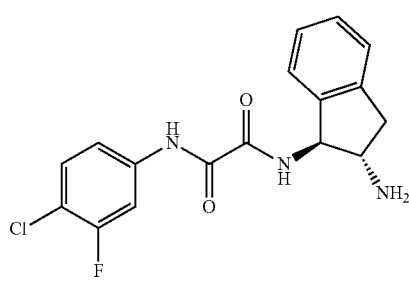

AWS-I-50

$[\alpha]_D{}^{25} = +93.0°$ (c = 0.14, MeOH)

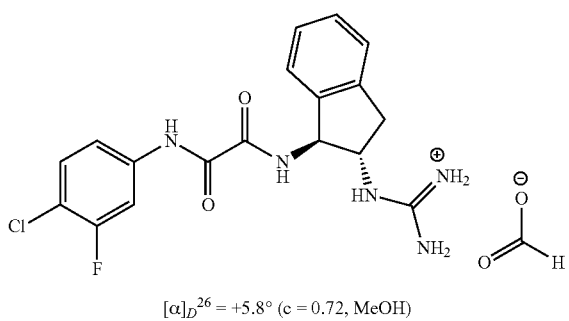

DMJ-I-228

$[\alpha]_D{}^{26} = +5.8°$ (c = 0.72, MeOH)

Example 10

Cell-Based Infectivity Assays

General Considerations

Compounds were dissolved in dimethyl sulfoxide (DMSO), and stored at 10 mM concentrations at −20° C. The compounds were diluted in Dulbecco Modified Eagle Medium (DMEM, Invitrogen) to create 1 mM solutions before use. Soluble CD4 (sCD4) was purchased from ImmunoDiagnostics (Woburn, Mass.). Human 293T embryonic kidney and canine Cf2Th thymocytes (ATCC) were grown at 37° C. and 5% CO$_2$ in DMEM (Invitrogen) containing 10% fetal bovine serum (Sigma) and 100 μg/mL of penicillin-streptomycin (Meditech, Inc.). Cf2Th cells stably expressing human CD4 and either CCR5 or CXCR4 (Babcock et al., 2001, Mirzabekov et al., 1999) were grown in medium supplemented with 0.4 mg/mL of G418 (Invitrogen) and 0.20 mg/mL of hygromycin B (Roche Diagnostics). Using the Effectene transfection reagent (Qiagen), 293T human embryonic kidney cells were cotransfected with plasmids expressing the pCMVΔP1ΔenvpA HIV-1 Gag-Pol packaging construct, the wild-type or mutant HIV-1$_{YU2}$ envelope glycoproteins or the envelope glycoproteins of the control amphotropic murine leukemia virus (A-MLV), and the firefly luciferase-expressing vector at a DNA ratio of 1:1:3 μg. For the production of viruses pseudotyped with the A-MLV glycoprotein, a rev-expressing plasmid was added. The single-round, replication-defective viruses in the supernatants were harvested 24-30 hours after transfection, filtered (0.45 μm), aliquoted, and frozen at −80° C. until further use. The reverse transcriptase (RT) activities of all viruses were measured as described previously (Rho et al., 1981).

Assay of Virus Infectivity and Drug Sensitivity

Cf2Th/CD4-CCR5 or Cf2Th/CD4-CXCR4 target cells were seeded at a density of 6×10$^3$ cells/well in 96-well luminometer-compatible tissue culture plates (Perkin Elmer) 24 h before infection. On the day of infection, (1 to 100 μM) was added to recombinant viruses (10,000 reverse transcriptase units) in a final volume of 50 μL and incubated at 37° C. for 30 minutes. The medium was removed from the target cells, which were then incubated with the virus-drug mixture for 2-4 hours at 37° C. At the end of this time point, complete medium was added to a final volume of 150 μL and incubated for 48 hours at 37° C. The medium was removed from each well, and the cells were lysed with 30 μL of passive lysis buffer (Promega) by three freeze-thaw cycles. An EG&G Berthold Microplate Luminometer LB 96V was used to measure luciferase activity in each well after the addition of 100 μL of luciferin buffer (15 mM MgSO$_4$, 15 mM KPO$_4$ [pH 7.8], 1 mM ATP, 1 mM dithiothreitol) and 50 μL of 1 mM D-luciferin potassium salt) (BD Pharmingen).

Example 11

Isothermal Titration Calorimetry

Isothermal titration calorimetric experiments were performed using a high-precision VP-ITC titration calorimetric system from MicroCal LLC. (Northampton, Mass.). The calorimetric cell (~1.4 mL), containing gp120 at a concentration of about 2 μM dissolved in PBS, pH 7.4 (Roche Diagnostics GmbH), with 2% DMSO, was titrated with the different compounds dissolved in the same buffer at concentrations of 80-130 μM. The compound solution was added in aliquots of 10 μL at pre-set intervals. All solutions were degassed to avoid any formation of bubbles in the calorimeter during stirring. All experiments were performed at 25° C. The heat evolved upon injection of compound was obtained from the integral of the calorimetric signal. The heat associated with the binding reaction was obtained by subtracting the heat of dilution from the heat of reaction. The individual binding heats were plotted against the molar ratio, and the values for the enthalpy change (ΔH) and association constant, $K_a$ ($K_d$=1/$K_a$), were obtained by nonlinear regression of the data.

Example 12

Plasmids

A point mutation was introduced to pVRC8400-HIV-1 Glade A/E$_{93TH057}$ ΔV123 expression vector to generate Glade A/E$_{93TH057}$ gp120 core$_e$ (H375S)-expressing plasmid. The plasmid construct was verified by DNA sequencing.

Example 13

Surface Plasmon Resonance

SPR measurements were performed using Biacore T100 (GE Healthcare) at 25° C. NBD556-hexylamine (manuscript submitted) was immobilized on a CM5 chip (~6.5 RU) using amine-coupling chemistry. Clade A/E$_{93TH057}$gp120 core$_e$ and gp120 core$_e$(H375S) were injected over the chip from 5 to 0.63 μM in two-fold dilutions at a flow rate of 40 μL/min. HBS-EP buffer (10 mM HEPES, 150 mM NaCl, 3 mM EDTA, and 0.05% surfactant P20, pH 7.4, GE Healthcare) was used as the running buffer. To assess the enhancement of monomeric gp120 binding to CD4i antibody, 17b by binding of small molecules, we immobilized anti-human IgG (Fc) antibody (GE Healthcare, Human Antibody Capture Kit) on a CM5 chip and captured 17b IgG at a density of ~400 RU. YU2 gp120 core$_m$ or full-length gp120 (200 nM) with 0 to 100 μM of each compound in HBS-EP buffer with 0.1% P-20 and 5% DMSO were passed over the chip at a flow rate of 40 μL/min. The running buffer contained 10 mM HEPES, 150 mM NaCl, pH 7.4, 3 mM EDTA, 0.1% surfactant P20, and 5% DMSO.

Example 14

Crystallization, Data Collection, Structure Determination, and Refinement

Clade A/E$_{93TH057}$gp120 core$_e$(H375S) was purified as described (manuscript submitted). Small molecules in 100% DMSO were incorporated in the purified gp120 to make a final concentration of 100 μM. Then, the gp120: small molecule complexes were set up for crystallization using vapor diffusion at 20° C. Crystals grew in a mixture of 0.5 μL protein-small molecule complex and 0.5 μL of reservoir solution containing 8-10% (v/v) PEG 8000, 5% iso-propanol, 0.1 M HEPES (pH 7.5). Crystals were soaked in cryo-protection solution containing 30% ethylene glycol, 12% PEG 8000, and 0.1 M HEPES (pH 7.5), and were flash frozen in liquid nitrogen. Data were collected at beamline SERCAT ID-22 at the Advanced Photon Source, and processed with HKL2000 (Otwinowski and Minor, 1977). The structure was solved by molecular replacement with PHENIX (Adams et al., 2004) using the coordinates of unliganded Glade A/E$_{93TH057}$ gp120 core$_e$ (PDB ID 3TGT). The initial Fo-Fc map generated after a rigid body refinement clearly indicated the electron densities of AWS-I-169 (9) and DMJ-I-228 (10) and allowed us to place them into the densities manually using COOT (Emsley and Cowtan, 2004). The initial densities of TS-II-224 and AWS-I-50, however, were not as clear as those found in AWS-I-169 (9) and DMJ-I-228 (10), specifically in the Region III. After several rounds of refinement using PHENIX (Adams et al., 2004), the R and values converged to 18.1-20.3% and 20.4-23.7%, respectively. The geometry of the refined model was checked with Molprobity (Davis et al., 2007). FIGS. 1 and 5 were generated by PyMOL.

Example 15

Viral Breadth Studies

Viral Stocks and Neutralization Assays

HIV-1 Env-pseudoviruses were prepared by transfecting 293T cells with 10 μg of rev/env expression plasmid and 30

μg of an env-deficient HIV-1 backbone vector (pSG3Δenv), using Fugene 6 transfection reagents (Invitrogen). Pseudovirus-containing culture supernatants were harvested two days after transfection, filtered (0.45 μm), and stored at −80° C. or in the vapor phase of liquid nitrogen. Neutralization was measured using HIV-1 Env-pseudoviruses to infect TZM-b1 cells as described previously (Li et al., 2005; Li et al., 2006; Seaman et al., 2010; Wu et al., 2009) with minor modifications. Briefly, the test reagent (DMJ-I-228, NBD556, or CD4-Ig) were diluted in complete media containing 10% DMSO. Then 40 μL of virus was added to 10 μL of serial diluted test reagent in duplicate wells of a 96-well flat bottom culture plate, and the virus-reagent mix was incubated for 30 min at 37° C. To keep assay conditions constant, sham media containing 10% DMSO was used in place of test reagent in specified control wells. The virus input was set at a multiplicity of infection of approximately 0.01-0.1, which generally results in 100,000 to 400,000 relative light units (RLU) in a luciferase assay (Promega, Madison, Wis.). The test reagent concentrations were defined at the point of incubation with virus supernatant. Neutralization curves were fit by nonlinear regression using a 5-parameter hill slope equation as previously described (Seaman et al., 2010). The 50% or 80% inhibitory concentrations (IC50 or IC80) were reported as the reagent concentrations required to inhibit infection by 50% or 80%.

Example 16

Construction of the HIV-1 Envelope Sequence Phylogenetic Trees

The HIV-1 gp160 protein sequences of isolates used in the neutralization assays were aligned using MUSCLE, for multiple sequence comparison by log-expectation (Edgar, 2004a, b). The protein distance matrix was calculated by "protdist" using the Jones-Taylor-Thornton model (Jones et al., 1992), and the dendrogram was constructed using the neighbor-joining method (Kuhner and Felsenstein, 1994) by "Neighbor". The analysis was performed at the NIAID Biocluster (https://niaid-biocluster.niaid.nih.gov/). The trees were displayed with Dendroscope (Huson et al., 2007).

Example 17

Figure 14A:
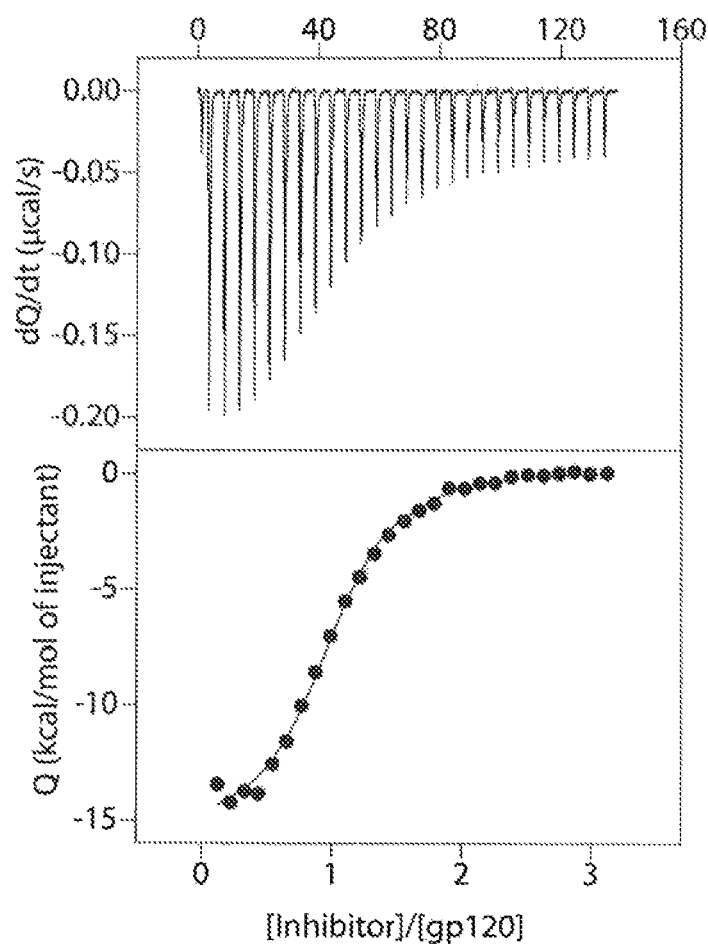
FIG. 14 depicts isothermal titration calorimetry (ITC) calorimetric titrations of gp120 with the (A) (+)-4 and (B) (−)-4 (from FIG. 13) at 25° C. The titration with the racemate (±)-4 (inset) resulted in a complex binding curve with contributions from more than one binding event.
Figure 14B:
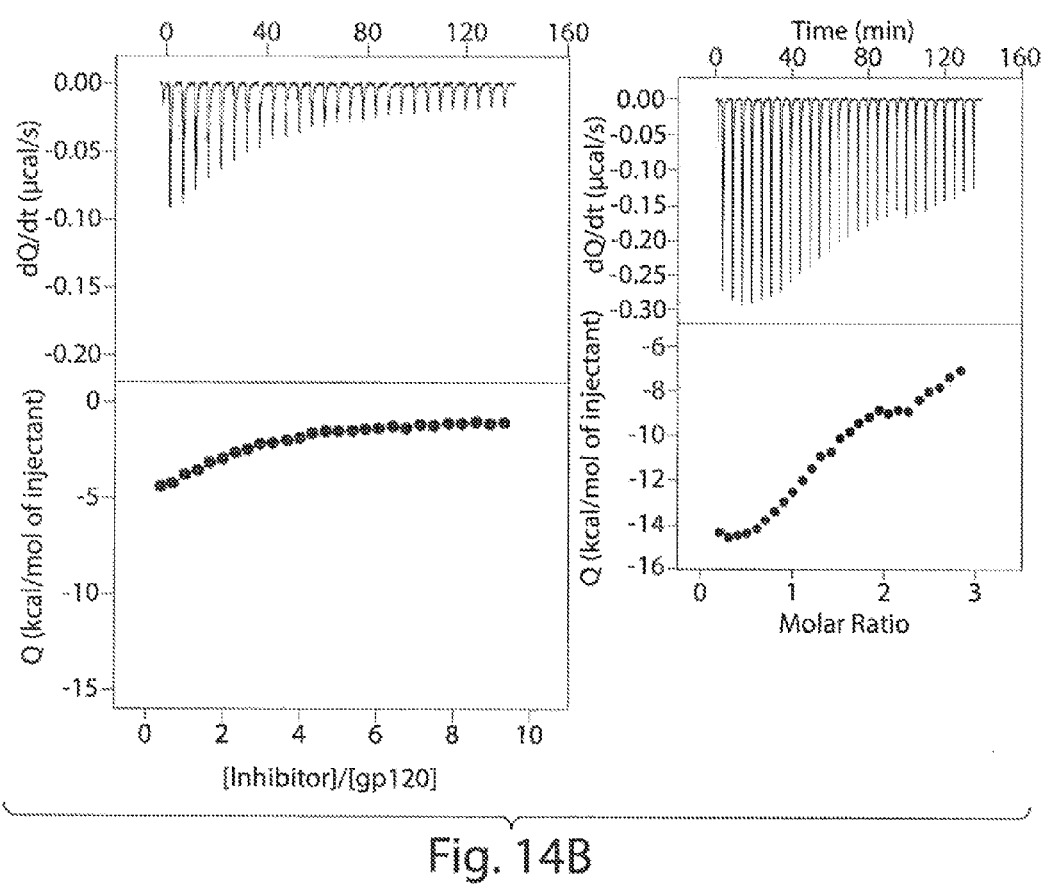

Varying the Distance Between the Trans Indane Ring System and the Guanidinium Functionality Titration of gp120 with (±)-4 employing isothermal titration calorimetry (ITC) resulted in a complex binding curve that suggested more than one binding event (FIG. 14). We reasoned that this observation was related to one enantiomer having a higher affinity within the racemic mixture (±)-4.

Figure 15:
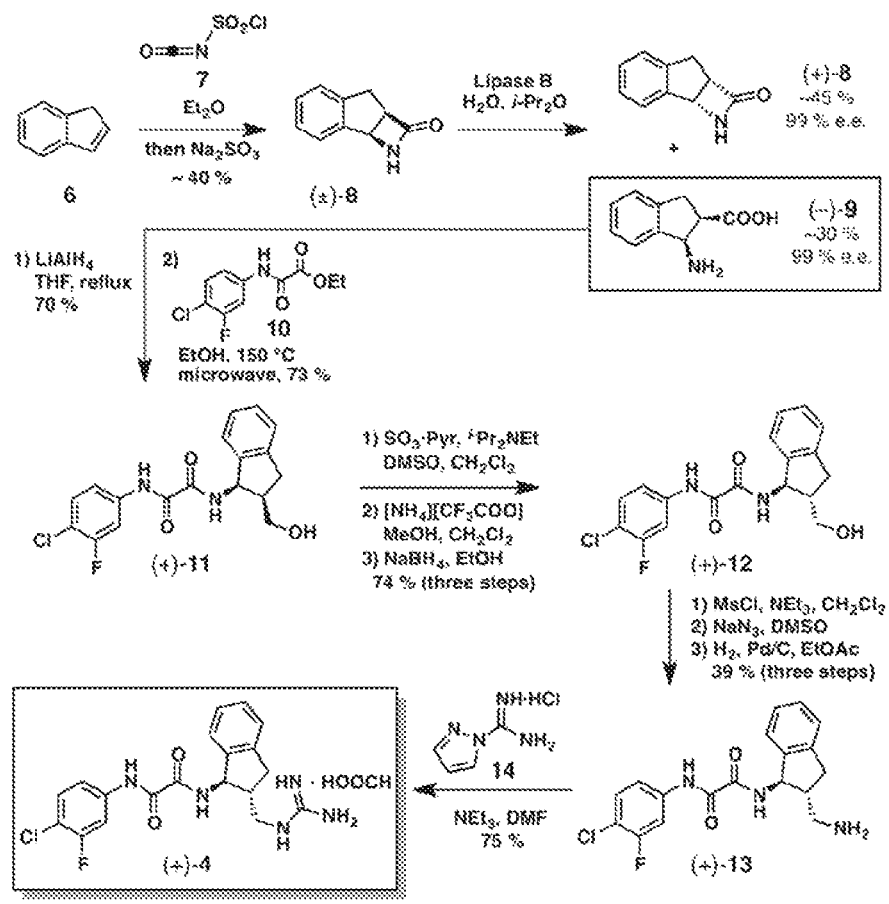
FIG. 15 depicts a synthetic scheme to single enantiomer (+)-4 (from FIG. 13).
Figure 16:
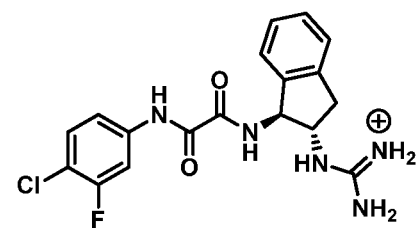
FIG. 16 depicts the structure of (+)-3.

X-ray crystallography was used to investigate the interactions between antagonist (±)-4 (the structure of (+)-4 is depicted in FIG. 15) and gp120 and to define the enantiomer that preferentially binds to the gp120 core. The formate salt of (±)-4 was soaked into preformed crystals of gp120 from Clade C1086, and diffraction data were obtained to 2.5 Å Bragg spacings. The observed electron density for each of the two 4:gp120 complexes in the asymmetric unit clearly revealed preferential binding of the (R,R)-4 enantiomer to gp120 during the soaking process (data not shown). Interestingly, the (R,R)-4:gp120 crystal structure revealed that the guanidinium moiety did not directly interact with Asp368$_{gp120}$.

Because the crystal structure suggested that the (R,R)-4 enantiomer possesses higher affinity for gp120, a synthetic route to the single (R,R)-enantiomer was developed (FIG. 15). An identical synthetic scheme was employed to furnish (−)-4 following opening of the β-lactam (+)-8 from FIG. 15.

Antiviral assays revealed that (+)-4 inhibits viral entry of the YU-2 primary HIV-1 isolate with an IC$_{50}$ value of 3.1±0.6 μM, while the (−)-4 antipode exhibits a ten-fold reduction in antiviral activity, with an observed IC$_{50}$=37.9±22.7 μM (FIG. 13). To assess further the HIV-1 neutralization breadth and potency, we assayed 1, (+)-3, (+)-4 against 42 diverse strains of clades B and C Env-pseudoviruses (data not shown). (+)-4 neutralized Glade B viruses better than Glade C viruses, with 100% breadth and an IC$_{50}$ GMT of 1.7 μM against Glade B viruses, compared to 59% breadth and an IC$_{50}$ GMT of 14.0 μM against the sensitive Glade C viruses. Moreover, (+)-4 demonstrated a 60% improvement over (+)-3 based on IC$_{50}$ titers in Glade B viruses and a 1.5-folder improvement based on IC$_{80}$ titers. In addition, ITC measurements found that (+)-4 binds full-length gp120 with a K$_d$=110 nM (FIG. 13 and FIG. 14). In contrast, (−)-4 has a significantly reduced binding affinity of 6,200 nM. These results are consistent with the gp120-bound co-crystal structure derived from (±)-4, suggesting the (R,R)-enantiomer preferentially binds to the monomer gp120 core.

Given that inclusion of the methylene spacer led to significant improvements in both binding affinity and functional antagonism of HIV-1 viral entry into target cells, we constructed (±)-5 containing an additional methylene spacer between the indane scaffold and the guanidinium moiety (see later Examples). Semi-preparative chiral SFC furnished samples of (+)-5 and (−)-5 for biological evaluation. Assessment of the functional antagonist activity of (+)-5 and (−)-5 revealed that both were less potent than (+)-4. Evaluation of compounds (+)-4, (−)-4, (+)-5 and (−)-5 by ITC (FIG. 13 and FIG. 14) when compared to (+)-3 and (−)-3, demonstrates that (+)-4 exhibits the best sub-micromolar binding affinity observed thus far for a small molecule-gp120 complex. Moreover, the enthalpic and entropic contributions of the three (+) antipodes [i.e., (+)-3, (+)-4 and (+)-5] exhibited the preferred thermodynamic signature of having smaller entropic penalties as compared with the (S,S)-counterparts.

Figure 17A:
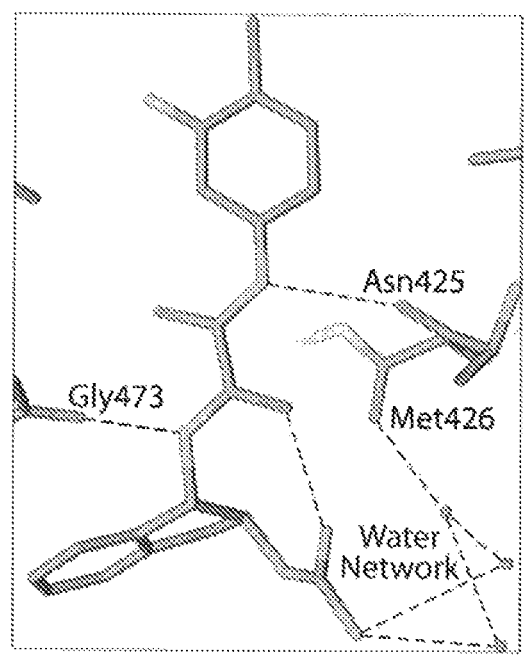
FIG. 17 depicts a comparison of (+)-3- and (+)-4:gp120 crystal structures. A) The structures of (+)-3:gp120 (PDB ID: 4DKQ)28 and B) (+)-4:gp120 (Clade E, copy A) indicate that (+)-3 interacts with Met426gp 120 via a network of water molecules whereas the guanidinium group of (+)-4 hydrogen bonds directly to the backbone carbonyl of Met426gp120. Hydrogen bonds are represented by dashed lines.
Figure 17B:
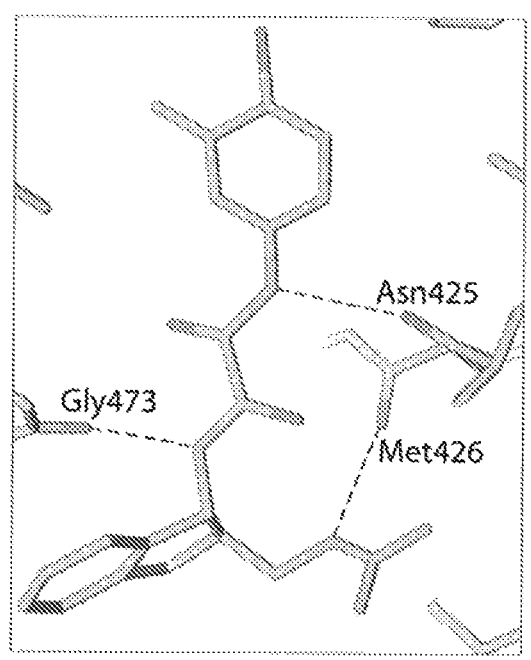
Figure 18:
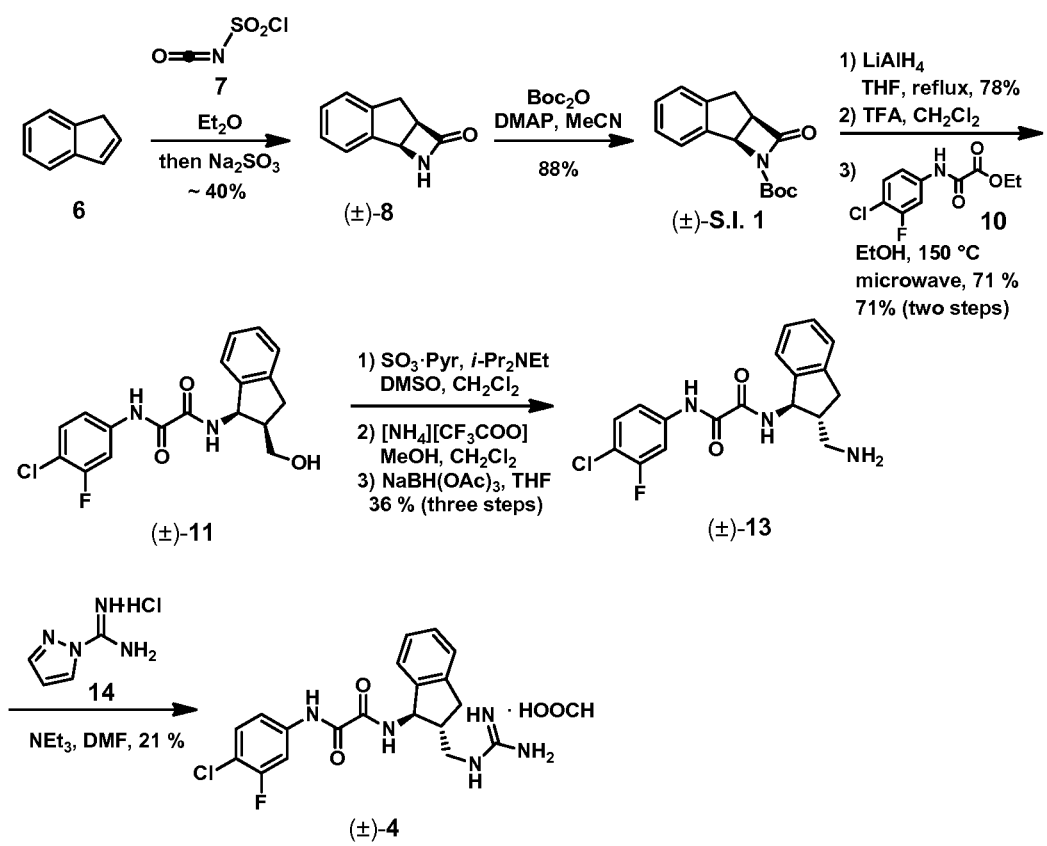
FIG. 18 depicts a synthesis of (±)-4 from Example 18.

Crystallography was once more employed to ascertain the binding interactions between gp120 and (+)-4. Co-crystallization of (+)-4 with the Glade A/E93TH057 extended gp120$_{(H375S)}$ core produced crystals that diffracted to 2.5 Å spacings (data not shown). There are two complexes in the asymmetric unit of these crystals, and each (+)-4 molecule in both complexes has similar conformations that closely resemble those observed in the (R,R)-4:gp120 structure obtained from (±)-4 (data not shown). As expected, the previously observed hydrogen bonds between the oxalamide linker and the Asn425$_{gp120}$ and Gly473-$_{gp120}$ amide nitrogen atoms are preserved in the (+)-4:gp120 complex. Surprisingly, as noted for (R,R)-4:gp120 (vide supra), the guanidinium moiety did not directly interact with Asp368$_{gp120}$. Instead, a hydrogen bond is formed between one guanidinium nitrogen and the bridging sheet backbone carbonyl of Met426$_{gp120}$. Importantly, the crystallographic water molecules necessary for the indirect interaction with Met426$_{gp120}$ in the (+)-3:gp120 structure are now displaced by the extended guanidinium of the (+)-4:gp120 (FIG. 17) allowing for direct hydrogen bonding to the carbonyl of Met426$_{gp120}$. The direct hydrogen bond as well as the displacement of crystallographic water molecules provides a plausible explanation of the improved potency of (+)-4 over the previous (+)-3. This suggests that incorporation of the guanidinium- Asp368$_{gp120}$ contact as observed in the (+)-3:gp120 complex with the newly revealed guanidinum-Met426$_{gp120}$ interaction exhibited in the (+)-4:gp120 structure will in the future yield even more potent inhibitors of viral entry.

Example 18

Synthetic Procedures

General Information for Remaining Examples

All reactions were conducted in oven-dried glassware under an inert atmosphere of nitrogen or argon, unless otherwise stated. All solvents were reagent or high performance liquid chromatography (HPLC) grade. Anhydrous $CH_2Cl_2$ and THF were obtained from the Pure Solve™ PS-400 system under an argon atmosphere. All reagents were purchased from commercially available sources and used as received. Reactions were magnetically stirred under a nitrogen atmosphere, unless otherwise noted and reactions were monitored by either thin layer chromatography (TLC) with 0.25 mm. E Merck pre-coated silica gel plates or analytical high performance liquid chromatography (HPLC). Yields refer to chromatographically and spectroscopically pure compounds. Optical rotations were measured on a JASCO P-2000 polarimeter. Proton and carbon-13 NMR spectra were recorded on a Bruker AM-500 at 305 K, unless otherwise noted. Chemical shifts are reported relative to chloroform (δ7.26), methanol (δ3.31), or dimethyl sulfoxide (δ2.50) for $^1$H NMR and either chloroform (δ77.0), methanol (δ49.2), or dimethyl sulfoxide (δ39.4). High-resolution mass spectra (HRMS) were recorded at the University of Pennsylvania Mass Spectroscopy Service Center on either a VG Micromass 70/70H or VG ZAB-E spectrometer. Analytical HPLC was preformed with a Waters HPLC-MS system, consisting of a 515 pump and Sunfire C18 reverse phase column (20 μL injection volume, 5 μm packing material, 4.5×50 mm column dimensions) with detection accomplished by a Micromass ZQ mass spectrometer and 2996 PDA detector. Preparative scale HPLC was preformed with a Gilson 333/334 preparative pump system equipped with a 5 mL injection loop, Sunfire C18 OBD column (5 μm packing material, 19×100 mm column dimensions) equipped with a UV-Vis dual wavelength (210 and 254 nm) detector and 215 liquid handling module. Solvent systems employed were based on the following buffers: Buffer A: $H_2O$ containing 0.05% formic acid; Buffer B: MeCN containing 0.05% formic acid. Microwave reactions were run on a Biotage Initiator Microwave Synthesizer. Super-Critical Fluid Chromatography (SFC) purifications were performed with a JASCO system equipped with a Chiralpak AD-H, Chiralpak IC, or Chiralcel OD-H column (10 mm×250 mm), a PU-280-$CO_2$ plus $CO_2$ Delivery System, a CO-2060 plus Intelligent Column Thermostat, an HC-2068-01 Heater Controller, a BP-2080 plus Automatic Back Pressure Regulator, an MD-2018 plus Photodiode Array Detector (200-648 nm), and PU-2080 plus Intelligent HPLC Pumps. The purity of new compounds was judged by NMR and LCMS (>95%).

See FIG. 18.

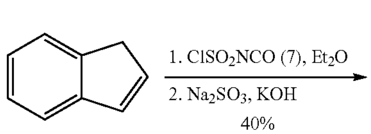

6

-continued (±)-8

(±)-3,4-Benzo-cis-6-azabicyclo[3.2.0]heptane-7-one [(±)-8].[1]

To a solution of indene 6 (3.62 g, 31.4 mmol) in ether (60 mL) stirring at room temperature was added chlorosulfonyl isocyanate 7 (3.00 mL, 34.5 mmol) in ether (40 mL). The solution was allowed to stir for 2 h at room temperature, at which time, an additional 1.0 mL (11.5 mmol) of neat isocyanate 7 was added and the mixture stirred an additional hour. To the mixture was added 150 mL of hexane and the reaction mixture was stirred vigorously. The precipitate was allowed to settle, and the solvent was gently decanted while retaining an inert atmosphere in the reaction vessel. The solid was then suspended in ether (100 mL) and to the heterogeneous mixture was added 5 mL of 0.2 M aqueous $Na_2SO_3$ dropwise (the reaction mixture was kept basic by the occasional dropwise addition of 10% KOH solution). After completing the addition of $Na_2SO_3$, 100 mL of hexanes was added and the heterogeneous solution was filtered. The filtrate was washed with additional hexane and the mother liquor was concentrated to remove ether and filtered again. The crude product was dissolved in a minimal amount of hot methanol and EtOAc was added until the solution remained slightly cloudy. The solution was then cooled and the precipitate collected to provide 2.05 g (40%) of (±)-8 as a white solid.

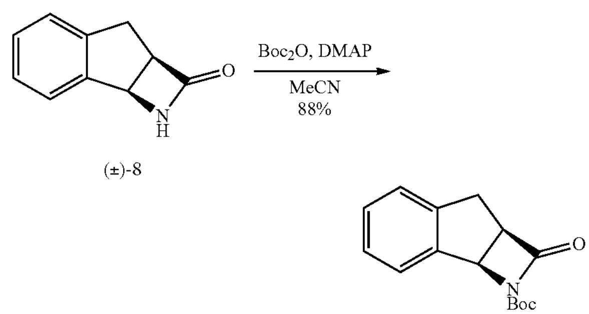

(±)-8

(±)-S.I. 1

(±)-N-Boc-3,4-benzo-cis-6-azabicyclo[3.2.0]heptanes-7-one [(±)-S.I. 1]

To a solution of (±)-8 (409 mg, 2.57 mmol) in MeCN (10 mL) at 0° C., was added DMAP (78 mg, 0.64 mmol), followed by $Boc_2O$ (1.12 g, 5.14 mmol). The solution was warmed to room temperature and stirred for 1 h. The mixture was diluted with $CH_2Cl_2$, washed with a sat. $NaHCO_3$ solution, and washed with a brine solution. The organic layer was then dried over anhydrous $MgSO_4$ and concentrated. The crude mixture was purified by silica gel column chromatography using EtOAc/hexanes (10% to 30%) to afford 581 mg (88%) of the pure Boc-protected β-lactam (±)-S.I. 1.

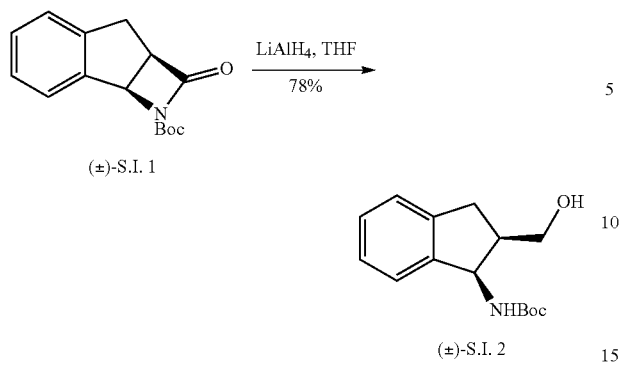

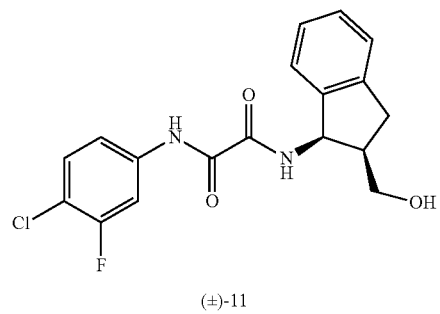

(±)-N-Boc-cis-2-(hydroxymethyl)indanyl-1-amine (±)-N$^1$-(4-Chloro-3-fluorophenyl)-N$^2$-(cis-2-(hydroxymethyl)-indan-1-yl)oxalamide [(±)-11]

[(±)-S.I. 2]. To a solution of (±)-S.I. 1 (581 mg, 2.25 mmol) in THF (10 mL) at 0° C. was added solid LiAlH$_4$ (298 mg, 7.86 mmol) portion-wise. The reaction mixture was then warmed to room temperature and stirred overnight. The reaction was then quenched with the dropwise addition of 0.3 mL H$_2$O, after 5 minutes, this was followed by 0.3 mL of 15% aqueous NaOH, and then after another 5 minutes, an additional 0.9 mL of H$_2$O was added. The heterogeneous mixture was stirred until the solid aluminum salts became white and the precipitate was filtered off. The remaining solution was then concentrated and the residue purified by silica gel column chromatography using EtOAc/hexanes (20% to 50%) to provide 463 mg (78%) of (±)-S.I. 2. $^1$H NMR (500 MHz, DMSO-d$_6$): δ 7.38 (d, J=6.9 Hz, 1H), 7.19-7.28 (m, 3H), 5.12 (dd, J=6.9, 6.7 Hz, 1H), 4.56 (d, J=6.9 Hz, 1H), 3.75-3.85 (m, 1H), 3.65-3.75 (m, 2H), 2.84 (dd, J=15.0 Hz, 7.3 Hz, 1H), 2.70-2.80 (m, 1H), 2.59 (dd, J=15.0, 9.7 Hz, 1H), 1.47 (s, 9H); HRMS (ES+) m/z 286.1422 ([M+Na]$^+$; calcd for C$_{15}$H$_{21}$NO$_3$Na: 286.1419).

To a solution of (±)-S.I. 2 (463 mg, 1.76 mmol) in CH$_2$Cl$_2$ (5 mL) at 0° C. was added TFA (2 mL). The reaction mixture was warmed to room temperature and stirred for 45 min. The solution was then cooled back to 0° C. and the quenched with 2 N NaOH until the pH of the aqueous layer was β-14. The aqueous layer was extracted with CH$_2$Cl$_2$ (8×5 mL), the combined organic layers were then dried over anhydrous Na$_2$SO$_4$ and concentrated to afford amino alcohol (±)-S.I. 3. The unpurified amine (±)-S.I. 3 was immediately dissolved in EtOH (5 mL) and the solution was transferred into a vial containing oxalamide ester 10, the vial was then sealed and the solution was heated to 150° C. in a microwave reactor for 1 h. Upon cooling to room temperature, a precipitate formed in the reaction vessel. The precipitate was filtered and washed with small portions of cold CH$_2$Cl$_2$ to provide 455 mg (72%) of (±)-11 as a white solid. $^1$H NMR (500 MHz, DMSO-d$_6$) δ 11.08 (br. s, 1H), 9.22 (d, J=8.7 Hz, 1H), 7.95 (dd, J=11.8, 2.3 Hz, 1H), 7.73 (dd, J=8.9, 1.8 Hz, 1H), 7.57 (d, J=17.2 Hz, 1H), 7.20-7.28 (m, 3H), 7.13-7.20 (m, 1H), 5.45 (t, J=8.2 Hz, 1H), 4.81 (t, J=4.8 Hz, 1H), 3.51-3.60 (m, 2H), 2.90-3.01 (m, 2H), 2.70-2.79 (m, 1H); $^{13}$C NMR (125 MHz, DMSO-d$_6$) 159.4, 158.9, 156.8 (d, J$_{CF}$=242 Hz), 142.8, 142.5, 138.3 (d, J$_{CF}$=10 Hz), 130.5, 127.8, 126.4, 124.6, 124.4, 117.3, 114.3 (d, J$_{CF}$=18 Hz), 108.5 (d, J$_{CF}$=26 Hz), 60.8, 55.7, 43.2, 33.6; HRMS (ESI−) m/z=361.0759 ([M−H]$^−$; calcd for C$_{18}$H$_{15}$N$_2$O$_3$ClF: 361.0755).

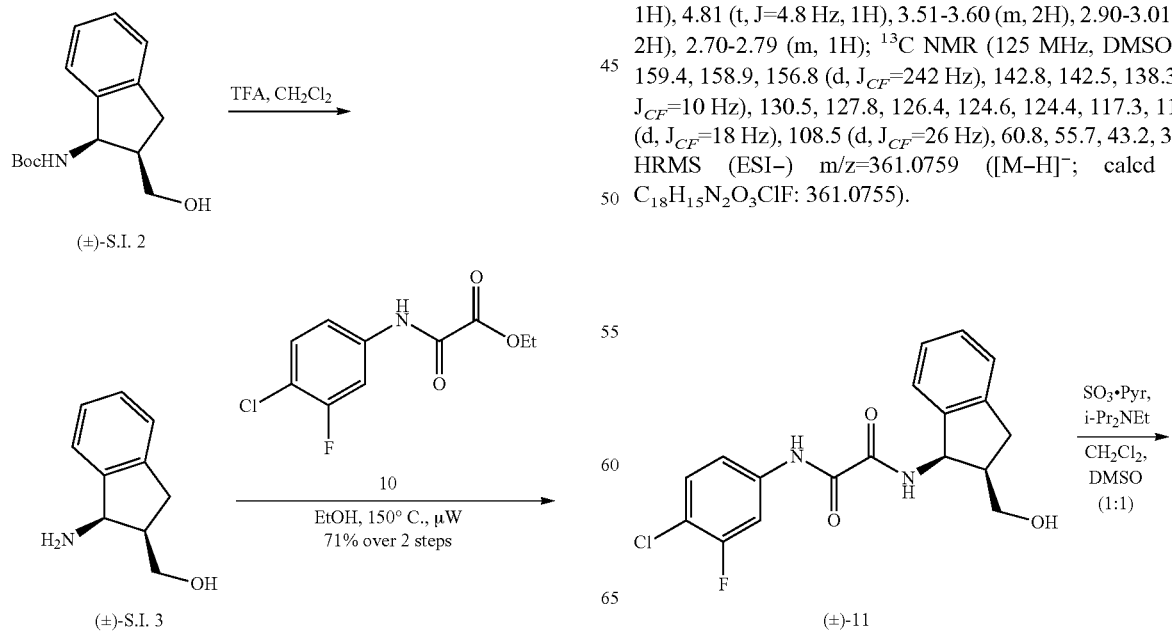

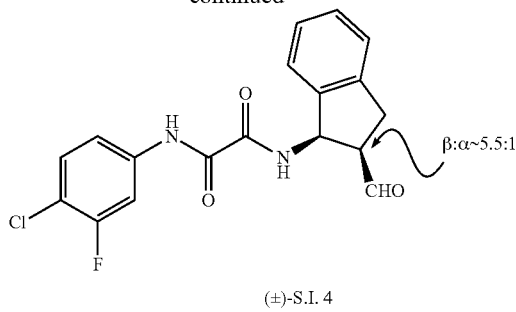

(±)-S.I. 4

(±)-N¹-(4-Chloro-3-fluorophenyl)-N²-(cis-2-formylindan-1-yl)oxalamide [(±)-S.I. 4]

To a solution of alcohol (±)-11 (140 mg, 0.38 mmol) in CH$_2$Cl$_2$/DMSO (1:1, 2 mL) at 0° C. was added i-Pr$_2$NEt (0.40 mL, 2.32 mmol), followed by SO$_3$.Pyr (363 mg, 2.28 mmol). The reaction mixture was stirred at 0° C. for 45 min, and then quenched by the addition of a sat. aqueous NaHCO$_3$ (3 mL). The aqueous layer was extracted with CH$_2$Cl$_2$ (3×3 mL), and the combined organic layers washed with brine and dried with anhydrous Na$_2$SO$_4$. After concentration of the organic layers, the crude material was then purified by silica gel chromatography using EtOAc/hexanes (20% to 25%) to afford 122 mg (89%) of (±)-S.I. 4 as an ~5.5:1 mixture of mixture of epimers. $^1$H NMR$_{major}$ (500 MHz, DMSO-d$_6$) δ 11.03 (s, 1H), 9.68 (d, J=1.6 Hz, 1H), 9.46 (d, J=8.9 Hz, 1H), 7.92 (dd, J=11.8, 2.2 Hz, 1H), 7.72 (d, J=9.3 Hz, 1H), 7.57 (t, J=8.7 Hz, 1H), 7.19-7.33 (m, 4H), 5.73 (t, J=8.7 Hz, 1H), 3.56-3.62 (m, 1H), 3.49 (dd, J=15.9, 6.9 Hz, 1H), 3.04 (dd, J=15.9, 8.5 Hz, 1H); LC/MS: m/z=361.11 (M+H)$^+$.

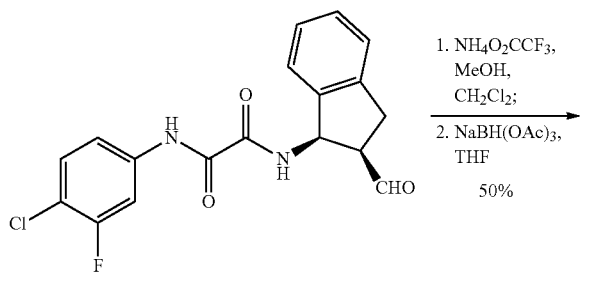

(±)-S.I. 4

1. NH$_4$O$_2$CCF$_3$, MeOH, CH$_2$Cl$_2$;
2. NaBH(OAc)$_3$, THF

50%

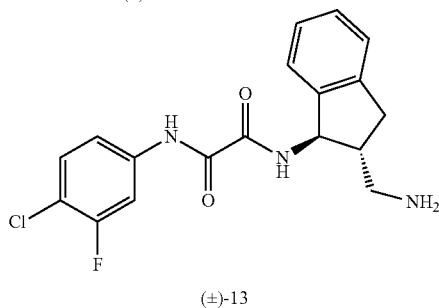

(±)-13

(±)-N¹-(4-Chloro-3-fluorophenyl)-N²-(trans-2-(aminomethyl)indan-1-yl)oxalamide [(±)-13]

To a solution of aldehyde (±)-S.I. 4 (35 mg, 0.1 mmol) in MeOH/CH$_2$Cl$_2$ (1:1, 3 mL) was added ammonium trifluoroacetate (131 mg, 1.0 mmol). The solution was stirred at room temperature overnight. The solvent was then evaporated and the residual solvents were then removed via azeotrope with toluene (~10 mL). The dry solid was then dissolved in THF (5 mL) and the solution stirred for 1 h, at which time, NaBH(OAc)$_3$ (25 mg, 0.12 mmol) was added in one portion. The reaction mixture was stirred for 4 h at room temperature, and then concentrated directly onto silica gel. The crude mixture was purified by silica gel chromatography using CH$_2$Cl$_2$/MeOH (2% to 10%) to afford 18 mg (50%) of (±)-13 as a white solid. $^1$H NMR (500 MHz, DMSO-d$_6$) δ 9.39 (br. s, 1H), 7.97 (dd, J=11.8, 2.2 Hz, 1H), 7.75 (d, J=9.0 Hz, 1H), 7.59 (t, J=8.7 Hz, 1H), 7.14-7.27 (m, 4H), 5.20 (d, J=6.5 Hz, 1H), 3.10-3.16 (m, 1H), 2.96-3.02 (m, 2H), 2.71-2.74 (m, 2H); $^{13}$C NMR (125 MHz, DMSO-d$_6$) δ 160.1, 158.8, 156.8 (d, J$_{CF}$=243 Hz), 142.1, 141.2, 138.3 (d, J$_{CF}$=10 Hz), 130.6, 127.7, 126.6, 124.5, 123.5, 117.3 (d, J$_{CF}$=3.3 Hz), 114.3 (d, J$_{CF}$=18 Hz), 108.4 (d, J$_{CF}$=26 Hz), 57.5, 45.7, 41.8, 34.3; HRMS (ES+) m/z=362.1067 ([M+H]$^+$; calcd for C$_{18}$H$_{18}$N$_3$O$_2$FCl: 362.1072).

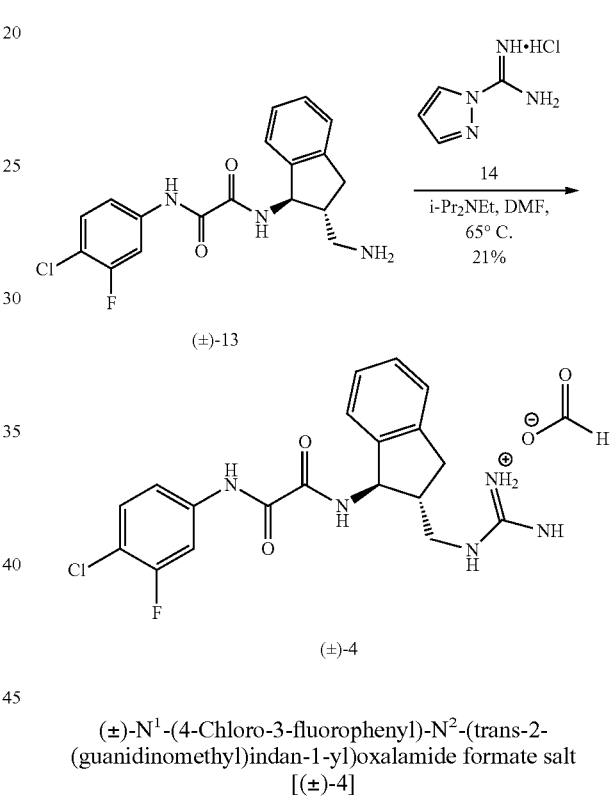

(±)-N¹-(4-Chloro-3-fluorophenyl)-N²-(trans-2-(guanidinomethyl)indan-1-yl)oxalamide formate salt [(±)-4]

To a solution of amine (±)-13 (15 mg, 0.04 mmol) in DMF (1 mL) was added i-Pr$_2$NEt (30 μL), followed by carbamidine 14 (12 mg, 0.08 mmol). The mixture was then heated to 65° C. for 2 h. The reaction mixture was then cooled to room temperature and diluted with of MeCN/H$_2$O (2:1, 1.2 mL) and the product purified via HPLC to provide 3.7 mg (21%) of the formate salt (±)-4 as a white solid. $^1$H NMR (500 MHz, DMSO-d$_6$) δ 11.06 (br. s, 1H), 9.41 (d, J=8.8 Hz, 1H), 8.36 (s, 1H), 8.05 (br. s, 1H), 7.97 (dd, J=11.8, 2.2 Hz, 1H), 7.75 (d, J=7.5 Hz, 1H), 7.59 (t, J=8.7 Hz, 1H), 7.37 (br. s, 3H), 7.14-7.27 (m, 4H), 5.18 (t, J=8.4 Hz, 1H), 3.30-3.41 (m, 2H), 3.11-3.17 (m, 2H), 2.79-2.84 (m, 1H), 2.65-2.71 (m, 1H); $^{13}$C NMR (125 MHz, CD$_3$OD) δ 162.0, 159.8, 159.3 (d, J$_{CF}$=245 Hz), 159.0, 142.8, 142.6, 139.2 (d, J$_{CF}$=10 Hz), 131.9, 129.7, 128.4, 126.1, 125.2, 118.2 (d, J$_{CF}$=3.5 Hz), 117.4 (d, J$_{CF}$=18 Hz), 109.9 (d, J$_{CF}$=26 Hz), 59.4, 48.5, 45.1, 35.5; HRMS (ES+) m/z=404.1281 ([M+H]$^+$; calcd for C$_{19}$H$_{20}$N$_5$O$_2$FCl: 404.1290). The formate counterion was not observed under the HRMS conditions.

Example 19

Synthetic Procedures

Figure 19:
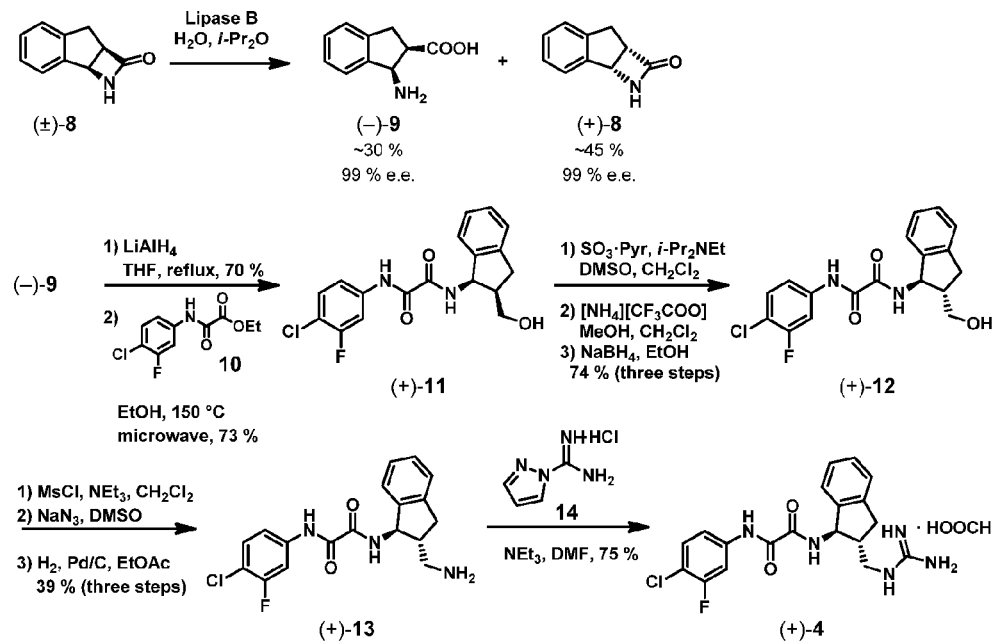
FIG. 19 depicts an enantioselective synthesis of (+)-4 from Example 19.

See FIG. 19.

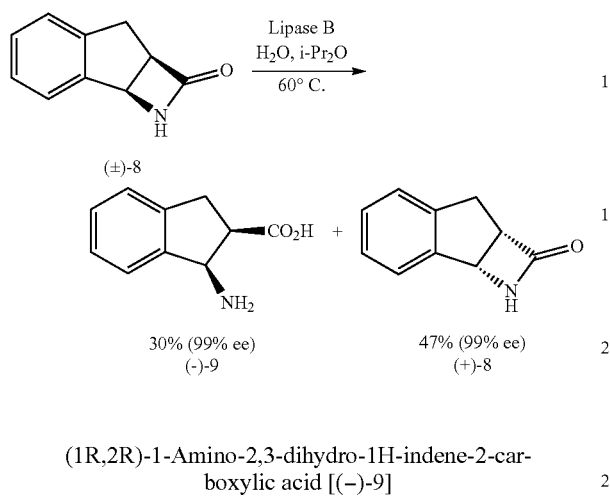

(±)-8

30% (99% ee) (−)-9

47% (99% ee) (+)-8

(1R,2R)-1-Amino-2,3-dihydro-1H-indene-2-carboxylic acid [(−)-9]

Racemic β-lactam (±)-8 (530 mg, 3.32 mmol) was suspended in i-Pr$_2$O (50 mL). After addition of lipase (1.0 g, lipase B from *Candida antarctica* on styrene) and H$_2$O (60 μL, 3.32 mmol), the mixture was shaken in a water bath at 60° C. The reaction was monitored by chiral SFC (Chiralcel OD-H, 20% (0.5% NEt$_3$/MeOH)/CO$_2$, 254 nm, 4 mL/min, 12 MPa; (+)-isomer: t$_r$=1.8 min and (−)-isomer: t$_r$=2.5 min), and was stopped when the ee of β-lactam (+)-8 reached 99%. The reaction mixture was filtered to collect enzyme and amino acid and washed by MeOH several times. The filtrate was evaporated under reduced pressure, and the residue was recrystallized from MeOH/EtOAc to afford β-lactam (+)-8 (250 mg, 47%, 99% ee). The filtered enzyme and amino acid were washed with hot H$_2$O, and the H$_2$O was evaporated under reduced pressure. The residue was washed with small amount of MeOH to afford β-amino acid (−)-9 (175 mg, 30%, 99% ee) as a white solid.[i] The enantiomeric excess of β-lactam (+)-8 was determined as 99% ee by SFC (Chiralcel OD-H, 20% (0.5% NEt$_3$/MeOH)/CO$_2$, 254 nm, 4 mL/min, 12 MPa; (+)-enantiomer: t$_r$=1.8 min and (−)-enantiomer: t$_r$=2.5 min) The enantiomeric excess of amino acid (−)-9 was determined as 99% ee by SFC (Chiralpak IC, 30% (0.5% NEt$_3$/MeOH)/CO$_2$, 254 nm, 4 mL/min, 12 MPa; (−)-enantiomer: t$_r$=2.5 min and (+)-enantiomer: t$_r$=3.6 min)

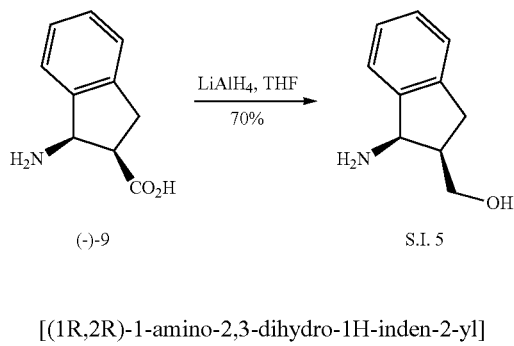

(−)-9

S.I. 5

[(1R,2R)-1-amino-2,3-dihydro-1H-inden-2-yl]methanol (S.I. 5)

To a solution of (−)-9 (121 mg, 0.68 mmol) in THF (5 mL) at 0° C., LiAlH$_4$ (104 mg, 2.74 mmol) was carefully added. The solution was heated to reflux and stirred overnight. The reaction mixture was cooled to 0° C., then quenched with the dropwise addition of 0.10 mL H$_2$O, followed by 0.10 mL of 15% aqueous NaOH, then an additional 0.20 mL of H$_2$O was added. The heterogeneous mixture was stirred until the solid aluminum salt became white and the precipitate was filtered off. The resulting solution was concentrated to give 78 mg (70%) of S.I. 5 as a pale yellow solid. This compound was used for the next step without further purification (>90% purity estimated by $^1$H NMR).

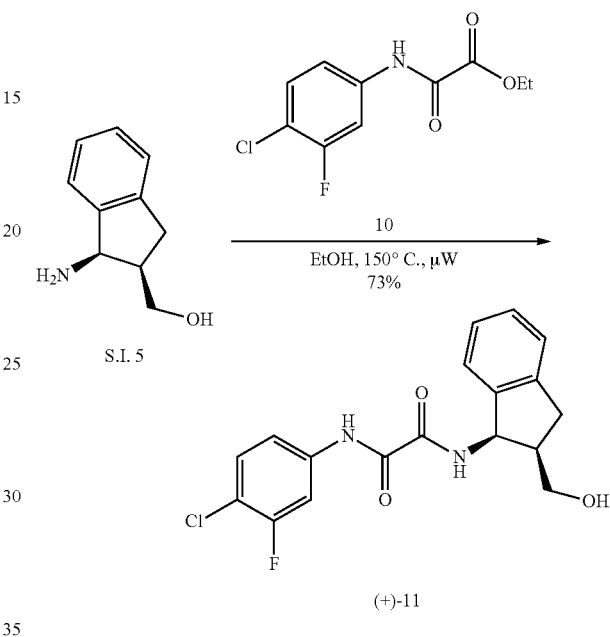

S.I. 5

10

(+)-11

N$^1$-(4-Chloro-3-fluorophenyl)-N$^2$-((1R,2R)-2-(hydroxymethyl)-2,3-dihydro-1H-inden-1-yl)oxalamide [N-11]

A solution of amino alcohol S.I. 6 (105 mg, 0.64 mmol) in EtOH (1.5 mL) was transferred into a vial containing oxalamide ester S.I. 5 (157 mg, 0.64 mmol), the vial was then sealed and the mixture was heated to 150° C. in a microwave reactor for 1 h. Upon cooling to room temperature a precipitate formed in the reaction vessel. The reaction mixture was purified by silica gel column chromatography using EtOAc/hexanes (20% to 100%) to give 171 mg (73%) of (+)-11 as a white solid [$^1$H and $^{13}$C NMR data consistent with (±)-11]. [α]$_D$=+124.8 (c 0.21, DMSO).

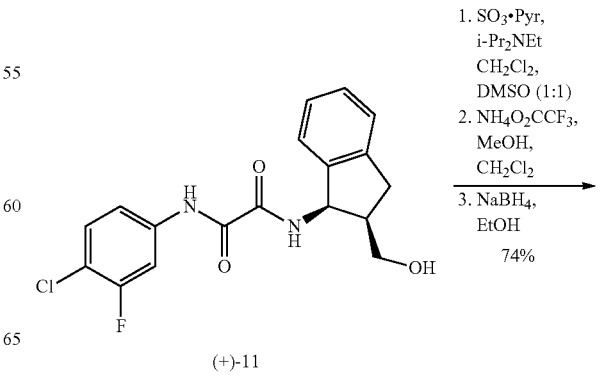

(+)-11

1. SO$_3$·Pyr, i-Pr$_2$NEt CH$_2$Cl$_2$, DMSO (1:1)
2. NH$_4$O$_2$CCF$_3$, MeOH, CH$_2$Cl$_2$
3. NaBH$_4$, EtOH

74%

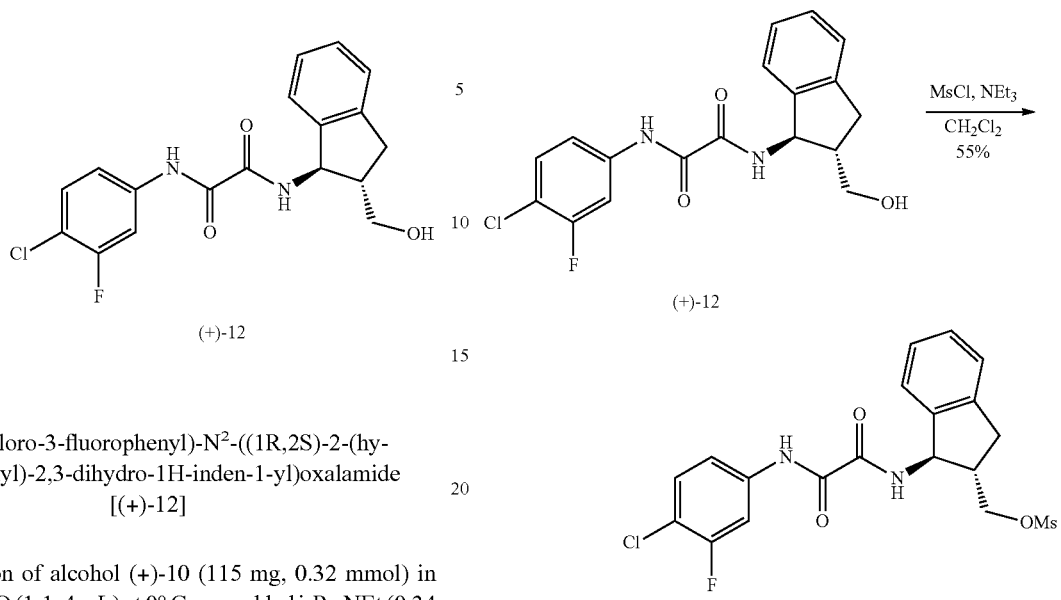

(+)-12

N$^1$-(4-Chloro-3-fluorophenyl)-N$^2$-((1R,2S)-2-(hydroxymethyl)-2,3-dihydro-1H-inden-1-yl)oxalamide [(+)-12]

To a solution of alcohol (+)-10 (115 mg, 0.32 mmol) in CH$_2$Cl$_2$/DMSO (1:1, 4 mL) at 0° C. was added i-Pr$_2$NEt (0.34 mL, 1.95 mmol), followed by SO$_3$.Pyr (303 mg, 1.90 mmol). The reaction mixture was stirred at 0° C. for 1 h, and then quenched by the addition of saturated aqueous NaHCO$_3$. The aqueous layer was extracted with CH$_2$Cl$_2$ (3×5 mL), and the combined organic layer washed with brine and dried over anhydrous Na$_2$SO$_4$. After concentration of the organic layer, the residue was purified by silica gel column chromatography using EtOAc/hexanes (10% to 100%) to give the desired aldehyde [$^1$H NMR consistent with (±)-S.I. 4]. To a solution of the resulting aldehyde in 1:1 MeOH/CH$_2$Cl$_2$ (6 mL) was added ammonium trifluoroacetate (207 mg, 1.58 mmol). The solution was stirred at room temperature overnight, then the reaction mixture was evaporated to remove solvent, the crude residue was dissolved in ethyl acetate, washed with water, dried with Na$_2$SO$_4$, and concentrated. The $^1$H NMR of crude aldehyde indicated that the ratio of epimers was ~8:1 (α:β) [$^1$H NMR$_{major}$ (500 MHz, DMSO-d$_6$) δ 11.07 (s, 1H), 9.83 (d, J=2.0 Hz, 1H), 9.58 (d, J=8.9 Hz, 1H), 7.95 (dd, J=9.9, 2.3 Hz, 1H), 7.74 (d, J=9.3 Hz, 1H), 7.58 (t, J=8.8 Hz, 1H), 7.16-7.32 (m, 4H), 5.74 (t, J=7.2 Hz, 1H), 3.50-3.57 (m, 1H), 3.21-3.28 (m, 1H), 3.13-3.19 (m, 1H)]. The partially epimerized aldehyde was then dissolved in EtOH, and NaBH$_4$ was added. After stirring overnight, the reaction mixture was quenched with H$_2$O. The mixture was diluted with EtOAc, and washed with H$_2$O and brine. The organic layer was dried over anhydrous Na$_2$SO$_4$, and the residue was washed with a CH$_2$Cl$_2$/hexanes mixture (1:1) to give 86 mg (74%) of (+)-12 as a white solid. $^1$H NMR (500 MHz, DMSO-d$_6$) δ 11.06 (s, 1H), 7.96 (dd, J=11.9, 2.2 Hz, 1H), 7.71-7.77 (m, 1H), 7.51-7.61 (m, 1H), 7.11-7.27 (m, 4H), 5.23 (t, J=8.3 Hz, 1H), 4.69 (t, J=5.1 Hz, 1H), 3.48-3.60 (m, 2H), 3.01-3.09 (m, 1H), 2.65-2.77 (m, 2H); $^{13}$C NMR (125 MHz, DMSO-d$_6$) δ 159.8, 159.0, 156.8 (d, J$_{CF}$=243 Hz), 142.9, 142.2, 138.2 (d, J$_{CF}$=10 Hz), 130.5, 127.5, 126.4, 124.6, 123.7, 117.3, 114.3 (d, J$_{CF}$=18 Hz), 108.5 (d, J$_{CF}$=26 Hz), 61.8, 56.1, 48.2, 33.4; HRMS (ESI-) m/z=361.0751 ([M−H]$^-$; calcd for C$_{18}$H$_{15}$N$_2$O$_3$ClF: 361.0755); [α]$_D$=+130.2 (c 0.21, DMSO).

S.I. 6

[(1R,2S)-1-{2-((4-Chloro-3-fluorophenyl)amino)-2-oxoacetamido)-2,3-dihydro-1H-inden-2-yl}methyl] methanesulfonate [S.I. 6]

To a mixture of alcohol (+)-11 (75 mg, 0.21 mmol) and Et$_3$N (0.11 mL, 0.79 mmol) in CH$_2$Cl$_2$ (5 mL) at 0° C. was added MsCl (48 µL, 0.62 mmol). After stirring overnight, the reaction mixture was concentrated. The residue was diluted with EtOAc and then washed with 1 N HCl, sat. NaHCO$_3$, and brine. The organic layer was dried over anhydrous Na$_2$SO$_4$, concentrated under reduced pressure, and the residue was purified by silica gel column chromatography using EtOAc/hexanes (20% to 100%) to give 50 mg (55%) of S.I. 6 as a white solid. $^1$H NMR (500 MHz, CDCl$_3$) δ 9.34 (s, 1H), 7.80 (d, J=8.5 Hz, 1H), 7.72 (d, J=10.5 Hz, 1H), 7.38 (t, J=8.3 Hz, 1H), 7.22-7.31 (m, 5H), 5.40 (t, J=8.3 Hz, 1H), 4.46 (m, 2H), 3.23 (dd, J=15.8, 8.3 Hz, 1H), 3.09 (s, 3H), 2.92 (dd, J=16.3, 8.8 Hz, 1H), 2.77 (m, 1H); LCMS: m/z=441.0 (M+H); [α]$_D$=+34.04 (c 0.085, MeOH).

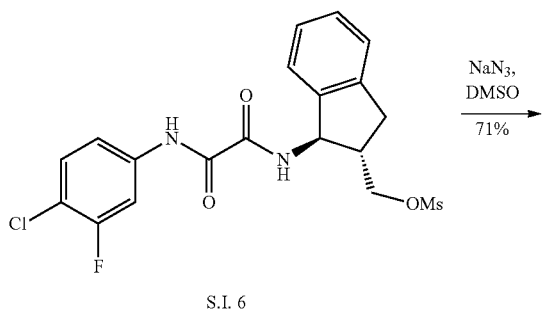

S.I. 6

77

-continued

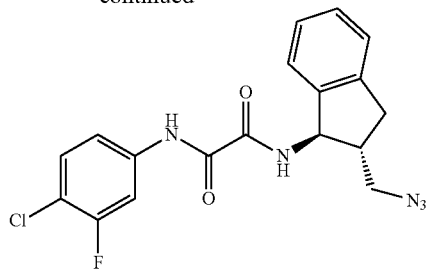

S.I. 7

N-((1R,2R)-2-(Azidomethyl)-2,3-dihydro-1H-inden-1-yl)-N²-(4-chloro-3-fluorophenyl)-oxalamide [S.I. 7]

To a solution of S.I. 6 (50 mg, 0.11 mmol) in DMSO (1 mL) at room temperature, was added NaN$_3$ (15 mg, 0.23 mmol). The solution was heated to 70° C. and stirred for 3 h at this temperature. The reaction mixture was diluted with EtOAc, and washed with H$_2$O and brine. The organic layer was dried over anhydrous Na$_2$SO$_4$, concentrated under reduced pressure, and the residue was purified by silica gel column chromatography using EtOAc/hexanes (10% to 33%) to give 31 mg (71%) of S.I. 7 as a white solid. $^1$H NMR (500 MHz, CDCl$_3$) δ 9.40 (s, 1H), 7.78 (d, J=8.5 Hz, 1H), 7.72 (d, J=10.0 Hz, 1H), 7.38 (t, J=8.0 Hz, 1H), 7.20-7.34 (m, 5H), 5.33 (t, J=8.0 Hz, 1H), 3.57-3.67 (m, 2H), 3.19 (dd, J=16.0, 7.5 Hz, 1H), 2.83 (dd, J=15.8, 8.3 Hz, 1H), 2.58 (dd, J=13.5, 7.0 Hz, 1H); $^{13}$C NMR (125 MHz, CDCl$_3$) δ 159.9, 158.4 (d, J$_{CF}$=247 Hz), 157.5, 141.7, 140.6, 136.4 (d, J$_{CF}$=9.5 Hz), 131.1, 129.1, 127.6, 125.3, 124.2, 117.5 (d, J$_{CF}$=17 Hz), 116.2 (d, J$_{CF}$=3.5 Hz), 108.7 (d, J$_{CF}$=26 Hz), 58.0, 53.7, 48.7, 34.7; HRMS (ESI–) m/z=386.0808 ([M–H]$^-$; calcd for C$_{18}$H$_{14}$N$_5$O$_2$ClF: 386.0809); [α]$_D$=+35.06 (c 0.12, CHCl$_3$).

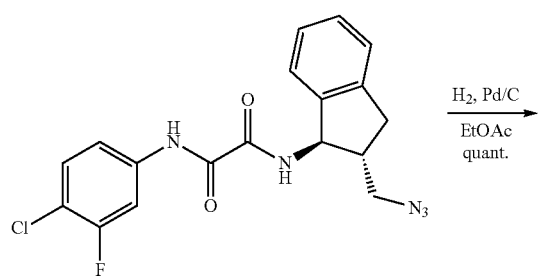

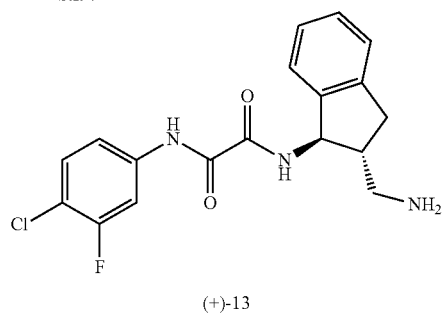

78

N¹-((1R,2R)-2-(Aminomethyl)-2,3-dihydro-1H-inden-1-yl)-N²-(4-chloro-3-fluorophenyl)-oxalamide [(+)-13]

To a solution of S.I. 7 (31 mg, 0.080 mmol) in EtOAc (4 mL) at room temperature, was added Pd—C (8 mg). The solution was stirred for 2.5 h at room temperature under H$_2$ balloon. The reaction mixture was filtered through celite, and the solvent was removed under reduced pressure to give 29 mg (quantitative yield) of (+)-13 as a white solid [$^1$H and $^{13}$C NMR data consistent with (±)-13]. [α]$_D$=+85.58 (c 0.18, DMSO).

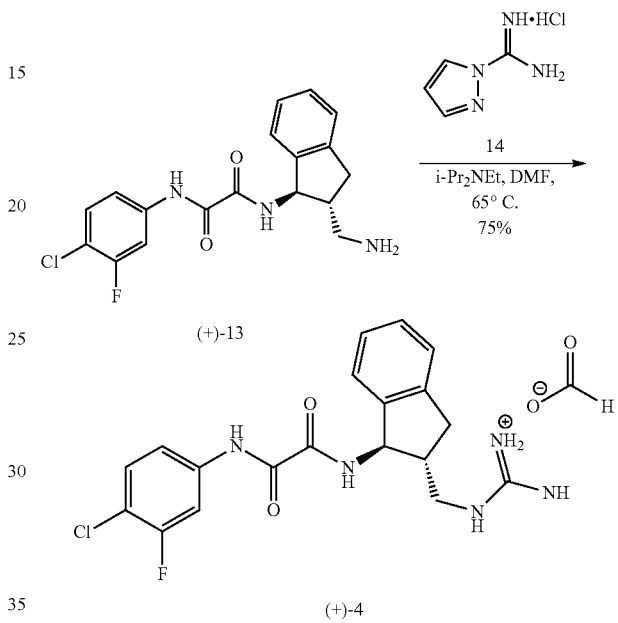

(+)-N¹-(4-Chloro-3-fluorophenyl)-N²-(trans-2-(guanidinomethyl)indan-1-yl)oxalamide formate salt [(+)-4]

To a solution of amine (+)-13 (25 mg, 0.080 mmol) in DMF (0.5 mL) was added i-Pr$_2$NEt (56 μL, 0.32 mmol), followed by carbamidine 13 (23 mg, 0.16 mmol). The mixture was then heated to 65° C. for 3 h, then cooled to room temperature and diluted with of CH$_3$CN and the product purified via HPLC to afford 27 mg (75%) of the formate salt of (+)-4 as a white solid ($^1$H and $^{13}$C NMR consistent with (±)-4). [α]$_D$=+45.05 (c 0.28, MeOH); 99% ee by SFC (Chiralpak IC, 40% (0.5% NEt$_3$/MeOH)/CO$_2$, 254 nm, 4 mL/min, 12 MPa): (1R,2R)-enantiomer [cf. (+)-4]: t$_r$=3.1 min (major) and (1S,2S)-enantiomer [cf. (–)-4]: t$_r$=4.2 min (minor).

Example 20

Synthetic Procedures

Figure 20:
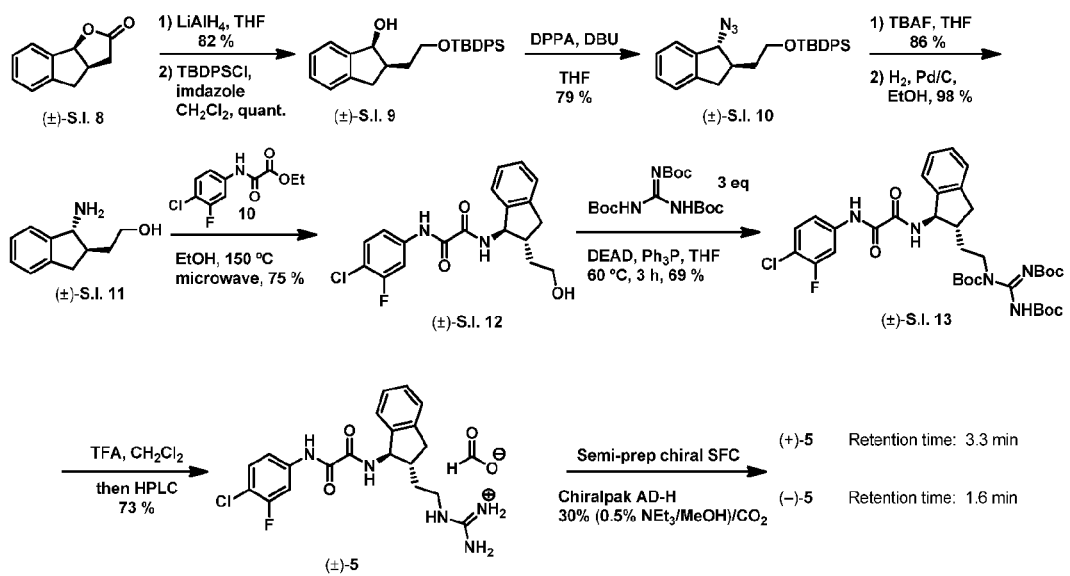
FIG. 20 depicts a synthesis of (+)-5 and separation of enantiomers from Example 20.

See FIG. 20.

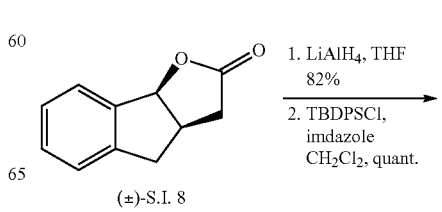

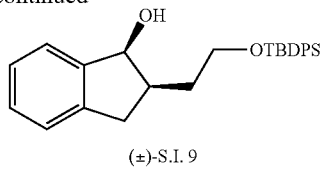

(±)-S.I. 9

(±)-2-(2-((tert-Butyldiphenylsilyl)oxy)ethyl)-2,3-dihydro-1H-inden-1-ol [(±)-S.I. 9]

A suspension of LiAlH$_4$ (673 mg, 17.7 mmol) in THF (10 mL) at 0° C. was added a solution of lactone (±)-S.I. 8[16] (298 mg, 7.86 mmol) in THF (10 mL). The reaction mixture was then warmed to room temperature and stirred for 3 h. The reaction was then quenched with the dropwise addition of 0.68 mL H$_2$O, after 5 minutes, this was followed by 0.68 mL of 15% aqueous NaOH, and then after another 5 minutes, an additional 1.3 mL of H$_2$O was added. The heterogeneous mixture was stirred until the solid aluminum salts became white and the precipitate was filtered off. The remaining solution was then concentrated and the residue purified by silica gel column chromatography using EtOAc/hexanes (20% to 33%) to provide the diol compound (863 mg, 82%) as a white solid. $^1$H NMR (500 MHz, CDCl$_3$) 7.43 (d, J=7.5 Hz, 1H), 7.20-7.30 (m, 3H), 5.13 (d, J=5.5 Hz, 1H), 3.82-3.92 (m, 1H), 3.78-3.81 (m, 1H), 2.97 (dd, J=15.8, 7.7 Hz, 1H), 2.82 (dd, J=15.8, 8.8 Hz, 1H), 2.46-2.52 (m, 1H), 2.01-2.09 (m, 1H), 1.83-1.89 (m, 1H). The diol (460 mg, 2.58 mmol) was dissolved in CH$_2$Cl$_2$ (20 mL) and the solution was cooled to 0° C. To this solution were added imidazole (193 mg, 2.83 mmol) and t-butyldiphenylsilyl chloride (0.73 mL, 2.85 mmol). The reaction mixture was then warmed to room temperature and stirred for 6 h. After the solution was concentrated, the residue was diluted with EtOAc, and washed with H$_2$O and brine. The organic layer was dried over anhydrous Na$_2$SO$_4$, concentrated under reduced pressure, and the residue was purified by silica gel column chromatography using EtOAc/hexanes (2% to 10%) to give (±)-S.I. 9 (1.07 g, 99%) as a colorless oil. $^1$H NMR (500 MHz, CDCl$_3$) δ 7.72-7.74 (m, 2H), 7.65-7.67 (m, 2H), 7.39-7.49 (m, 7H), 7.24-7.29 (m, 3H), 5.16 (d, J=4.5 Hz, 1H), 3.82-3.85 (m, 1H), 3.74-3.79 (m, 1H), 2.94 (dd, J=15.8, 7.8 Hz, 1H), 2.87 (s, 1H), 2.80 (dd, J=15.8, 8.8 Hz, 1H), 2.53-2.58 (m, 1H), 2.06-2.13 (m, 1H), 1.80-1.86 (m, 1H), 1.09 (s, 9H); $^{13}$C NMR (125 MHz, CDCl$_3$) δ 144.9, 143.6, 135.8, 133.3, 130.0, 128.6, 128.0, 126.8, 125.5, 124.9, 76.5, 63.8, 43.7, 37.0, 32.0, 27.0, 19.2; HRMS (ES+) m/z=439.2072 ([M+Na]$^+$; calcd for C$_{27}$H$_{32}$O$_2$SiNa: 439.2096).

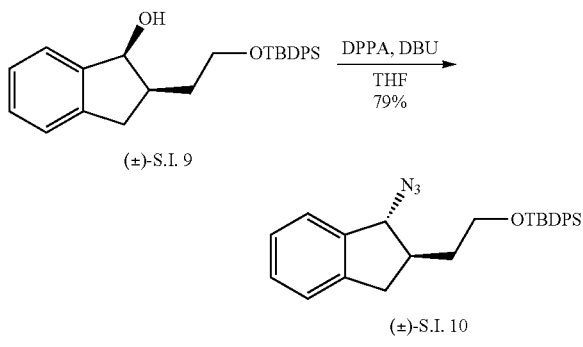

(2-((±)-1-Azido-2,3-dihydro-1H-inden-2-yl)ethoxy)(tert-butyl)diphenylsilane [(±)-S.I. 10]

To a solution of (±)-S.I. 9 (473 mg, 1.14 mmol) in THF (5 mL) at 0° C., was added diphenylphosphoryl azide (DPPA, 0.49 mL, 1.48 mmol). The solution was stirred at 0° C. for 5 min, and then DBU (0.22 mL, 1.47 mmol) was added. After 10 min, the solution was allowed to warm up to room temperature and stirred overnight. The reaction mixture was diluted with EtOAc, and washed with H$_2$O and brine. The organic layer was dried over anhydrous Na$_2$SO$_4$, concentrated under reduced pressure, and the residue was purified by silica gel column chromatography using 3% EtOAc/hexanes to give (±)-S.I. 10 (378 mg, 75%) as a colorless oil. $^1$H NMR (500 MHz, CDCl$_3$) δ 7.68 (dd, J=8.0, 1.5 Hz, 4H), 7.34-7.45 (m, 8H), 7.19-7.24 (m, 2H), 4.43 (d, J=6.5 Hz, 1H), 3.75-3.85 (m, 2H), 3.10 (dd, J=15.5, 7.5 Hz, 1H), 2.49-2.61 (m, 2H), 1.96-2.03 (m, 1H), 1.68-1.75 (m, 1H), 1.07 (s, 9H);
$^{13}$C NMR (125 MHz, CDCl$_3$) δ 142.6, 140.7, 135.8, 134.0, 129.9, 128.8, 127.9, 127.1, 125.2, 124.5, 71.2, 62.5, 44.3, 36.7, 29.9, 27.1, 19.4; HRMS (ES+) m/z=414.2260 ([M−N2]$^2$; calcd for C$_{27}$H$_{31}$NO: 414.2253).

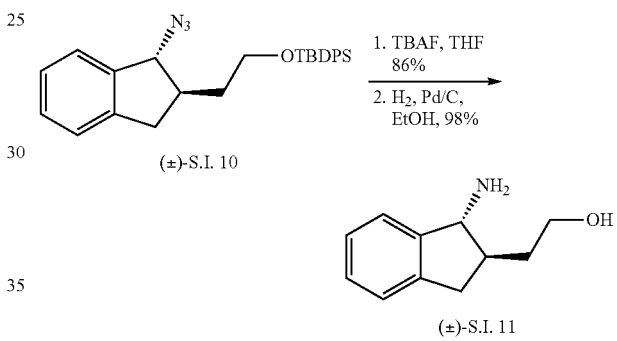

2-((±)-1-Amino-2,3-dihydro-1H-inden-2-yl)ethanol [(±)-S.I. 11]

To a solution of (±)-S.I. 10 (370 mg, 0.84 mmol) in THF (5 mL) at room temperature, was added a 1 M solution of TBAF (2.51 mL, 1.48 mmol) in THF. After stirring the mixture for 3 h, the reaction mixture was diluted with EtOAc, and washed with H$_2$O and brine. The organic layer was dried over anhydrous Na$_2$SO$_4$, concentrated under reduced pressure, and the residue was purified by silica gel column chromatography using EtOAc/hexanes (10% to 33%) to give the alcohol compound (147 mg, 86%) as a colorless oil. $^1$H NMR (500 MHz, CDCl$_3$) 7.37-7.38 (m, 1H), 7.23-7.28 (m, 3H), 4.49 (d, J=7.0 Hz, 1H), 3.83 (m, 2H), 3.20 (dd, J=15.5, 8.0 Hz, 1H), 2.62 (dd, J=15.8, 8.3 Hz, 1H), 2.51-2.55 (m, 1H), 1.95-2.02 (m, 1H), 1.80-1.87 (m, 1H). To a solution of the alcohol compound (147 mg, 0.72 mmol) in EtOH (3 mL) at room temperature, was added Pd—C (20 mg). The solution was stirred for 3 h at room temperature under H$_2$ balloon. The reaction mixture was filtered through celite, and the solvent was removed under reduced pressure to give (±)-S.I. 11 (126 mg, 98%) as a white solid. $^1$H NMR (500 MHz, CDCl$_3$) δ 7.19-7.24 (m, 4H), 3.94 (d, J=9.5 Hz, 1H), 3.81-3.85 (m, 1H), 3.68-3.73 (m, 1H), 3.01 (dd, J=15.5, 7.5 Hz, 1H), 2.62 (dd, J=15.5, 10.5 Hz, 1H), 1.98-2.04 (m, 2H), 1.84-1.89 (m, 1H); $^{13}$C NMR (125 MHz, CDCl$_3$) δ 147.2, 141.7, 127.6, 126.9, 124.6, 122.6, 62.6, 62.0, 51.9, 37.9, 37.7; LCMS: m/z=178.2 (M+H)'.

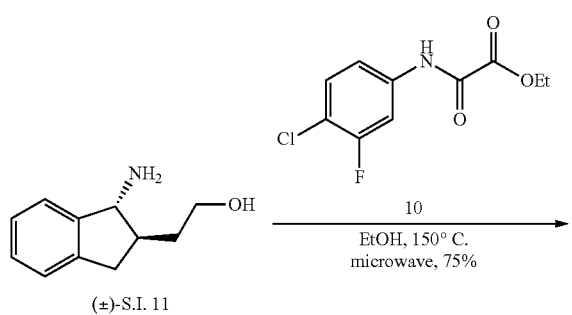

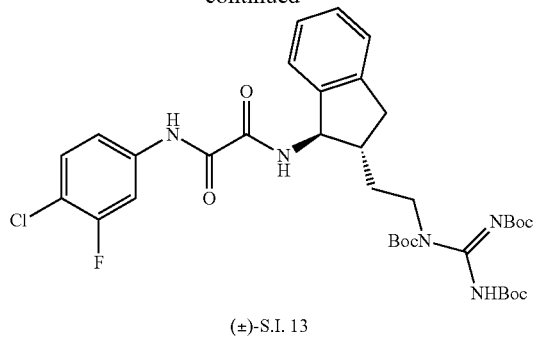

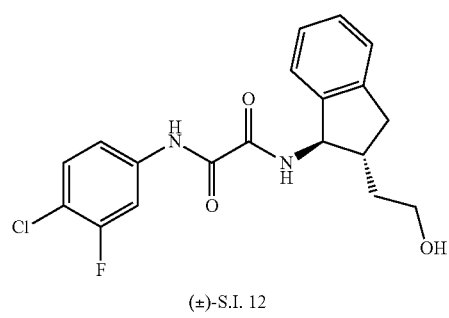

(±)-N¹-(4-Chloro-3-fluorophenyl)-N²-2-(2-hydroxyethyl)-2,3-dihydro-1H-inden-1-yl)oxalamide [(±)-S.I. 12]

A solution of amino alcohol (±)-S.I. 11 (61 mg, 0.35 mmol) in EtOH (1.5 mL) was transferred into a vial containing oxalate 10 (87 mg, 0.35 mmol), the vial was then sealed and the mixture was heated to 150° C. in a microwave reactor for 1 h. The reaction mixture was purified by silica gel column chromatography using EtOAc/hexanes (20% to 100%) to give (±)-S.I. 12 (111 mg, 83%) as a white solid. $^1$H NMR (500 MHz, DMSO-$d_6$) δ 11.10 (s, 1H), 9.32 (d, J=9.0 Hz, 1H), 7.98 (dd, J=12.0, 2.5 Hz, 1H), 7.76 (dd, J=9.0, 1.5 Hz, 1H), 7.57 (t, J=8.8 Hz, 1H), 7.14-7.22 (m, 3H), 7.11 (d, J=7.0 Hz, 1H), 5.09 (t, J=9.0 Hz, 1H), 4.47 (t, J=5.0 Hz, 1H), 3.47-3.54 (m, 1H), 3.08 (dd, J=14.5, 7.0 Hz, 1H), 2.50-2.63 (m, 2H), 1.84 (m, 1H), 1.65 (m, 1H); $^{13}$C NMR (125 MHz, DMSO-$d_6$) δ 160.0, 159.0, 156.9 (d, $J_{CF}$=243 Hz), 143.0, 142.0, 138.4 (d, $J_{CF}$=10 Hz), 130.6, 127.4, 126.3, 124.5, 123.3, 117.3 (d, $J_{CF}$=3.1 Hz), 114.4 (d, $J_{CF}$=17 Hz), 108.5 (d, $J_{CF}$=25 Hz), 59.8, 59.6, 43.6, 36.3, 36.1; LCMS: m/z=377.1 (M+H)⁺.

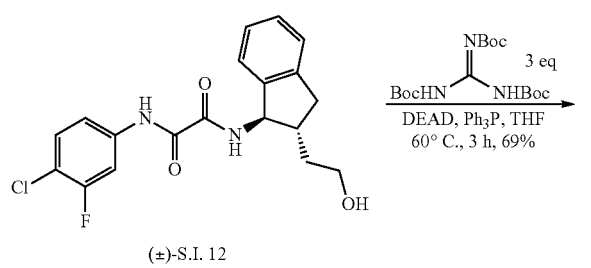

(±)-Tri-Boc-guanidine compound [(±)-S.I. 13].[17]

To a suspension of alcohol (±)-S.I. 12 (28 mg, 0.074 mmol), tri-Boc-guanidine (80 mg, 0.22 mmol), and Ph₃P (29 mg, 0.11 mmol), was added diethyldiazocarboxylate (DEAD, 17 µL, 0.11 mmol) at room temperature. The reaction mixture was heated to 60° C., and stirred for 3 h. The reaction mixture was concentrated under reduced pressure, the residue was purified by silica gel column chromatography using EtOAc/hexanes (10% to 20%) to give a mixture of (±)-S.I. 14 and tri-Boc-guanidine reagent. The mixture was suspended in hexanes, and then filtered off to remove precipitate. The residue was concentrated to yield (±)-S.I. 13 (37 mg, 69%) as a white crystalline solid. $^1$H NMR (500 MHz, CDCl₃) δ 10.56 (br. s, 1H), 9.48 (s, 1H), 7.72-7.78 (m, 2H), 7.14-7.35 (m, 6H), 5.15 (t, J=8.8 Hz, 1H), 3.87-3.93 (m, 2H), 3.22 (dd, J=16.0, 8.0 Hz, 1H), 2.65 (dd, J=16.0, 9.0 Hz, 1H), 2.38 (m, 1H), 2.11 (m, 1H), 1.85 (m, 1H), 1.51 (s, 27H); LCMS: m/z=718.3 (M+H)⁺.

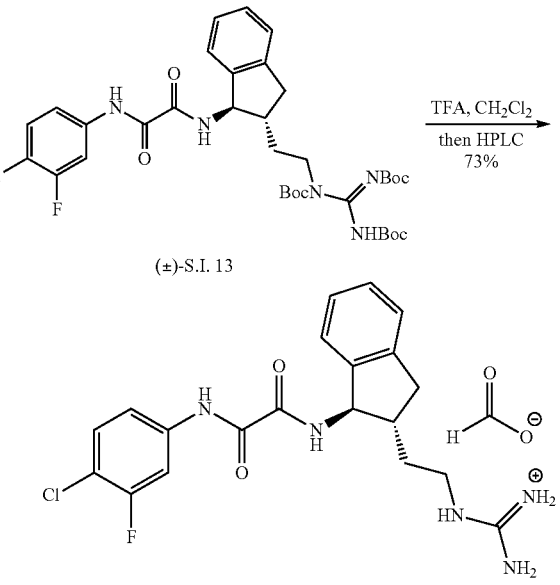

(±)-N¹-(4-Chloro-3-fluorophenyl)-N²-(trans-2-(2-guanidinoethyl)indan-1-yl)oxalamide formate salt [(±)-5]

To a solution of (±)-S.I. 13 (57 mg, 0.079 mmol) in CH₂Cl₂ (31 mL) at room temperature, was added trifluoroacetic acid (0.3 mL). The reaction mixture was stirred at room temperature for 4 h, then concentrated and diluted with of CH$_3$CN and the product purified via HPLC to afford (±)-5 (27 mg, 73%) as a white solid. $^1$H NMR (500 MHz, DMSO-d$_6$) δ 11.08 (br. s, 1H), 9.41 (d, J=9.0 Hz, 1H), 8.42 (s, 1H), 8.12 (br s, 1H), 7.97 (dd, J=12.0, 2.0 Hz, 1H), 7.76 (d, J=9.0 Hz, 1H), 7.59 (t, J=9.0 Hz, 1H), 7.35 (br s, 4H), 7.11-7.34 (m, 4H), 5.10 (t, J=9.0 Hz, 1H), 3.07-3.21 (m, 3H), 2.50-2.63 (m, 2H), 1.88 (m, 1H), 1.72 (m, 1H); $^{13}$C NMR (125 MHz, CD$_3$OD) δ 161.9, 160.0, 159.3 (d, J$_{CF}$=244 Hz), 158.8, 143.2, 143.1, 139.3 (d, J$_{CF}$=10 Hz), 131.9, 129.4, 128.1, 125.9, 124.8, 118.2 (d, J$_{CF}$=3.3 Hz), 117.4 (d, J$_{CF}$=18 Hz), 110.0 (d, J$_{CF}$=26 Hz), 61.4, 47.0, 41.3, 37.4, 33.7; HRMS (ES+) m/z 418.1450 ([M+H]; calcd for C$_{20}$H$_{22}$N$_5$O$_2$FCl: 418.1446). The formate counterion was not observed under the HRMS conditions. The enantiomers were separated by semi-preparative chiral SFC (Chiralpak AD-H (10×250 mm, 5 μm), 30% (0.5% NEt$_3$/MeOH)/CO$_2$, 254 nm, 4 mL/min, 12 MPa). The resulting enantiomers were analyzed by analytical chiral SFC (Chiralpak AD-H, 40% (0.5% NEt$_3$/MeOH)/CO$_2$, 254 nm, 4 mL/min, 12 MPa; (−)-5: t$_r$=1.6 min and (+)-5: t$_r$=3.3 min) and the e.e. of both enantiomers was determined as >96%; (−)-5: [α]$_D$=−138.74 (c 0.085, MeOH) and (+)-5: [α]$_D$=+136.85 (c 0.085, MeOH). The absolute stereochemistry of 5 was assigned based on analogy to previously determined compounds (+)-4 and (+)-12.

Example 21

Synthetic Procedures

Figure 11:
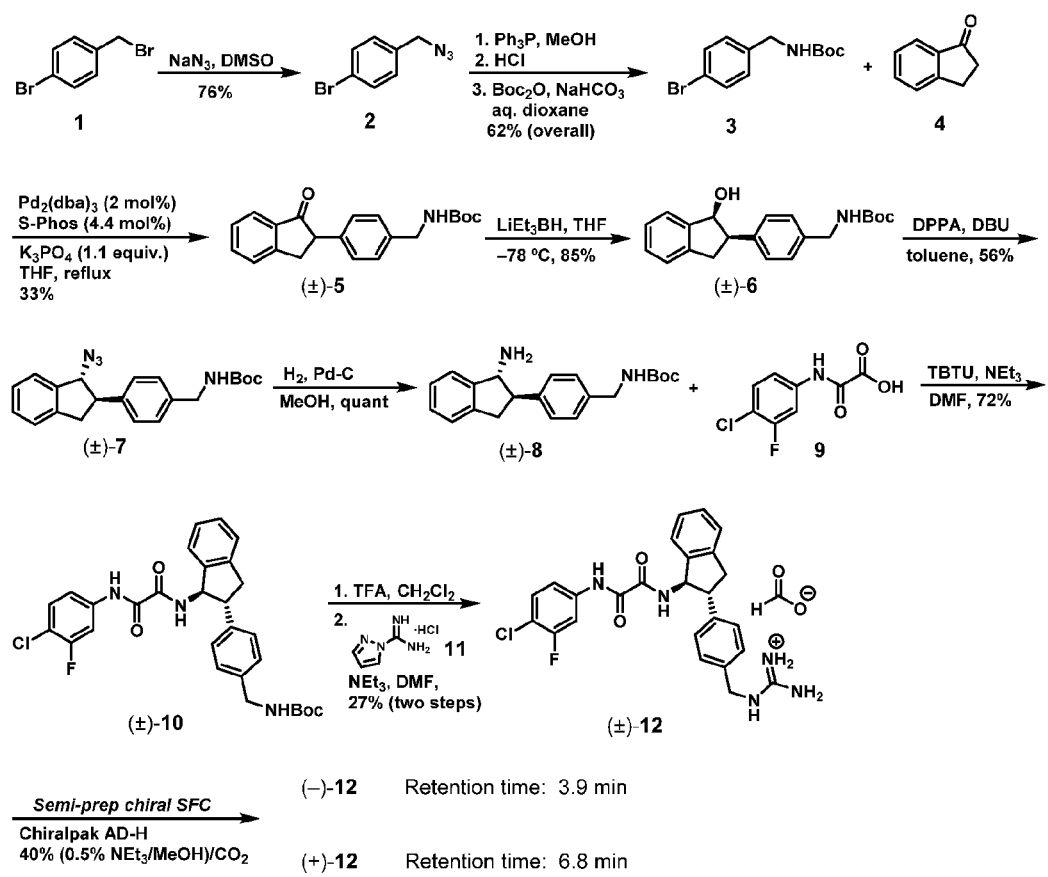
FIG. 11 depicts a synthetic scheme for two compounds of the invention. See Example 21.

See FIG. 11.

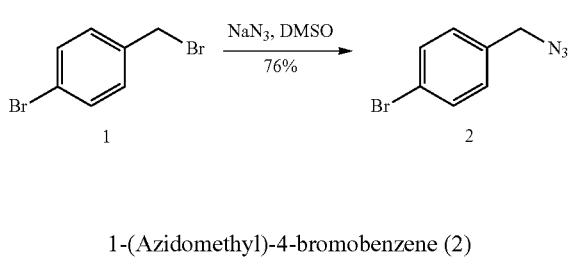

1-(Azidomethyl)-4-bromobenzene (2)

To a solution of 4-bromobenzylbromide 1 (2.95 g, 11.8 mmol) in DMSO (5 mL) at room temperature, was added NaN$_3$ (1.53 g, 23.5 mmol). The solution was heated to 80° C. and stirred for 1 h at this temperature. The reaction mixture was diluted with EtOAc, and washed with H$_2$O and brine. The organic layer was dried over anhydrous Na$_2$SO$_4$, concentrated under reduced pressure, and the residue was purified by silica gel column chromatography using EtOAc/hexanes (10%) to give 1.88 g (76%) of 2 as a colorless oil. $^1$H NMR spectra was consistent with literature data. Shi, H.; Liu, J.; Geng, J.; Tang, B. Z.; Liu, B. *J. Am. Chem. Soc.* 2012, 134, 9569.

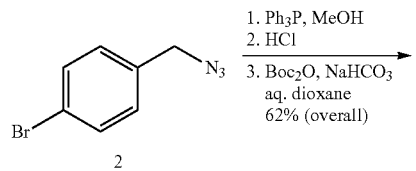

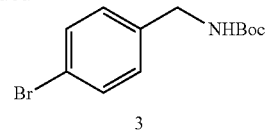

tert-Butyl(4-bromobenzyl)carbamate (3)

To a solution of 1-(azidomethyl)-4-bromobenzene 2 (1.88 g, 8.95 mmol) in MeOH (10 mL) at room temperature, was added Ph$_3$P (3.52 g, 13.4 mmol). The solution was heated to reflux and stirred for 1 h at this temperature. The reaction mixture was cooled to room temperature and concentrated under reduced pressure. The residue was dissolved in CH$_2$Cl$_2$, and 4 M HCl (2.5 mL) in dioxane was added. The resulting precipitate was filtered and washed with hexanes to give crude amine compound as the HCl salt. This amine was used for the next step without further purification. The crude amine hydrochloride salt was suspended in dioxane (5 mL) and saturated aqueous NaHCO$_3$ solution (10 mL) at room temperature. After addition of Boc$_2$O (3.90 g, 17.9 mmol), the reaction mixture was stirred for 3 h at room temperature. The reaction mixture was diluted with EtOAc, and washed with H$_2$O and brine. The organic layer was dried over anhydrous Na$_2$SO$_4$, concentrated under reduced pressure, and the residue was purified by silica gel column chromatography using EtOAc/hexanes (10%) to give 1.60 g (62%) of 3 as a white solid. $^1$H NMR spectra was consistent with literature data. Howell, S. J.; Spencer, N.; Philip D. *Tetrahedron* 2001, 57, 4945.

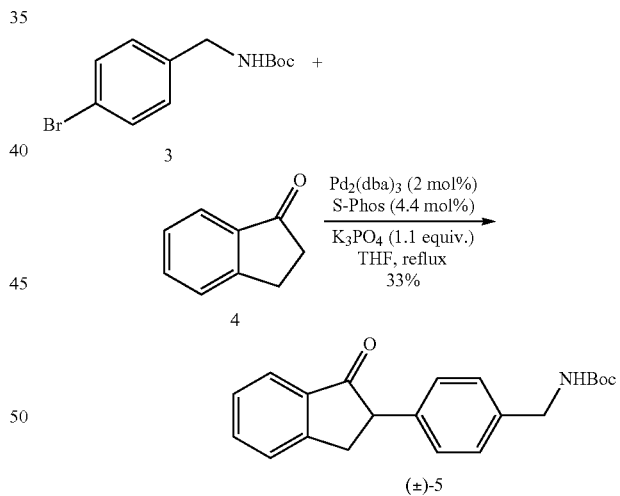

(±)-tert-Butyl (4-(1-oxo-2,3-dihydro-1H-inden-2-yl) benzyl)carbamate ((±)-5)

A mixture of Pd$_2$(dba)$_3$ (20 mg, 0.020 mmol), S-Phos (19 mg, 0.046 mmol, 0.12 eq.), K$_3$PO$_4$ (249 mg, 1.17 mmol), 1-indanone (170 mg, 0.12 mmol, 0.12 eq.), and arylbromide 3 (1.2 mmol, 1.2 eq.) in anhydrous THF (10 mL) was degassed and purged with nitrogen (3 times). The resulting mixture was then heated to reflux overnight under nitrogen. The reaction mixture was diluted with EtOAc, and washed with H$_2$O and brine. The organic layer was dried over anhydrous Na$_2$SO$_4$, concentrated under reduced pressure, and the residue was purified by silica gel column chromatography using EtOAc/hexanes (10%) to give 120 mg (33%) of (±)-5 as a yellow oil. ¹H NMR (CDCl₃, 500 MHz) δ 7.80 (d, J=7.5 Hz, 1H), 7.64 (m, 1H), 7.42 (t, J=7.5 Hz, 1H), 7.23 (d, J=8.0 Hz, 2H), 7.14 (d, J=8.0 Hz, 2H), 4.89 (s, 1H), 4.27 (d, J=5.5 Hz, 2H), 3.87 (dd, J=8.3, 4.3 Hz, 1H), 3.68 (dd, J=17.3, 8.3 Hz, 1H), 3.24 (dd, J=17.5, 4.0 Hz, 1H), 1.45 (s, 9H); ¹³C NMR (CDCl₃, 125 MHz) δ 206.1, 156.0, 153.8, 138.9, 137.9, 136.3, 135.2, 128.3, 128.2, 127.9, 126.6, 124.7, 79.6, 53.3, 44.5, 35.9, 28.6.

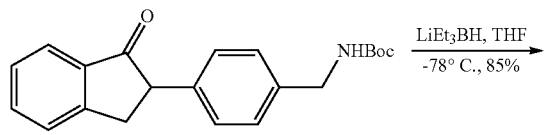

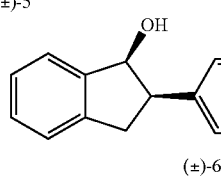

(±)-tert-Butyl (4-((cis-1-hydroxy-2,3-dihydro-1H-inden-2-yl)benzyl)carbamate ((±)-6)

To a solution of (±)-5 (120 mg, 0.36 mmol) in THF (5 mL) at −78° C. was added 1 M solution of LiEt₃BH (0.89 mL) in THF. The solution was stirred for 1 h at this temperature, then warmed to room temperature. The reaction mixture was quenched by MeOH, then diluted with EtOAC. The reaction mixture was washed with water and brine. The organic layer was dried over anhydrous Na₂SO₄, concentrated under reduced pressure, and the residue was purified by silica gel column chromatography using EtOAc/hexanes (20% to 50%) to give 103 mg (85%) of (±)-6 as a colorless oil. ¹H NMR (CDCl₃, 500 MHz) δ 7.44 (d, J=7.0 Hz, 1H), 7.24-7.35 (m, 7H), 5.23 (d, J=5.0 Hz, 1H), 4.89 (s, 1H), 4.29 (d, J=5.5 Hz, 2H), 3.72 (q, J=7.2 Hz, 1H), 3.37 (dd, J=16.0, 8.0 Hz, 1H), 3.21 (dd, J=15.8, 7.8 Hz, 1H), 1.46 (s, 9H); ¹³C NMR (CDCl₃, 125 MHz) δ 156.1, 143.9, 143.3, 138.6, 137.9, 129.3, 128.9, 127.9, 127.2, 125.3, 125.0, 79.7, 77.5, 51.0, 44.5, 36.0, 28.6.

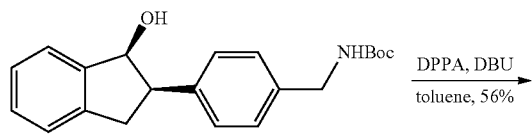

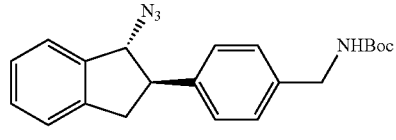

(±)-tert-Butyl (4-((trans-1-azido-2,3-dihydro-1H-inden-2-yl)benzyl)carbamate ((±)-7)

To a solution of (±)-6 (25 mg, 0.074 mmol) in toluene (1 mL) at 0° C., was added diphenylphosphoryl azide (DPPA, 48 μL, 0.22 mmol). The solution was stirred at 0° C. for 5 min, and then DBU (33 μL, 0.22 mmol) was added. After 10 min, the solution was allowed to warm up to room temperature and stirred for 4 h. The reaction mixture was diluted with EtOAc, and washed with H₂O and brine. The organic layer was dried over anhydrous Na₂SO₄, concentrated under reduced pressure, and the residue was purified by silica gel column chromatography using EtOAc/hexanes (10% to 20%) to give (±)-7 (15 mg, 56%) as a colorless oil. ¹H NMR (CDCl₃, 500 MHz) δ 7.25-7.40 (m, 8H), 4.84 (m, 2H), 4.31 (d, J=5.5 Hz, 2H), 3.58 (q, J=8.0 Hz, 1H), 3.42 (dd, J=16.0, 8.5 Hz, 1H), 3.09 (dd, J=16.0, 8.5 Hz, 1H), 1.47 (s, 9H); ¹³C NMR (CDCl₃, 125 MHz) δ 156.1, 141.9, 141.1, 140.3, 138.1, 129.1, 128.1, 127.8, 127.5, 125.0, 124.5, 79.7, 72.5, 52.8, 44.5, 38.7, 28.6.

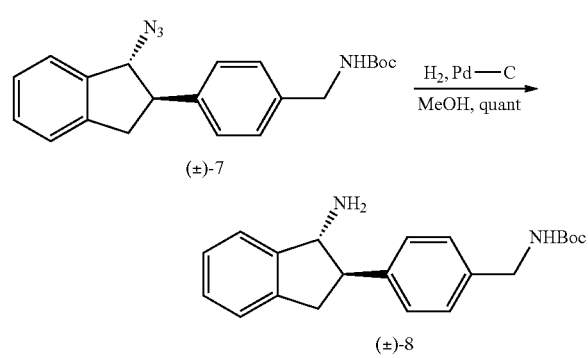

(±)-tert-Butyl (4-(trans-1-amino-2,3-dihydro-1H-inden-2-yl)benzyl)carbamate ((±)-8)

To a solution of (±)-7 (15 mg, 0.047 mmol) in MeOH (2 mL) at room temperature, was added Pd—C (4 mg). The solution was stirred for 1 h at room temperature under H₂ balloon. The reaction mixture was filtered through celite, and the solvent was removed under reduced pressure to give (±)-8 (14 mg, quant.) as a white solid. ¹H NMR (CDCl₃, 500 MHz) δ 7.21-7.40 (m, 8H), 4.89 (s, 1H), 4.39 (d, J=8.5 Hz, 1H), 4.29 (d, J=5.0 Hz, 2H), 3.32 (dd, J=15.5, 7.5 Hz, 1H), 3.21 (q, J=8.5 Hz, 1H), 3.05 (dd, J=15.5, 9.5 Hz, 1H), 1.46 (s, 9H); ¹³C NMR (CDCl₃, 125 MHz) δ 156.1, 146.1, 141.8, 141.4, 137.6, 128.2, 128.0, 127.7, 127.1, 124.6, 123.6, 79.7, 64.7, 59.0, 44.6, 38.9, 28.6.

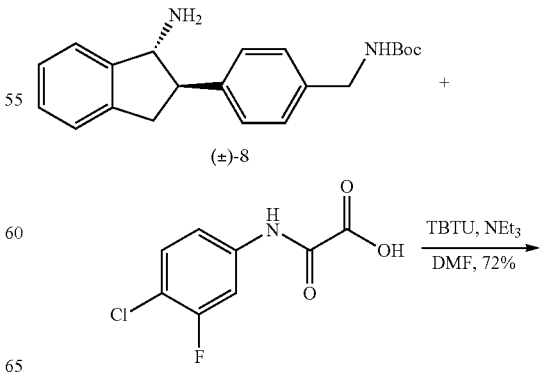

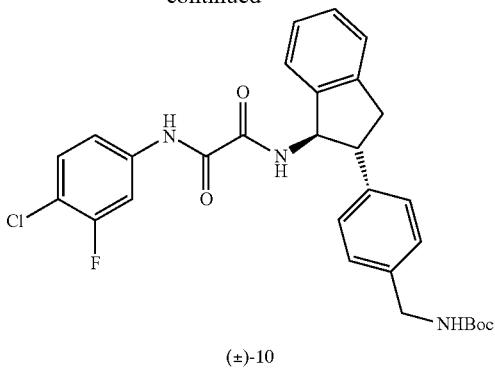

(±)-10

(±)-tert-Butyl (4-(trans-1-(2-((4-chloro-3-fluorophenyl)amino)-2-oxoacetamido)-2,3-dihydro-1H-inden-2-yl)benzyl)carbamate ((±)-10)

To a solution of amine (±)-8 (14 mg, 0.041 mmol), 9 (14 mg, 0.064 mmol), and TBTU (20 mg, 0.062 mmol) in DMF (0.5 mL), was added triethylamine (11 μL, 0.063 mmol) at room temperature. The reaction mixture was stirred overnight at room temperature. The reaction mixture was diluted with EtOAc, and washed with $H_2O$, 1 N HCl, saturated aqueous $NaHCO_3$, and brine. The organic layer was dried over anhydrous $Na_2SO_4$, concentrated under reduced pressure, and the residue was purified by silica gel column chromatography using 33% EtOAc/hexanes to give (±)-10 (16 mg, 72%) as a white solid. $^1$H NMR ($CDCl_3$, 500 MHz) δ 7.85 (d, J=9.5 Hz, 1H), 7.70 (dd, J=10.5, 2.0 Hz, 1H), 7.19-7.36 (m, 10H), 5.63 (t, J=9.0 Hz, 1H), 4.86 (s, 1H), 4.29 (d, J=5.5 Hz, 2H), 3.51 (q, J=9.0 Hz, 1H), 3.37 (dd, J=15.5, 8.0 Hz, 1H), 3.09 (dd, J=15.5, 9.5 Hz, 1H), 1.45 (s, 9H); $^{13}$C NMR ($CDCl_3$, 125 MHz) δ 159.6, 158.2 (d, $J_{CF}$=246 Hz), 157.6, 156.1, 141.7, 141.1, 140.3, 138.0, 136.4 (d, $J_{CF}$=8.8 Hz), 131.0, 130.1, 128.9, 128.0, 127.8, 127.5, 125.0, 124.0, 117.3 (d, $J_{CF}$=18 Hz), 116.2 (d, $J_{CF}$=3.9 Hz), 108.6 (d, $J_{CF}$=26 Hz), 79.7, 61.6, 54.1, 44.5, 39.1, 28.6.

mL). The reaction mixture was stirred at room temperature for 1 h, then concentrated under reduced pressure. The residue was diluted with EtOAc then washed with saturated aqueous $NaHCO_3$ solution and brine. The organic layer was dried over anhydrous $Na_2SO_4$, concentrated under reduced pressure to give a crude amine compound. This compound was used for the next step without further purification.

To a solution of the amine in DMF (0.5 mL) was added i-$Pr_2$NEt (25 μL, 0.14 mmol), followed by carbamidine 11 (11 mg, 0.075 mmol). The mixture was then heated to 70° C. overnight, then cooled to room temperature and diluted with of $CH_3$CN and the product purified via HPLC to afford 8 mg (27%, two steps) of the formate salt of (±)-12 as a white solid. $^1$H NMR ($CD_3OD$, 500 MHz) δ 8.53 (s, 1H), 7.84 (dd, J=11.5, 2.0 Hz, 1H), 7.41-7.49 (m, 4H), 7.25-7.31 (m, 5H), 7.18 (d, J=7.0 Hz, 1H), 5.62 (d, J=9.5 Hz, 1H), 4.38 (s, 2H), 3.71 (q, J=9.2 Hz, 1H), 3.37 (dd, J=15.5, 8.0 Hz, 1H), 3.12 (dd, J=15.5, 10.5 Hz, 1H); $^{13}$C NMR ($CD_3OD$, 125 MHz) δ 161.7, 159.9, 159.3 (d, $J_{CF}$=243 Hz), 158.9, 143.2, 143.1, 142.8, 139.2 (d, $J_{CF}$=10 Hz), 136.3, 131.8, 129.4, 129.4, 128.8, 128.3, 125.8, 124.7, 118.2 (d, $J_{CF}$=3.5 Hz), 117.3 (d, $J_{CF}$=18 Hz), 109.9 (d, $J_{CF}$=26 Hz), 62.8, 54.3, 45.9, 39.7; LCMS: m/z=480.2 (M+H)'. The formate counterion was not observed under the LCMS conditions.

The enantiomers were separated by semi-preparative chiral SFC (Chiralpak AD-H (10×250 mm, 5 μm), 40% (0.5% $NEt_3$/MeOH)/$CO_2$, 254 nm, 4 mL/min, 12 MPa). The resulting enantiomers were analyzed by analytical chiral SFC (Chiralpak AD-H, 40% (0.5% $NEt_3$/MeOH)/$CO_2$, 254 nm, 4 mL/min, 12 MPa; (−)-12: $t_r$=3.9 min and (+)-12: $t_r$=6.8 min) and the e.e. of both enantiomers was determined as >99%; (−)-5:

$$[\alpha]\frac{19}{D} = -75.2(c\ 0.054, \text{MeOH})$$

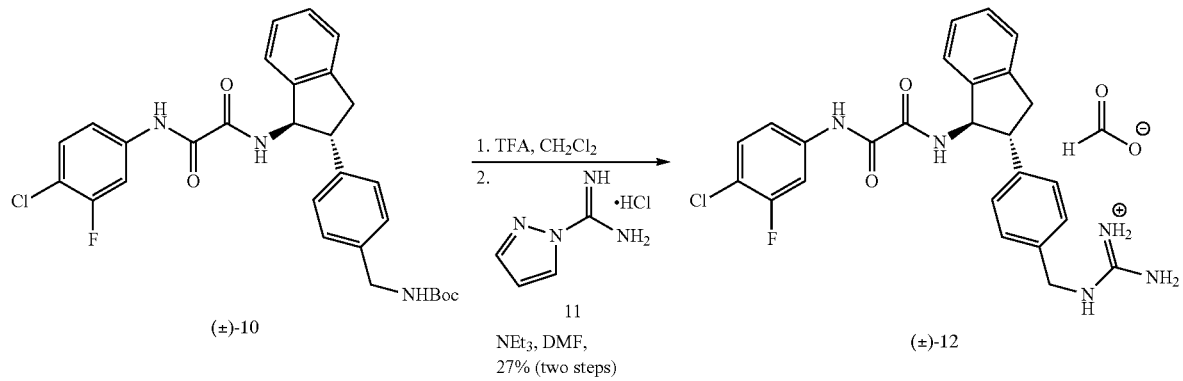

(±)-tert-Amino((4-((trans-1-(2-((4-chloro-3-fluorophenyl)amino)-2-oxoacetamido)-2,3-dihydro-1H-inden-2-yl)benzyl)amino)methaniminium formate ((±)-12)

To a solution of (±)-10 (30 mg, 0.056 mmol) in $CH_2Cl_2$ (1 mL) at room temperature, was added trifluoroacetic acid (0.3 and (+)-5:

$$[\alpha]\frac{19}{D} = +70.5(c\ 0.062, \text{MeOH}).$$

The absolute stereochemistry of 12 was assigned based on analogy to previously determined compounds.

Example 22

Figure 12A:
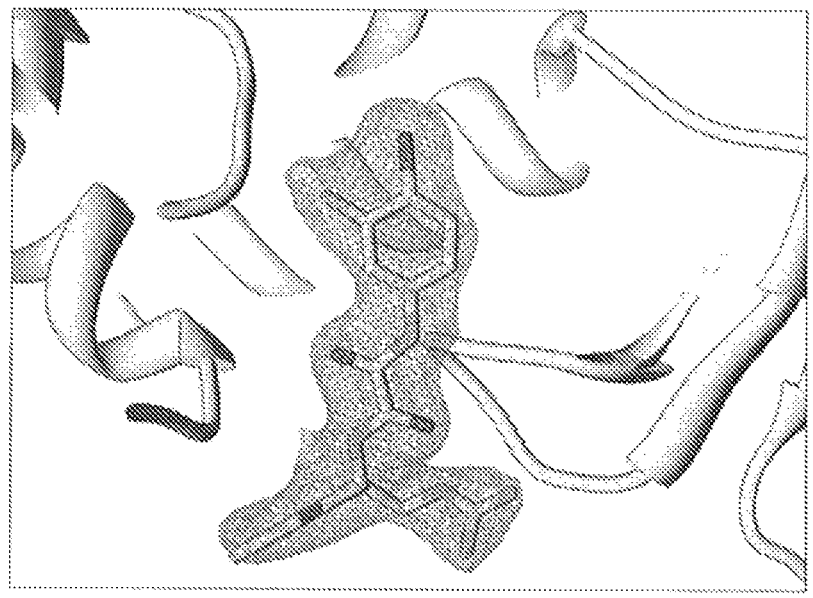
FIG. 12 depicts the X-ray crystal structure of a compound of the invention in gp120 Glade A/E$_{93TH057}$. A) $2F_o$-$F_c$ electron density at 2.5 Å encompassing DMJ-II-121-R, R. Phe43$_{gp120}$ pocket residues are diagramed in ribbon form. The density is contoured to 1σ and represented as blue mesh. B) Stick drawing of ligand interaction in the gp120 binding-site. Hydrogen-bonds are highlighted in dashed lines. Residues participating in hydrogen-bonded interactions are labeled with amino acid and residue number.
Figure 12B:
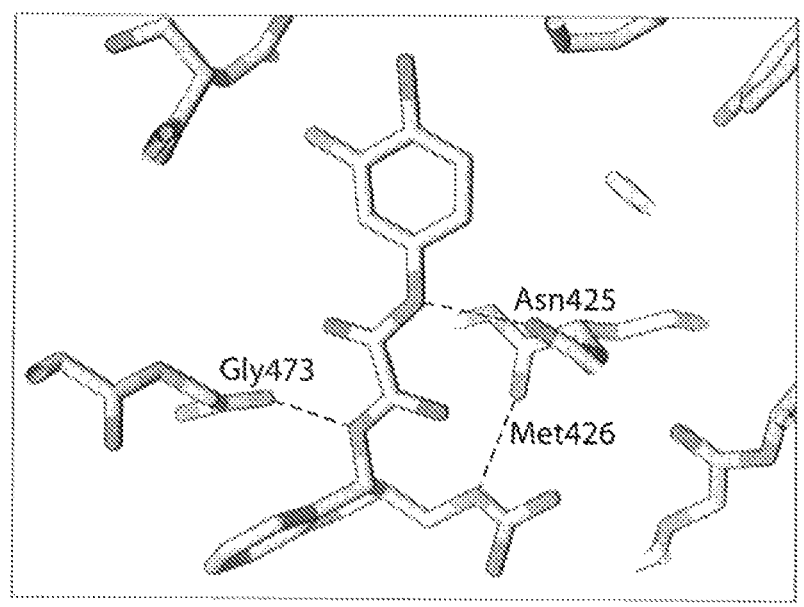

See FIG. 12.

(−)-12, as synthesized in Example 21, displayed a R5T4 IC$_{50}$ of 8 μM for YU2 and 100 μM for AMLV.

Example 23

Synthetic Procedure

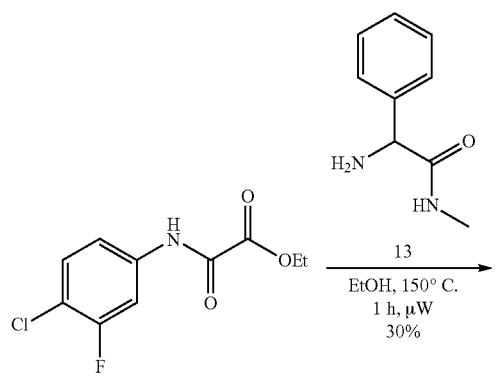

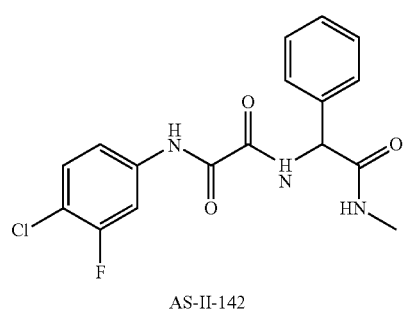

AS-II-142

N$^1$-(4-chloro-3-fluorophenyl)-N$^2$-(2-(methylamino)-2-oxo-1-phenylethyl)oxalamide (AS-II-142)

To a solution containing ester 1 (325 mg, 1.33 mmol) in 2 mL of EtOH contained in microwave reaction vial for 2-5 mL size which could be sealed with a Teflon® cap was added amine 13 (218 mg, 1.327 mmol). The tube was briefly flushed with an Argon stream (approximately 30 sec) and sealed. The reaction was heated to 150° C. for 1 hour in microwave and then allowed to cool to room temperature. The resulting crude products were purified by recrystallization from EtOH and washed with hexanes to afford 144.7 mg (0.398 mg, 30%) of the title compound AS-II-142. $^1$H NMR (500 MHz, DMSO-d$_6$) δ 11.04 (s, 1H), 8.86 (d, J=8.0 Hz, 1H), 8.34 (dd, J=4.3, 9.0 Hz, 1H), 7.91 (dd, J=2.3, 11.8 Hz, 1H), 7.72-7.69 (m, 1H), 7.58 (t, J=8.7 Hz, 1H), 7.44-7.42 (m, 2H), 7.38-7.35 (m, 2H), 7.32-7.29 (m, 1H), 5.44 (d, J=8.0 Hz, 1H), 2.62 (d, J=4.5 Hz, 3H). $^{13}$C NMR (125 MHz, DMSO-d$_6$) δ 169.0, 158.6, 158.5, 156.8 (d, J$_{CF}$=242.7 Hz), 138.0 (d, J$_{CF}$=10.0 Hz), 137.9, 130.5, 128.5, 127.9, 127.0, 117.5 (d, J$_{CF}$=3.0 Hz), 114.6 (d, J$_{CF}$=17.6 Hz), 108.6 (d, J$_{CF}$=25.6 Hz), 56.4, 25.7. HRMS (ES+) m/z 386.0701 [(M+Na); calcd for C$_{17}$H$_{15}$N$_3$O$_3$ClFNa: 386.0684].

Example 24

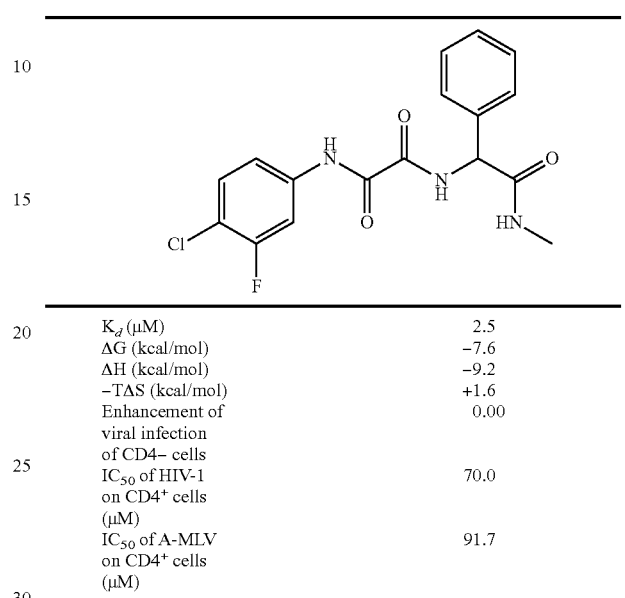

| | |
|---|---|
| K$_d$ (μM) | 2.5 |
| ΔG (kcal/mol) | −7.6 |
| ΔH (kcal/mol) | −9.2 |
| −TΔS (kcal/mol) | +1.6 |
| Enhancement of viral infection of CD4− cells | 0.00 |
| IC$_{50}$ of HIV-1 on CD4$^+$ cells (μM) | 70.0 |
| IC$_{50}$ of A-MLV on CD4$^+$ cells (μM) | 91.7 |

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A compound of Formula VII

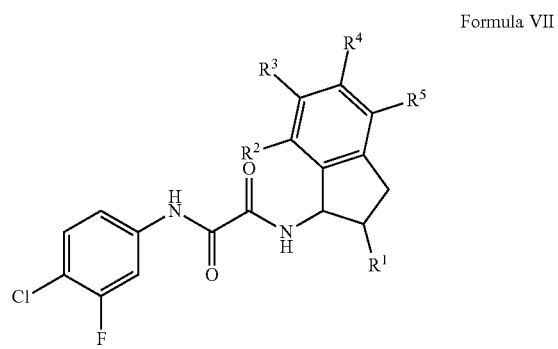

Formula VII or a pharmaceutically acceptable salt or solvate thereof, wherein
R¹ is

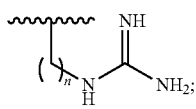

R² is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R³ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁴ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo;

R⁵ is —H, optionally substituted alkyl, optionally substituted alkenyl, optionally substituted alkynyl, optionally substituted aryl, optionally substituted heteroaryl, hydroxy, optionally substituted alkoxy, optionally substituted amino, or halo; and n is 0, 1, 2, 3, 4, or 5.

2. The compound of claim 1, wherein n is 1 or 2.

3. The compound of claim 1, which is a compound of Formula IV

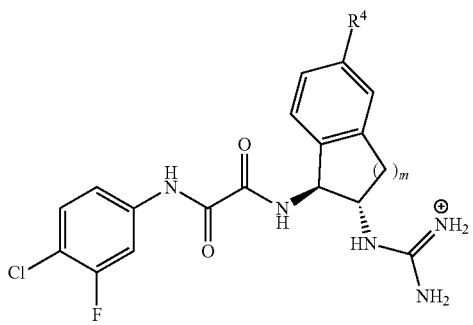

Formula IV or a pharmaceutically acceptable salt or solvate thereof, wherein m is 1.

4. The compound of claim 1, which is a compound of Formula V

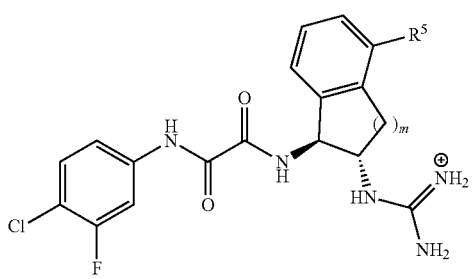

Formula V or a pharmaceutically acceptable salt or solvate thereof, wherein m is 1.

5. The compound of claim 1, which is a compound of Formula VI

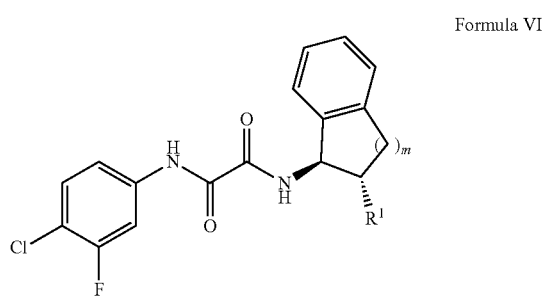

Formula VI or a pharmaceutically acceptable salt or solvate thereof, wherein m is 1.

6. The compound of claim 1, which is

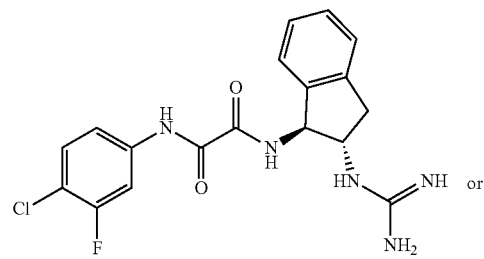

or

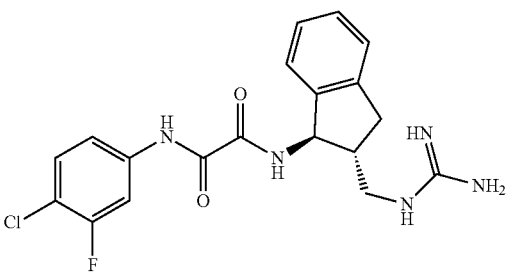

or a pharmaceutically acceptable salt thereof.

7. A pharmaceutical composition comprising a compound of claim 1 or a pharmaceutically acceptable salt thereof and a pharmaceutically acceptable carrier.

8. A method of activating HIV exterior envelope glycoprotein gp120, inhibiting transmission of HIV to a cell, or inhibiting the progression of HIV infection in a cell comprising the step of:

contacting HIV with an effective amount of a compound of claim 1, thereby activating HIV exterior envelope glycoprotein gp120, inhibiting transmission of HIV to said cell, or inhibiting progression of HIV in said cell.

9. The method of claim 8, wherein the method is a method of inhibiting transmission of HIV to a cell or inhibiting the progression of HIV infection in a cell, further comprising the step of:

contacting HIV with an effective amount of an exogenous ligand mimicking the chemokine receptor expressed on said cell.

10. The compound of claim 1, wherein $R^1$ is

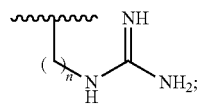

one of $R^2$, $R^3$, $R^4$, and $R^5$ is halo; three of $R^2$, $R^3$, $R^4$, and $R^5$ are —H; and n is 1.

11. The compound of claim 1, wherein $R^1$ is

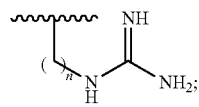

one of $R^2$ and $R^3$ is halo; one of $R^2$ and $R^3$ is —H; $R^4$ is —H; $R^5$ is —H; and n is 1.

12. The compound of claim 1, wherein $R^1$ is

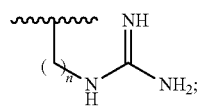

$R^2$ is —H; $R^3$ is halo; $R^4$ is —H; $R^5$ is —H; and n is 1.

13. The compound of claim 1, wherein $R^1$ is

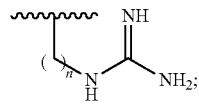

one of $R^2$, $R^3$, $R^4$, and $R^5$ is —Cl or —Br; three of $R^2$, $R^3$, $R^4$, and $R^5$ are —H; and n is 1.

14. The compound of claim 1, wherein $R^1$ is

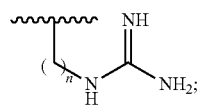

one of $R^2$ and $R^3$ is —Cl or —Br; one of $R^2$ and $R^3$ is —H; $R^4$ is —H; $R^5$ is —H; and n is 1.

15. The compound of claim 1, wherein $R^1$ is

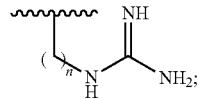

$R^2$ is —H; $R^3$ is —Cl or —Br; $R^4$ is —H; $R^5$ is —H; and n is 1.

16. The compound of claim 1, wherein $R^1$ is

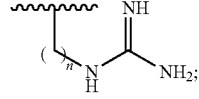

$R^2$ is —H; $R^3$ is substituted alkyl; $R^4$ is —H; $R^5$ is —H; and n is 1.

17. The compound of claim 1, wherein $R^1$ is

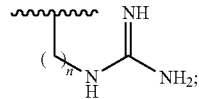

$R^2$ is —H; $R^3$ is substituted methyl; $R^4$ is —H; $R^5$ is —H; and n is 1.

18. A pharmaceutical composition comprising a compound that is

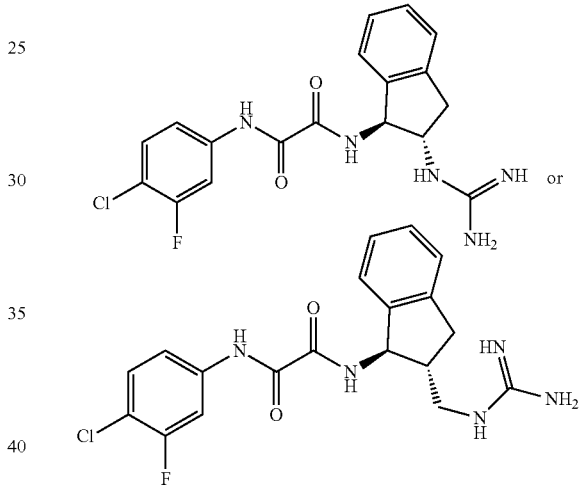

or a pharmaceutically acceptable salt thereof; and a pharmaceutically acceptable carrier.

19. The method of claim 8, wherein the compound is

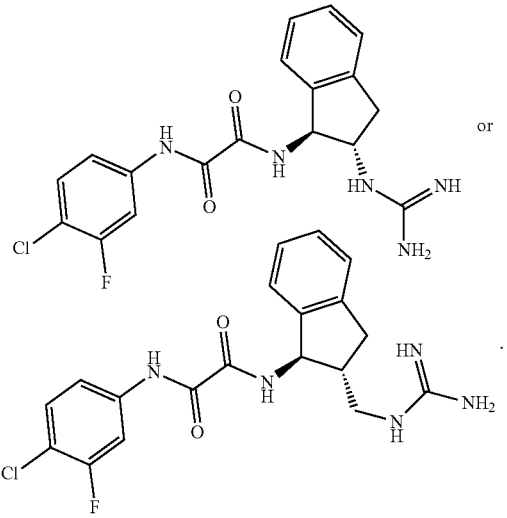

20. A method of treating HIV in a patient comprising administering to the patient a compound of claim 1.
21. The method of claim 20, wherein the compound is
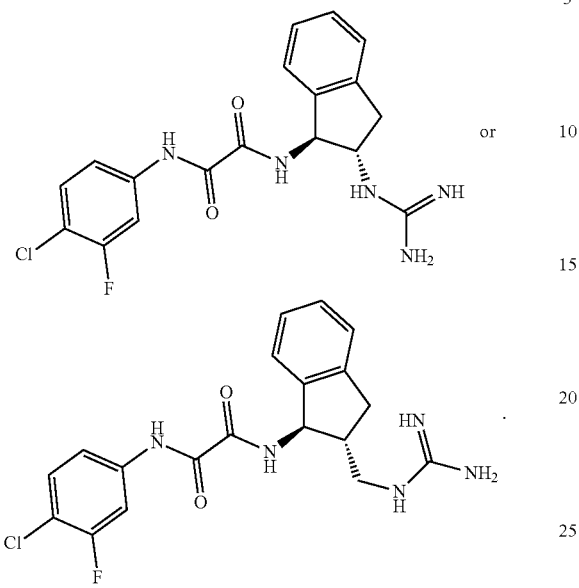
* * * * *